US007381253B2

(12) United States Patent
Mayo et al.

(10) Patent No.: US 7,381,253 B2
(45) Date of Patent: Jun. 3, 2008

(54) MULTI-CHROMOPHORIC AZO PYRIDONE COLORANTS

(75) Inventors: James D. Mayo, Mississauga (CA); James M. Duff, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 629 days.

(21) Appl. No.: 11/003,127

(22) Filed: Dec. 3, 2004

(65) Prior Publication Data
US 2006/0117991 A1 Jun. 8, 2006

(51) Int. Cl.
C09D 11/02 (2006.01)
(52) U.S. Cl. .................. 106/31.29; 106/31.61
(58) Field of Classification Search ............ 106/31.29, 106/31.61
See application file for complete search history.

(56) References Cited

U.S. PATENT DOCUMENTS

| 3,653,932 | A | 4/1972 | Berry et al. ................. 106/22 |
| 3,957,749 | A | 5/1976 | Von Brachel et al. ....... 260/156 |
| 4,216,145 | A | 8/1980 | Battisti et al. .............. 260/156 |
| 4,247,456 | A | 1/1981 | Von Brachel et al. ....... 260/156 |
| 4,359,418 | A | 11/1982 | Lienhard et al. ............ 260/156 |
| 4,390,369 | A | 6/1983 | Merritt et al. ................ 106/31 |
| 4,484,948 | A | 11/1984 | Merritt et al. ................ 106/31 |
| 4,644,058 | A | 2/1987 | Shimidzu et al. ........... 534/635 |
| 4,684,956 | A | 8/1987 | Ball ............................ 346/1.1 |
| 4,734,349 | A | 3/1988 | Chapman et al. ........... 430/106 |
| 4,851,045 | A | 7/1989 | Taniguchi ................... 106/31 |
| 4,889,560 | A | 12/1989 | Jaeger et al. ................ 106/27 |
| 4,889,761 | A | 12/1989 | Titterington et al. ........ 428/195 |
| 4,994,564 | A | 2/1991 | Etzbach et al. ............. 534/766 |
| 5,006,170 | A | 4/1991 | Schwarz et al. ............ 106/20 |
| 5,037,964 | A | 8/1991 | Moser et al. ................ 534/608 |
| 5,041,413 | A | 8/1991 | Evans et al. ................ 503/227 |
| 5,151,120 | A | 9/1992 | You et al. .................... 106/27 |
| 5,221,335 | A | 6/1993 | Williams et al. ............ 106/23 |
| 5,372,852 | A | 12/1994 | Titterington et al. ........ 427/288 |
| 5,496,879 | A | 3/1996 | Griebel et al. .............. 524/320 |
| 5,621,022 | A | 4/1997 | Jaeger et al. ................ 523/161 |
| 5,827,918 | A | 10/1998 | Titterington et al. ........ 524/590 |
| 5,853,929 | A | 12/1998 | Campbell .................... 430/45 |
| 5,902,841 | A | 5/1999 | Jaeger et al. ................ 523/161 |
| 5,919,839 | A | 7/1999 | Titterington et al. ........ 523/161 |
| 5,929,218 | A | 7/1999 | Lee et al. .................... 534/772 |
| 6,576,747 | B1 | 6/2003 | Carlini et al. ............... 534/649 |
| 6,576,748 | B1 | 6/2003 | Carlini et al. ............... 534/649 |
| 6,590,082 | B1 | 7/2003 | Banning et al. ............. 534/649 |
| 6,646,111 | B1 | 11/2003 | Carlini et al. ............... 534/649 |
| 6,663,703 | B1 | 12/2003 | Wu et al. .................... 106/31.29 |
| 6,673,139 | B1 | 1/2004 | Wu et al. .................... 106/31.29 |
| 6,696,552 | B2 | 2/2004 | Mayo et al. ................. 534/649 |
| 6,713,614 | B2 | 3/2004 | Carlini et al. ............... 534/649 |
| 6,755,902 | B2 | 6/2004 | Banning et al. ............. 106/31.29 |

FOREIGN PATENT DOCUMENTS

| EP | 0 063 275 A1 | 4/1982 |
| EP | 0 083 553 | 12/1982 |
| EP | 0 247 737 B1 | 12/1987 |
| EP | 0 172 283 B1 | 8/1988 |
| EP | 0 302 401 A1 | 2/1989 |

(Continued)

OTHER PUBLICATIONS

English abstract for German Patent Publication DE4205636AL.
English abstract for German Patent Publication DE4205713AL.
English abstract from Nerac for European Patent Publication 1 125 990 A1.
English abstract for Japanese Patent Publication JP05331382.
English abstract for German Patent Publication DE19646430.

(Continued)

Primary Examiner—J. A. Lorengo
Assistant Examiner—Veronica Faison-Gee
(74) Attorney, Agent, or Firm—Judith L. Byorick

(57) ABSTRACT

Disclosed is a compound comprising three or more moieties of the formula said moieties being bonded to a central atom, monomeric group of atoms, oligomer, or polymer. Also disclosed is a phase change ink composition comprising a phase change ink carrier and a colorant compound comprising three or more moieties of the formula said moieties being bonded to a central atom, monomeric group of atoms, oligomer, or polymer.

25 Claims, No Drawings

FOREIGN PATENT DOCUMENTS

| EP | 0 023 770 A1 | 3/1989 |
|---|---|---|
| EP | 0 142 863 B1 | 3/1989 |
| EP | 0 404 493 | 12/1990 |
| EP | 0 314 002 B1 | 9/1991 |
| EP | 0 319 234 B1 | 3/1995 |
| EP | 0 468 647 B1 | 3/1996 |
| EP | 0 524 637 | 6/1996 |
| EP | 0 706 679 B1 | 9/1997 |
| EP | 0 844 287 | 5/1998 |
| EP | 1 168 046 A1 | 1/2002 |
| GB | 2 008 606 | 6/1979 |
| GB | 1 559 001 | 1/1980 |
| WO | WO 95/00885 | 1/1995 |
| WO | WO 99/43754 | 9/1999 |
| WO | WO 01/21714 A2 | 3/2001 |
| WO | WO 01/09256 A1 | 8/2001 |

OTHER PUBLICATIONS

English abstract for German Patent Publication DE19646429.
English abstract for German Patent Publication DE19647869.
English abstract for German Patent Publication DE3538517.
English abstract for Japanese Patent Publication JP03192158.
English abstract for Japanese Patent Publication JP87290762 (JP62290762).
English abstract for Japanese Patent Publication JP 86244595 (JP61244595).
English abstract for Indian Patent Publication IN 147868.
English abstract for Spanish Patent Publication 475254 (Equivalent of Italian Patent Publication IT 1088895).
English abstract for German Patent Publication DE 2727809.
"Colour and Constitution of Azo Dyes Derived from 2-Thioalkyl-4,6-Diaminopyrimidines and 3-Cyano-1,4-dimethyl-6-hydroxy-2-pyridone as Coupling Components," L. Cheng et al., *Dyes and Pigments*, vol. 7, No. 5, pp. 373-388 (1986).
English abstract for Japanese Patent Publication JP 63039380.
Japanese Patent Publication JP 54102328.
Japanese Patent Publication JP 54070337.
"Trends in Modern Dye Chemistry. Part 10," N. R. Ayyangar and K. V. Srinivasan, *Colourage*, vol. 37, No. 2, pp. 29-30 (Jan. 16, 1990).
Japanese Patent Publication JP 05169854.
Japanese Patent Publication JP 04292988.
Japanese Patent Publication JP 63161060.
Japanese Patent Publication JP 61244595.
Korean Patent Publication KR 119563.
Japanese Patent Publication JP 00239549.
Japanese Patent Publication JP 11269402.
Japanese Patent Publication JP 09041267.
Japanese Patent Publication JP 08039941.
Japanese Patent Publication JP 06294909.
Japanese Patent Publication JP 06122829.
Japanese Patent Publication JP 05255602.
Japanese Patent Publication JP 05051536.
Japanese Patent Publication JP 04235093.
German Patent Publication DE 2606506.
"Preparation and Evaluation of Yellow Pigments Based on H-Pyridone and Esters of Aminoterephthalic Acid," P. Slosar et al., *CHEMagazin*, vol. 9, No. 6, pp. 8-11 (1999).
"Synthesis, Morphology, and Optical Properties of Tetrahedral Oligo(phenylenevinylene) Materials," S. Wang et al., *J. Am. Chem. Soc.*, vol. 120, p. 5695 (2000).
"Syntheses of Amphiphilic Diblock Copolymers Containing a Conjugated Block and Their Self-Assembling Properties," H. Wang et al., *J. Am. Chem. Soc.*, vol. 122, p. 6855 (2000).
"Crystal Engineering of Conjugated Oligomers and the Spectral Signature of $\pi$ Stacking in Conjugated Oligomers and Polymers," A. Koren et al., *Chem. Mater.*, vol. 12, p. 1519 (2000).
"The Chemistry of Isatoic Anhydride," G. M. Coppola, *Synthesis*, p. 505 (1980).
"Isatoic Anhydride. IV. Reactions with Various Nucleophiles," R. P. Staiger et al., *J. Org. Chem.*, vol. 24, p. 1214 (1959).
"Investigation of the Reaction Conditions for the Synthesis of 4,6-Disubstituted-3-cyano-2-pyridones and 4-Methyl-3-cyano-6-hydroxy-2-pyridone," D. Z. Mijin et al., *J. Serb. Chem. Soc.*, vol. 59, No. 12, p. 959 (1994).
"Synthesis of Isoquinoline Alkaloids. II. The Synthesis and Reactions of 4-Methyl-3-pyridinecarboxaldehyde and Other 4-Methyl-3-substituted Pyridines," J. M. Bobbitt et al., *J. Org. Chem.*, vol. 25, p. 560 (1960).
"Synthesis and Dyeing Characteristics of 5-(4-Arylazophenyl) azo-3-cyano-4-methyl-6-hydroxy-2-pyridones," J. Kanhere et al., *Indian Journal of Textile Research*, vol. 13, p. 213 (1988).
"Synthesis of Some Pyridone Azo Dyes from 1-Substituted 2-Hydroxy-6-pyridone Derivatives and their Colour Assessment," C. Chen et al., *Dyes and Pigments*, vol. 15, p. 69 (1991).
English abstract for German Patent Publication DE 3543360.
English abstract for Japanese Patent Publication JP 200121 4083.
English abstract for German Patent Publication DE 3505899.
English abstract for Indian Patent Publication 147527.
English abstract for Japanese Patent Publication JP 2000 62327.
English abstract for Japanese Patent Publication JP 85152563.
"Synthesis of 3-Cyano-6-hydroxy-5-(2-(perfluoroalkyl)phenylazo)-2-pyridones and their Application for Dye Diffusion Thermal Transfer Printing," *Bull. Chem. Soc. Jpn.*, 1993, vol. 66, Iss. 6, pp. 1790-1794.
English abstract for Chinese Patent Publication CN 1115773.
English abstract for German Patent Publication DE 3447117.
English abstract for Japanese Patent Publication JP 5331382.
English abstract for Japanese Patent Publication JP 63210169.
English abstract for Japanese Patent Publication JP 63199764.
English abstract for Japanese Patent Publication JP 63199763.
English abstract for Japanese Patent Publication JP 63199762.
English abstract for Japanese Patent Publication JP 63199761.
English abstract for Japanese Patent Publication JP 63199760.
English abstract for Japanese Patent Publication JP 63071392.
English abstract for Japanese Patent Publication JP 61181865.
English abstract for Japanese Patent Publication JP 61036366.
English abstract for Japanese Patent Publication JP 60152563.
English abstract for Japanese Patent Publication JP 60112862.
English abstract for Japanese Patent Publication JP 60112861.
English abstract for Japanese Patent Publication JP 58149953.
English abstract for Japanese Patent Publication JP 56092961.
English abstract for Japanese Patent Publication JP 56026957.
English abstract for Japanese Patent Publication JP 55099958.
English abstract for Japanese Patent Publication JP 96 11443.
English abstract for Japanese Patent Publication JP 93169849.
English abstract for Japanese Patent Publication JP 93 51536.
English abstract for Japanese Patent Publication JP 90185569.
English abstract for German Patent Publication DE 2606506.

MULTI-CHROMOPHORIC AZO PYRIDONE COLORANTS

BACKGROUND

Disclosed herein are colorant compounds. More specifically, disclosed herein are colorant compounds particularly suitable for use in hot melt or phase change inks. One embodiment is directed to a compound comprising three or more moieties of the formula

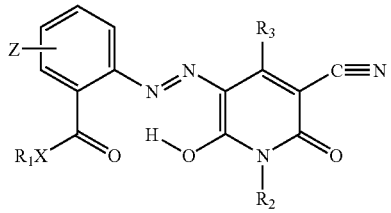

wherein (A) each $R_1$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, or (vi) a siloxy group, (B) each $R_2$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, (vi) a siloxy group, or (vii) a group of the formula

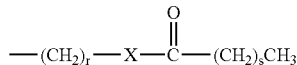

wherein r and s are each, independently of the other, integers representing a number of repeat —$CH_2$— groups, (C) each $R_3$, independently of the others, is (i) an alkyl group, (ii) an aryl group, (iii) an arylalkyl group, or (iv) an alkylaryl group, (D) each X, independently of the others, is (i) a direct bond, (ii) an oxygen atom, (iii) a sulfur atom, (iv) a group of the formula —$NR_{40}$— wherein $R_{40}$ is a hydrogen atom, an alkyl group, an aryl group, an arylalkyl group, or an alkylaryl group, or (v) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, and (E) each Z, independently of the others, is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

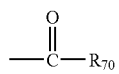

wherein $R_{70}$ is an alkyl group, an aryl group, an arylalkyl group, an alkylaryl group, a silyl group, or a siloxy group, (ix) a sulfonyl group of the formula —$SO_2R_{80}$ wherein $R_{80}$ is a hydrogen atom, an alkyl group, an aryl group, an arylalkyl group, an alkylaryl group, a silyl group, or a siloxy group, or (x) a phosphoryl group of the formula —$PO_3R_{90}$ wherein $R_{90}$ is a hydrogen atom, an alkyl group, an aryl group, an arylalkyl group, an alkylaryl group, a silyl group, or a siloxy group; said moieties being bonded to a central atom, monomeric group of atoms, oligomer, or polymer. Another embodiment is directed to a phase change ink comprising a phase change ink carrier and a colorant compound comprising three or more moieties of the formula

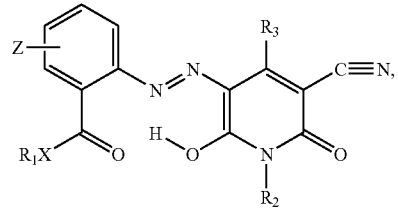

said moieties being bonded to a central atom, monomeric group of atoms, oligomer, or polymer.

In general, phase change inks (sometimes referred to as "hot melt inks") are in the solid phase at ambient temperature, but exist in the liquid phase at the elevated operating temperature of an ink jet printing device. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops. Phase change inks have also been used in other printing technologies, such as gravure printing, as disclosed in, for example, U.S. Pat. No. 5,496,879 and German Patent Publications DE 4205636AL and DE 4205713AL, the disclosures of each of which are totally incorporated herein by reference.

Phase change inks for color printing typically comprise a phase change ink carrier composition which is combined with a phase change ink compatible colorant. In a specific embodiment, a series of colored phase change inks can be formed by combining ink carrier compositions with compatible subtractive primary colorants. The subtractive primary colored phase change inks can comprise four component dyes, namely, cyan, magenta, yellow and black, although the inks are not limited to these four colors. These subtractive primary colored inks can be formed by using a single dye or a mixture of dyes. For example, magenta can be obtained by using a mixture of Solvent Red Dyes or a composite black can be obtained by mixing several dyes. U.S. Pat. No. 4,889,560, U.S. Pat. No. 4,889,761, and U.S. Pat. No. 5,372,852, the disclosures of each of which are totally incorporated herein by reference, teach that the subtractive primary colorants employed can comprise dyes from the classes of Color Index (C.I.) Solvent Dyes, Disperse Dyes, modified Acid and Direct Dyes, and Basic Dyes. The colorants can also include pigments, as disclosed in, for example, U.S. Pat. No. 5,221,335, the disclosure of which is totally incorporated herein by reference. U.S. Pat. No. 5,621,022, the disclosure of which is totally incorporated herein by reference, discloses the use of a specific class of polymeric dyes in phase change ink compositions.

Phase change inks have also been used for applications such as postal marking, industrial marking, and labelling.

Phase change inks are desirable for ink jet printers because they remain in a solid phase at room temperature during shipping, long term storage, and the like. In addition, the problems associated with nozzle clogging as a result of ink evaporation with liquid ink jet inks are largely eliminated, thereby improving the reliability of the ink jet printing. Further, in phase change ink jet printers wherein the ink droplets are applied directly onto the final recording substrate (for example, paper, transparency material, and the like), the droplets solidify immediately upon contact with the substrate, so that migration of ink along the printing medium is prevented and dot quality is improved.

Compositions suitable for use as phase change ink carrier compositions are known. Some representative examples of references disclosing such materials include U.S. Pat. Nos. 3,653,932, 4,390,369, 4,484,948, 4,684,956, 4,851,045, 4,889,560, 5,006,170, 5,151,120, 5,372,852, 5,496,879, European Patent Publication 0187352, European Patent Publication 0206286, German Patent Publication DE 4205636AL, German Patent Publication DE 4205713AL, and PCT Patent Application WO 94/04619, the disclosures of each of which are totally incorporated herein by reference. Suitable carrier materials can include paraffins, microcrystalline waxes, polyethylene waxes, ester waxes, fatty acids and other waxy materials, fatty amide containing materials, sulfonamide materials, resinous materials made from different natural sources (tall oil rosins and rosin esters, for example), and many synthetic resins, oligomers, polymers, and copolymers.

U.S. Pat. No. 6,576,747 (Carlini et al.), the disclosure of which is totally incorporated herein by reference, discloses a process for preparing dianthranilate compounds which comprises (a) admixing reactants as follows: (1) a diol of the formula $R_1(OH)_2$, wherein $R_1$ is an alkylene group having at least about 20 carbon atoms, and wherein the —OH groups are primary or secondary, (2) isatoic anhydride, present in an amount of at least about 2 moles of isatoic anhydride per every one mole of diol, (3) a catalyst which is 1,4-diazabicyclo(2.2.2)octane, N,N,N',N'-tetramethylethylene diamine, or a mixture thereof, said catalyst being present in an amount of at least about 0.2 mole of catalyst per every one mole of diol, and (4) a solvent; and (b) heating the mixture thus formed to form a dianthranilate compound of the formula

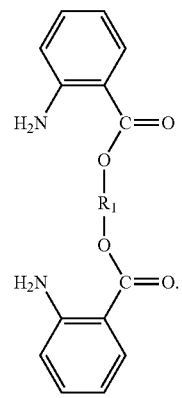

Also disclosed is a process for preparing diazopyridone colorants which comprises (I) preparing a dianthranilate compound by the aforementioned method, (II) reacting the dianthranilate compound with nitrosylsulfuric acid to form a diazonium salt, and (III) reacting the diazonium salt with a pyridone compound to form a diazopyridone compound.

U.S. Pat. No. 6,713,614 (Carlini et al.), the disclosure of which is totally incorporated herein by reference, discloses compounds of the formula

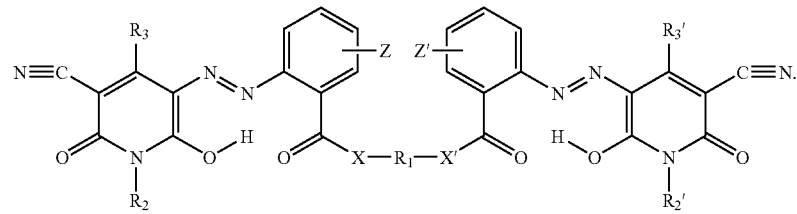

The compounds are useful as colorants, particularly in applications such as phase change inks.

U.S. Pat. No. 6,663,703 (Wu et al.), the disclosure of which is totally incorporated herein by reference, discloses a phase change ink composition comprising a phase change ink carrier and a colorant compound of the formula

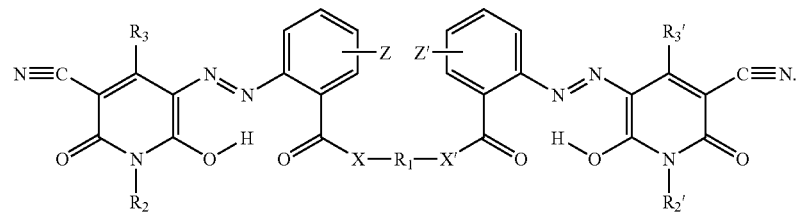

U.S. Pat. No. 6,755,902 (Banning et al.), the disclosure of which is totally incorporated herein by reference, discloses a phase change ink composition comprising a phase change ink carrier and a colorant compound of the formula

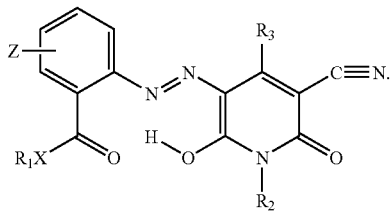

U.S. Pat. No. 6,590,082 (Banning et al.), the disclosure of which is totally incorporated herein by reference, discloses compounds of the formula

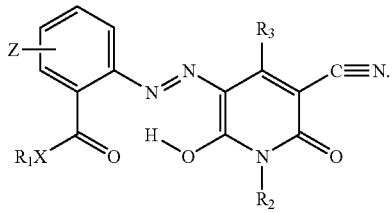

The compounds are useful as colorants, particularly in applications such as phase change inks.

U.S. Pat. No. 6,696,552 (Mayo et al.), the disclosure of which is totally incorporated herein by reference, discloses a process for preparing substituted pyridone compounds which comprises (a) admixing in the absence of a solvent (1) an amine of the formula $R_1$—$NH_2$ wherein $R_1$ is an alkyl group, an aryl group, an arylalkyl group, or an alkylaryl group, and (2) a first ester of the formula

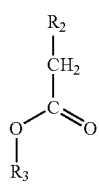

wherein $R_2$ is an electron withdrawing group and $R_3$ is an alkyl group; (b) heating the mixture containing the amine and the first ester to form an intermediate compound of the formula

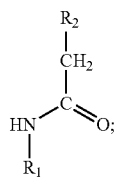

(c) admixing the intermediate compound with (1) a base and (2) a second ester of the formula

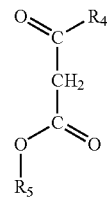

wherein $R_4$ is an alkyl group, an aryl group, an arylalkyl group, or an alkylaryl group and $R_5$ is an alkyl group, said second ester being present in a molar excess relative to the intermediate compound, said base being present in a molar excess relative to the intermediate compound, and (d) heating the mixture containing the intermediate compound, the second ester, and the base to form a pyridone compound of the formula

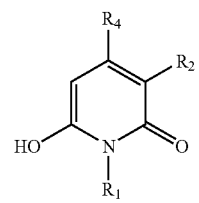

or a salt thereof. Also disclosed is a process for preparing diazopyridone colorants which comprises preparing a pyridone compound by the above process and reacting the pyridone compound with a diazonium salt to form a diazopyridone compound.

U.S. Pat. No. 6,576,748 (Carlini et al.), the disclosure of which is totally incorporated herein by reference, discloses a process for preparing a diazopyridone compound which comprises (a) preparing a first solution comprising (1) either (A) a dianiline of the formula

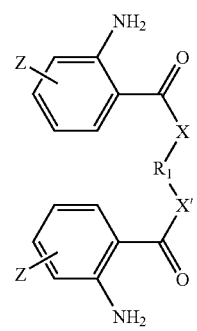

or (B) an aniline of the formula

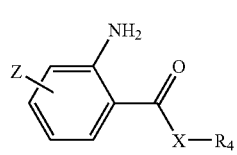

and (2) a first solvent mixture comprising (I) a solvent, (II) acetic acid, and (III) an optional second acid, said acetic acid being present in the solvent mixture in an amount of at least about 95 percent by weight of the solvent mixture, said first solution being at a temperature of about +15° C. or lower; (b) adding to the first solution nitrosylsulfuric acid, thereby forming a diazonium salt either (A) of the formula

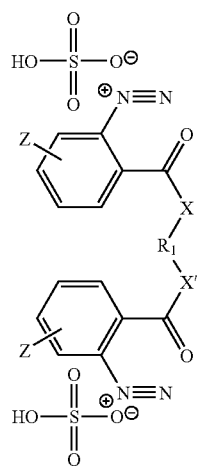

or (B) of the formula

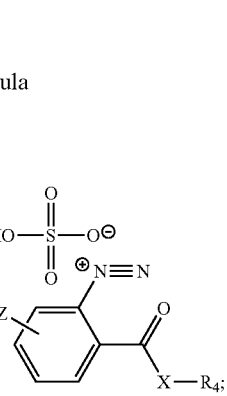

(c) preparing a second solution comprising (1) a second solvent mixture comprising water and an organic solvent soluble in or miscible in water, (2) either (A) a pyridone of the formula

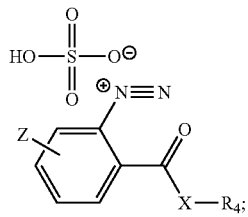

or (B) a dipyridone of the formula (3) a base present in an amount of at least about 3 molar equivalents of base per mole of pyridone moiety, and (4) an optional buffer salt, and (d) combining either (A) the second solution containing the dianiline and the first solution containing the pyridone, or (B) the second solution containing the aniline and the first solution containing the dipyridone to form a third solution and effect a coupling reaction to form a diazopyridone compound either (A) of the formula or (B) of the formula

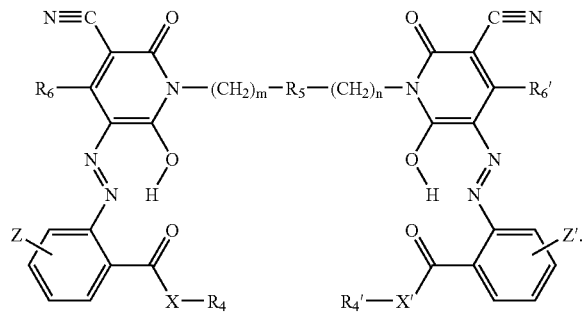

U.S. Pat. No. 6,646,111 (Carlini et al.), the disclosure of which is totally incorporated herein by reference, discloses compounds of the formula

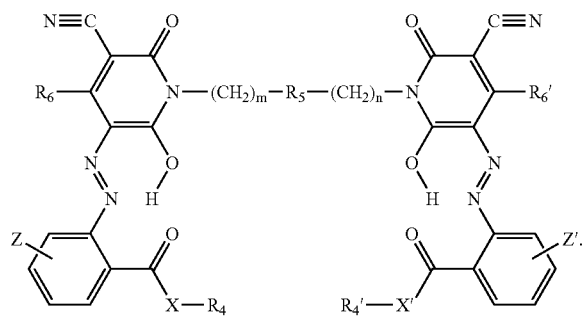

The compounds are useful as colorants, particularly in applications such as phase change inks.

U.S. Pat. No. 6,673,139 (Wu et al.), the disclosure of which is totally incorporated herein by reference, discloses a phase change ink composition comprising a phase change ink carrier and a colorant compound of the formula

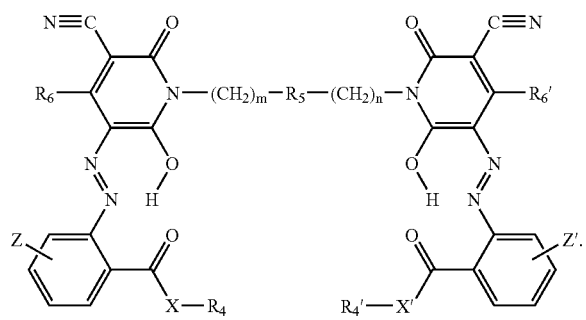

European Patent Publication 1 125 990 A1 and PCT Patent Publication WO 01/09256 A1, the disclosures of each of which are totally incorporated herein by reference, discloses an aqueous ink for ink jet recording which contains at least a water-insoluble coloring matter, water, and a resin as main components and which takes the form of an emulsion, which is characterized by containing at least one yellow hue coloring matter selected from the group consisting of a quinophthalone compound represented by the formula (1)

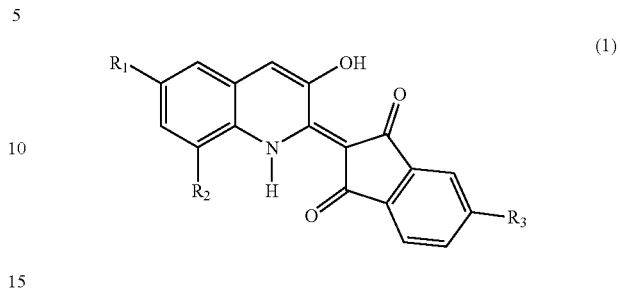

wherein each of $R_1$ to $R_3$ independently represents a hydrogen atom, an unsubstituted or substituted alkyl group, —$CONR_4R_5$, or —$COOR_6$ (in which each of $R_4$ to $R_6$ independently represents a hydrogen atom, an unsubstituted or substituted alkyl group, or an unsubstituted or substituted aryl group) and all of $R_1$ to $R_3$ are not a hydrogen atom at the same time, and a pyridone azo compound represented by the formula (2)

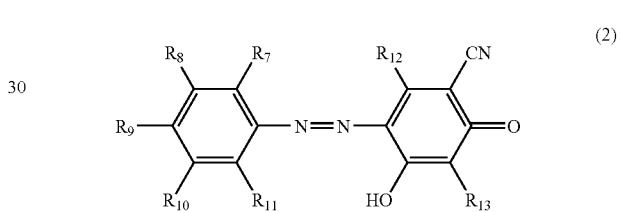

wherein each of $R_7$ to $R_{11}$ independently represents a hydrogen atom, a halogen atom, an unsubstituted or substituted alkyl group, an aralkyl group, an unsubstituted or substituted alkoxy group, an unsubstituted or substituted aryl group, an unsubstituted or substituted aryloxy group, a hydroxyl group, —$NR_{14}R_{15}$ (in which $R_{14}$ and $R_{15}$ independently represent a hydrogen atom, an unsubstituted or substituted alkyl group, or an aralkyl group), —$COX_1$ (in which $X_1$ represents an unsubstituted or substituted alkoxy group, an unsubstituted or substituted aryloxy group, or —$NR_{16}R_{17}$ (in which each of $R_{16}$ and $R_{17}$ independently represent a hydrogen atom, an unsubstituted or substituted alkyl group, an aralkyl group, or an unsubstituted or substituted aryl group)), —$COO(CH_2)_n$—$COX_2$, —$OCOX_3$, or —$NHCOX_4$ (in which each of $X_2$ to $X_4$ independently represents an unsubstituted or substituted alkyl group, an aralkyl group, an unsubstituted or substituted aryl group, an unsubstituted or substituted alkoxy group, or an unsubstituted or substituted aryloxy group, and n is an integer of 1 to 3), $R_{12}$ represents an unsubstituted or substituted alkyl group, and $R_{13}$ represents an unsubstituted or substituted alkyl group, an aralkyl group, or an unsubstituted or substituted aryl group. The ink is for ink jet recording having excellent light resistance and storage stability, and enables formation of a high quality image without blotting, and the obtained recording image is excellent in water resistance.

PCT Patent Publication WO 01/21714, the disclosure of which is totally incorporated herein by reference, discloses compositions comprising a solvent and at least one compound of the formula

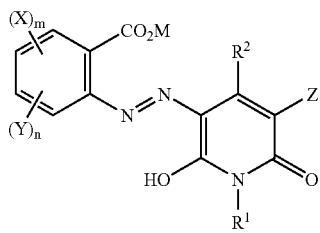

in which $R_1$ represents H, an optionally substituted $C_{1-8}$ carbyl derived group, or a group of the formula

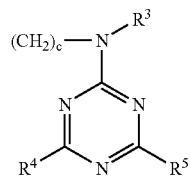

where C is from 2 to 6, $R^3$ represents optionally substituted $C_{1-8}$ carbyl derived group, $R^4$ and $R^5$ independently represent an optional substituent, $R^2$ represents an optionally substituted $C_{1-8}$ carbyl derived group, X, Y, and Z independently represent H or an optional substituent, M represents H or a cation, and m and n independently represent 0, 1, or 2. Also disclosed are compounds of the above formula providing that at least one of $R^1$, $R^2$, X, Y, or Z comprises a group of formula $SO_3M$ or $PO_3M_2$. These compositions and compounds are useful as the colorants to prepare color filters for displays.

U.S. Pat. No. 4,247,456 (von Brachel et al.), the disclosure of which is totally incorporated herein by reference, discloses water-insoluble monoazo dyes of the formula

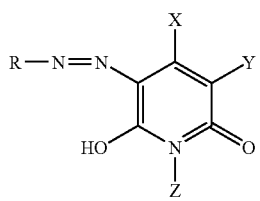

wherein R is the residue of a benzene, naphthalene, diphenyl, diphenylmethane, or heterocyclic diazo compound which is free from water solubilizing groups, produced by reacting a diazotized amine of the benzene, naphthalene, diphenyl, diphenylmethane, or heterocyclic series which is free from water solubilizing groups with the appropriate 6-hydroxy-2-pyridone and the utility thereof for the dyeing and printing of synthetic fabric materials to yellow to red shades having excellent fastness to light and sublimation.

U.S. Pat. No. 3,957,749 (von Brachel et al.), the disclosure of which is totally incorporated herein by reference, discloses water-insoluble monoazo dyes of the formula

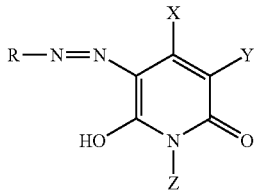

produced by reacting a diazotized amine of the benzene, naphthalene, diphenyl, diphenylmethane, or heterocyclic series which is free from water solubilizing groups with the appropriate 6-hydroxy-2-pyridone and the utility thereof for the dyeing and printing of synthetic fabric materials to yellow to red shades having excellent fastness to light and sublimation.

Japanese Patent Publication JP 05331382, the disclosure of which is totally incorporated herein by reference, discloses a specific pyridone azo pigment which is bright yellow and highly soluble in a solvent, absorbs light of long wavelength, and is useful for a thermal transfer sheet. The pyridone azo pigment is represented by the formula

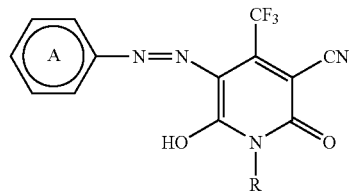

wherein R is H, alkyl, substituted alkyl, cycloalkyl, aryl, or optionally substituted phenyl, and ring A is a benzene ring optionally having a nonionic group. The pigment is prepared by diazotizing an aniline compound and coupling the resulting diazo compound with a pyridone compound. Having a good solubility in an organic solvent and a good dispersibility in water, the pigment facilitates the preparation of an ink containing a high concentration of the pigment homogeneously dissolved or dispersed. The prepared ink enables the preparation of a thermal transfer sheet coated with the ink uniformly in a high density.

British Patent 1,559,001 (Harvey et al.), the disclosure of which is totally incorporated herein by reference, discloses a hydrophilic textile material colored with a dyestuff of the formula

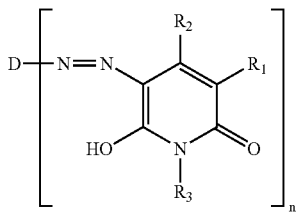

wherein D is the residue of a diazo or tetrazo component; $R_1$ is a hydrogen atom or an alkyl, chloro, acetamido, benzamido, carbamoyl, or an N-substituted carbamyl, for example —CONHBr, group or, preferably, a cyano group; $R_2$ is an alkyl group, especially methyl, optionally substituted with a chlorine atom, a phenyl group, optionally substituted with an alkyl or alkoxy group, or a carboxylic acid or carboxylic acid ester group; or $R_1$ and $R_2$ together with the carbon atoms in the 3- or 4-position of the pyridone ring may form an alicyclic or aromatic ring system so that, for example, $R_1$ and $R_2$ together may be a tri- or tetra-methylene group forming with the pyridone of penteno (c) or hexeno (c) pyrid-2-one, or $R_1$ and $R_2$ may form together with the adjacent carbon atoms of the pyridone ring a benzene ring giving a benz (c) pyrid-2-one; $R_3$ is an aryl group carrying one or more substituents selected from —NO, —$SO_2R^1$, —$COR^1$, —$COOR^1$, —CF, or —CN, wherein $R^1$ is an optionally substituted alkyl or aryl group; and n is an integer which may be 1 or 2.

German Patent Publication DE 19646430, the disclosure of which is totally incorporated herein by reference, discloses dye mixtures comprising at least two structurally different dyes, each corresponding to formula

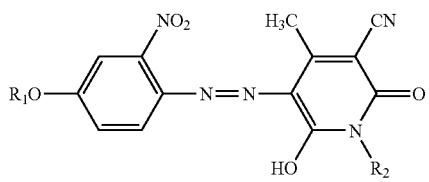

wherein $R_1$ is $C_1$-$C_4$ alkyl; $R_2$ is the $(CH_2)_nO$—$R_5$ radical; $R_s$ is, independently of $R_1$, $C_1$-$C_4$ alkyl or phenyl (which is unsubstituted or substituted by $C_1$-$C_4$ alkyl, $C_1$-$C_4$ alkoxy, hydroxy, or halogen); and n is 2 or 3, which dye mixtures are suitable for dyeing or printing textile fibre materials (e.g. polyester materials), giving dyeings having good around fastness properties.

German Patent Publication DE 19646429, the disclosure of which is totally incorporated herein by reference, discloses dye mixtures comprising at least two structurally different dyes, each of which has the formula

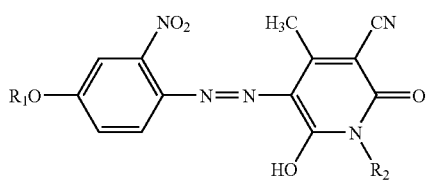

in which $R_1$ is $C_1$-$C_4$ alkyl and $R_2$ is isopropyl, n-butyl, isobutyl, sec-butyl, or tert-butyl; or $C_1$-$C_3$ alkyl which is substituted by phenyl or phenoxy; or $R_1$ is phenyl (which is unsubstituted or substituted by $C_1$-$C_4$ alkyl, $C_1$-$C_4$ alkoxy, hydroxyl, or halogen), $C_1$-$C_4$ alkoxy-$C_1$-$C_3$ alkylene, phenoxy-$C_1$-$C_3$ alkylene, or $C_1$-$C_3$ alkyl which is substituted by phenyl (which is unsubstituted or substituted by $C_1$-$C_4$ alkyl, $C_1$-$C_4$ alkoxy, hydroxyl, or halogen) and $R_2$ is $C_1$-$C_{10}$ alkyl (which is unsubstituted or substituted by hydroxyl, $OCOR_3$, or phenoxy, where the phenyl ring in phenoxy is unsubstituted or substituted by $C_1$-$C_4$ alkyl, $C_1$-$C_4$ alkoxy, hydroxyl, or halogen) and the alkyl chain in $C_1$-$C_{10}$ alkyl from $C_2$ can be interrupted by one or more oxygen atoms; phenyl (which is unsubstituted or substituted by $C_1$-$C_4$ alkyl, $C_1$-$C_4$ alkoxy, hydroxyl, or halogen); or $C_5$-$C_7$ cycloalkyl; and $R_3$ is $C_1$-$C_4$ alkyl, are suitable for dyeing or printing textile fibre materials (e.g. polyester materials) and give dyeings with good allround properties.

German Patent Publication DE 19647869, the disclosure of which is totally incorporated herein by reference, discloses a dye mixture containing at least 2 dyes with different structures, each of formula

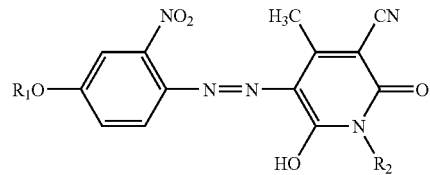

where $R_1$ is a 1-4C alkyl; and $R_2$ is a linear 1-3C alkyl. Also claimed is hydrophobic fibre material, preferably polyester textile material, dyed or printed with the mixture.

PCT Patent Publication WO 99/43754, the disclosure of which is totally incorporated herein by reference, discloses compounds of the formula

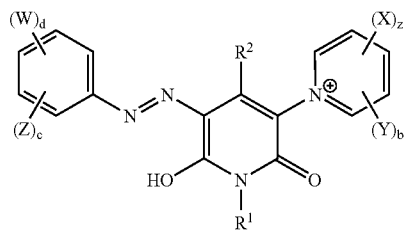

and salts and tautomers thereof, wherein: $R_1$ and $R_2$ each independently is H, optionally substituted alkyl, optionally substituted aryl, or optionally substituted arylalkyl; each W and each X independently is —COOH, —$SO_3H$, —$PO_3H_2$, or alkyl substituted by one or more groups selected from —COOH, —$SO_3H$, and —$PO_3H_2$; each Y and each Z independently is a substituent other than those defined for W and X; a and d each independently is 1 to 5; b and c each independently is 0 to 4; (a+b) has a value of 5 or less; and (c+d) has a value of 5 or less. Also claimed are inks containing a compound of this formula, an ink jet printing process using the inks, substrates printed with the inks, and ink jet printer cartridges containing the inks.

U.S. Pat. No. 5,929,218 (Lee et al.), the disclosure of which is totally incorporated herein by reference, discloses pyridone-based yellow monoazo dyes used in thermal transfer having following formula which have good stability and hue

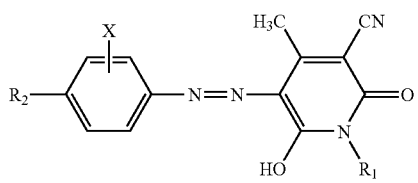

wherein $R_1$ is hydrogen atom; unsubstituted or substituted alkyl group of from 1 to 8 carbon atoms with alkoxy or aryl;

or unsubstituted or substituted aryl group with alkoxy or halogen, and X is hydrogen atom; alkyl group of from 1 to 4 carbon atoms; alkoxy group; or halogen; $R_2$ is selected from the following groups;

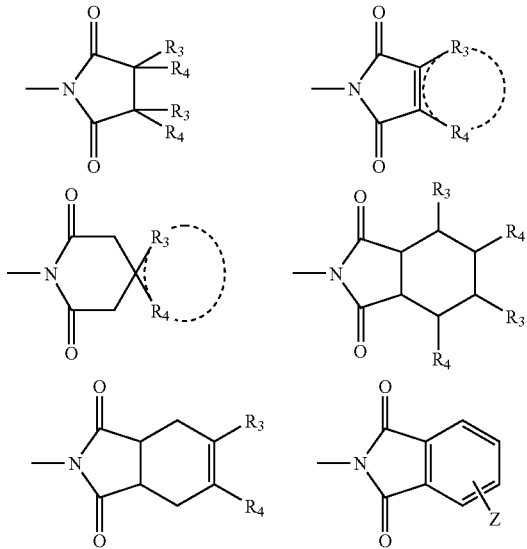

wherein $R_3$ and $R_4$ are independently selected from groups consisting hydrogen, substituted or unsubstituted alkyl group of from 1 to 4 carbon atoms, halogen, alkyl carboxylate, and carbonyl group; $R_3$-$R_4$ is noncyclization with $R_3$ and $R_4$ and selected respectively from the above substituents ($R_3$ and $R_4$); or saturated or unsaturated cycloalkyl of from 3 to 6 carbon atoms, Z is nitro, halogen, alkyl group of from 1 to 4 carbon atoms, alkoxy, sulfonyl, carbonyl, carboxyamide, sulfonamino, cyano, hydroxy, or hydrogen atom.

European Patent Publication EP 0 706 679 B1, U.S. Pat. No. 5,853,929 (Campbell), and PCT Patent Publication WO 95/00885, the disclosures of each of which are totally incorporated herein by reference, disclose colored cyan toner for electroreprography and laser printing based on Solvent Blue 70, and a trichomatic set of coloured toners based on Solvent Blue 70, benzodifuranone red dyes, and azo pyridone yellow dyes of the formula

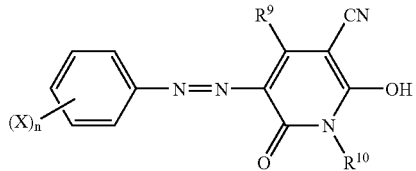

wherein X is halogen, nitro, or a group —COOR$^5$, R$^9$ is $C_{1-4}$ alkyl, R$^{10}$ is $C_{1-12}$ alkyl, R$^5$ is $C_{1-8}$ alkyl or a group of formula —($C_{1-3}$-alkylene)-(CO)$_q$-Z wherein q is 0 or 1 and Z is —OR$^6$ or —NR$^6$R$^7$ when q=1 or Z is —OR$^8$ when q=0, R$^6$ is selected from optionally substituted $C_{1-8}$ alkyl, optionally substituted $C_{1-8}$ alkoxy-$C_{1-8}$ alkyl, and a second group represented by R$^5$ in which R$^6$ is optionally substituted $C_{1-8}$ alkyl or optionally substituted $C_{1-8}$ alkoxy-$C_{1-8}$ alkyl, R$^7$ is selected from H and optionally substituted $C_{1-8}$ alkyl, and R$^8$ is selected from optionally substituted $C_{1-8}$ alkyl, optionally substituted $C_{1-8}$ alkoxy-$C_{1-8}$ alkyl, optionally substituted $C_{1-8}$ alkyl sulfonyl or carbonyl, and optionally substituted phenyl sulfonyl or carbamoyl.

European Patent Publication EP 0 247 737, the disclosure of which is totally incorporated herein by reference, discloses a thermal transfer printing sheet suitable for use in a thermal transfer printing process, especially for the conversion of a digital image into a visible print, comprising a substrate having a coating comprising a dye of the formula

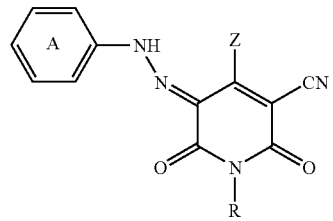

wherein Ring A is unsubstituted or carries, in the 2- or 4-position with respect to the azo link, at least one group selected from —CX$_3$, X$^1$, CN, NO$_2$, —OCO.Y, —CO.Y, —CO.H, —OSO$_2$.Y, and —SO$_2$.Y, provided that A is substituted when Z is CH$_3$ and R is $C_{2-4}$-alkyl; X and X$^1$ are each independently halogen; Y is selected from R$^1$, —OR$^1$, SR$^1$, and —NR$^1$R$^2$; R$^1$ is selected from $C_{1-12}$-alkyl, $C_{1-12}$-alkyl interrupted by one or two groups selected from —O—, —CO—, O.CO—, and —CO.O—, $C_{3-7}$-cycloalkyl, mono- or bi-cyclic aryl, and $C_{1-3}$-alkylene attached to an adjacent carbon atom on Ring A; R$^2$ is selected from H, $C_{1-12}$-alkyl, $C_{3-7}$-cycloalkyl, and mono- or bi-cyclic aryl; Z is $C_{1-12}$-alkyl or phenyl; and R is selected from $C_{2-12}$-alkyl unbranched in the alpha-position, $C_{2-12}$-alkyl unbranched in alpha-position and interrupted by one or two groups selected from —O—, —CO—, O.CO—, and —CO.O—, phenyl, $C_{1-4}$-alkylphenyl, biphenyl, and biphenyl interrupted by a group selected from —O—, —CO—, O.CO—, and —CO.O—, each of which is free from hydrogen atoms capable of intermolecular hydrogen bonding.

U.S. Pat. No. 5,041,413 (Evans et al.), the disclosure of which is totally incorporated herein by reference, discloses a yellow dye-donor element for thermal dye transfer comprises a support having thereon a dye layer comprising a mixture of yellow dyes dispersed in a polymeric binder, at least one of the yellow dyes having the formula

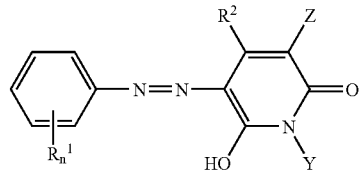

wherein: each R$^1$ independently represents a substituted or unsubstituted alkyl group of from 1 to about 10 carbon atoms, a cycloalkyl group of from about 5 to about 7 carbon atoms; a substituted or unsubstituted allyl group; an aryl group of from about 6 to about 10 carbon atoms; a hetaryl group of from 5 to 10 atoms; acyl; arylsulfonyl; aminocarbonyl; aminosulfonyl; fluorosulfonyl; halogen; nitro; alkylthio; or arylthio; or any two adjacent R$^1$'s together represent the atoms necessary to form a 5- or 6-membered fused ring; n represents an integer from 0-4; R$^2$ represents hydrogen; a substituted or unsubstituted alkyl, cycloalkyl, allyl, aryl or hetaryl group as described above for R$^1$; cyano; acyl; alkylsulfonyl; arylsulfonyl; or alkoxycarbonyl; Z represents cyano; alkoxycarbonyl; acyl; nitro; arylsulfonyl or alkylsulfonyl; Y represents hydrogen; a substituted or unsubstituted alkyl, cycloalkyl, allyl, aryl or hetaryl group as described above for $R^1$; amino; alkylamino; arylamino; acylamino; or sulfonylamino; and at least one of the other of the dyes having the formula

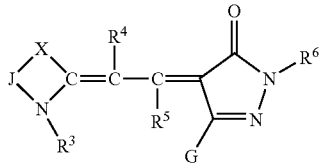

wherein $R^3$ represents the same groups as $R^1$ above; $R^4$ and $R^5$ each independently represents hydrogen, $R^3$; cyano; acyloxy; alkoxy of 1 to about 6 carbon atoms; halogen; or alkoxycarbonyl; or any two of $R^3$, $R^4$ and $R^5$ together represent the atoms necessary to complete a 5- to 7-membered ring; $R^6$ represents the same groups as $R^3$; G represents a substituted or unsubstituted alkyl, cycloalkyl or allyl group as described above for $R^3$, $NR^7R^8$ or $OR^9$; $R^7$ and $R^8$ each independently represents hydrogen, acyl or $R^3$, with the proviso that $R^7$ and $R^8$ cannot both be hydrogen at the same time; or $R^7$ and $R^8$ together represent the atoms necessary to complete a 5- to 7-membered ring; $R^9$ represents the same groups as $R^3$; X represents $C(R^{10})(R^{11})$, S, O or $NR^{10}$; $R^{10}$ and $R^{11}$ each independently represents the same groups as $R^3$; or $R^{10}$ and $R^{11}$ together represent the atoms necessary to complete a 5- to 7-membered ring; and J represents the atoms necessary to complete a 5- or 6-membered ring which may be fused to another ring system.

U.S. Pat. No. 4,359,418 (Lienhard et al.), the disclosure of which is totally incorporated herein by reference, discloses azo dyestuff sulfonic acid salts of the formula

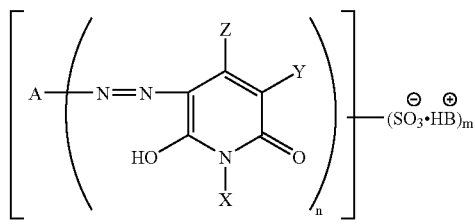

wherein A represents a carbocyclic or heterocyclic aromatic radical, B represents an aliphatic, cycloaliphatic or araliphatic amine, X represents a hydrogen atom or a substituted or unsubstituted alkyl group, a cycloalkyl, aralkyl or aryl group, Y represents a hydrogen or halogen atom, a nitro, cyano, acyl, sulfonic acid, arylsulfonyl, alkoxycarbonyl group or a substituted or unsubstituted alkyl, sulfamoyl or carbamoyl group, Z represents a substituted or unsubstituted alkyl group or an aryl radical, m and n are 1 or 2; said dyestuffs salts having good solubility in organic solvents and functioning to color solutions of film forming polymers in yellow to orange shades.

German Patent Publication DE 3538517 and U.S. Pat. No. 5,037,964 (Moser et al.), the disclosures of each of which are totally incorporated herein by reference, disclose sulfonic acid group-free basic azo compounds, which correspond in one of the possible tautomeric forms to the formula

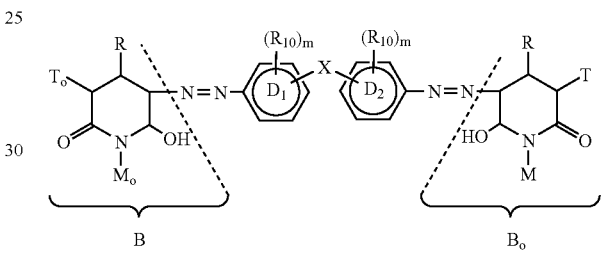

their preparation and their use for dyeing paper.

Japanese Patent Publication JP 03192158, the disclosure of which is totally incorporated herein by reference, discloses obtaining a yellow dye exhibiting high dyeing speed and degree of exhaustion in dyeing a textile material, leather, pulp, paper, etc., as well as excellent brightness and fastness to water by selecting a compound wherein a pyridopyridinium salt is linked to diphenylfluorene through azo groups. A cationic compound of the formula

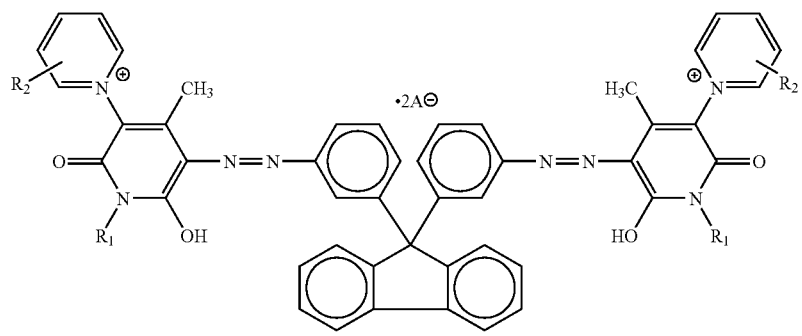

wherein $R_1$ is H or 1-4C alkyl; $R_2$ is H, 1-4C alkyl, or alkoxy; and $A^-$ is an anion which has a structure wherein a tetrazo compound, of 9,9'-bis(4-anilino)fluorene is coupled with a pyridone derivative is selected as a yellow dye, which is useful for dyeing an unsized pulp or paper (e.g. a napkin, table cloth, or sanitary paper). The dyeing with the dye is carried out at a pH of 4-8, preferably 5-7, and at 10-50° C., preferably 15-30° C.

British Patent Publication GB 2 008 606, the disclosure of which is totally incorporated herein by reference, discloses water-insoluble yellow monoazo dyes suitable for dyeing hydrophobic synthetic fibres, particularly polyesters, having the formula

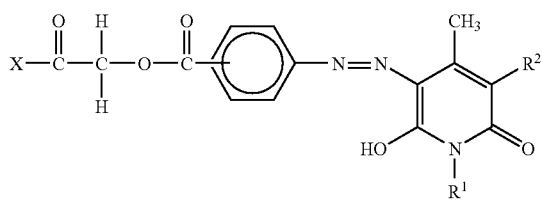

in which X represents $OR^3$ or $NHR^3$, $NR^3R^4$ ($R^3$, $R^4$ together optionally forming with N a ring having 5 to 6 carbon atoms), $NHR^5$; $R^1$ represents a hydrogen atom, an alkyl having 1 to 5 carbon atoms, $(CH_2)_2OH$ or $(CH_2)^3OR_3$; $R^2$ represents CN, $COOR^3$, $CONHR^3$, $CONR^3R^4$ ($R^3$, $R^4$ together optionally forming with N a ring having 5 to 6 carbon atoms); $R^3$ and $R^4$ represent alkyl groups having 1 to 5 carbon atoms; and $R^5$ represents a cycloalkyl having 5 or 6 carbon atoms. The dyes may be prepared by the reaction of

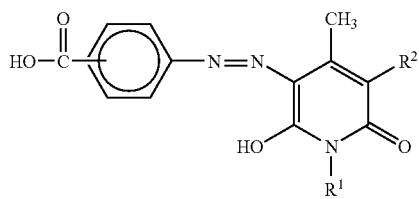

with $Hal-CH_2-CO-X$ in which Hal represents Cl or Br.

"Preparation and Evaluation of Yellow Pigments Based on H-Pyridone and Esters of Aminoterephthalic Acid," P. Slosar et al., CHEMagazin, Vol. 9, No. 6, pp. 8-11 (1999), the disclosure of which is totally incorporated herein by reference, discloses yellow pigments based on H-pyridone and esters of aminoterephthalic acid wherein the color strength, brilliance (purity), and deepening of greenish shade were the larger the smaller alkyl is in the carbalkoxy group in o-position towards the azo group and the greater alkyl is in the carbalkoxy group in m-position towards the azo group.

Of potential background interest with respect to the present invention are the following references: U.S. Pat. Nos. 5,919,839; 5,827,918; 4,889,560; 5,372,852; "Synthesis, Morphology, and Optical Properties of Tetrahedral Oligo (phenylenevinylene) Materials," S. Wang et al., J. Am. Chem. Soc., Vol. 120, p. 5695 (2000); "Syntheses of Amphiphilic Diblock Copolymers Containing a Conjugated Block and Their Self-Assembling Properties," H. Wang et al., J. Am. Chem. Soc., Vol. 122, p. 6855 (2000); "Crystal Engineering of Conjugated Oligomers and the Spectral Signature of π Stacking in Conjugated Oligomers and Polymers," A. Koren et al., Chem. Mater., Vol. 12, p. 1519 (2000); "The Chemistry of Isatoic Anhydride," G. M. Coppola, Synthesis, p. 505 (1980); "Isatoic Anhydride. IV. Reactions with Various Nucleophiles," R. P. Staiger et al., J. Org. Chem., Vol. 24, p. 1214 (1959); "Investigation of the Reaction Conditions for the Synthesis of 4,6-Disubstituted-3-cyano-2-pyridones and 4-Methyl-3-cyano-6-hydroxy-2-pyridone, " D. Z. Mijin et al., J. Serb. Chem. Soc., Vol. 59, No. 12, p. 959 (1994); "Synthesis of Isoquinoline Alkaloids. II. The Synthesis and Reactions of 4-Methyl-3-pyridinecarboxaldehyde and Other 4-Methyl-3-substituted Pyridines," J. M. Bobbitt et al., J. Org. Chem., Vol. 25, p. 560 (1960); "Synthesis and Dyeing Characteristics of 5-(4-Arylazophenyl) azo-3-cyano-4-methyl-6-hydroxy-2-pyridones, " J. Kanhere et al., Indian Journal of Textile Research, Vol. 13, p. 213 (1988); "Synthesis of Some Pyridone Azo Dyes from 1-Substituted 2-Hydroxy-6-pyridone Derivatives and their Colour Assessment," C. Chen et al., Dyes and Pigments, Vol. 15, p. 69 (1991); German Patent Publication DE 3543360; Japanese Patent Publication JP 2001214083; German Patent Publication DE 3505899; Indian Patent Publication 147527; European Patent Publication EP 0 524 637; European Patent Publication EP 0 529 282; European Patent Publication EP 0 083 553; Japanese Patent Publication JP 2000 62327; Japanese Patent Publication JP 85152563; "Synthesis of 3-Cyano-6-hydroxy-5-(2-(perfluoroalkyl)phenylazo)-2-pyridones and their Application for Dye Diffusion Thermal Transfer Printing," Bull. Chem. Soc. Jpn., 1993, Vol. 66, Iss. 6, Pp. 1790-4; European Patent Publication 0 844 287; European Patent Publication 0 404 493; U.S. Pat. Nos. 5,902,841; 5,621,022; 5,006,170; Chinese Patent Publication CN 1115773; German Patent Publication DE 3447117; Japanese Patent Publication JP 5331382; Japanese Patent Publication JP 63210169; Japanese Patent Publication JP 63199764; Japanese Patent Publication JP 63199763; Japanese Patent Publication JP 63199762; Japanese Patent Publication JP 63199761; Japanese Patent Publication JP 63199760; Japanese Patent Publication JP 63071392; Japanese Patent Publication JP 61181865; Japanese Patent Publication JP 61036366; Japanese Patent Publication JP 60152563; Japanese Patent Publication JP 60112862; Japanese Patent Publication JP 60112861; Japanese Patent Publication JP 58149953; Japanese Patent Publication JP 56092961; Japanese Patent Publication JP 56026957; Japanese Patent Publication JP 55099958; Japanese Patent Publication JP 96 11443 (JP8011443); Japanese Patent Publication JP 93169849 (JP5169849); Japanese Patent Publication JP 93 51536 (JP5051536); Japanese Patent Publication JP 90185569 (JP2185569); European Patent Publication 0 319 234; European Patent Publication 0 314 002; European Patent Publication 0 302 401; U.S. Pat. No. 4,734,349; Japanese Patent Publication JP 87290762 (JP62290762); Japanese Patent Publication JP 86244595 (JP61244595); Indian Patent Publication IN 147868; Spanish Patent Publication 475254 (Equivalent of Italian Patent Publication IT 1088895); German Patent Publication DE 2727809; "Colour and Constitution of Azo Dyes Derived from 2-Thioalkyl-4, 6-Diaminopyrimidines and 3-Cyano-1,4-dimethyl-6-hydroxy-2-pyridone as Coupling Components," L. Cheng et al., Dyes and Pigments, Vol. 7, No. 5, pp. 373-388 (1986); European Patent Publication 1 168 046; U.S. Pat. No. 4,644,058; Japanese Patent Publication JP 63039380; Japanese Patent Publication JP 54102328; Japanese Patent Publication JP 54070337; "Trends in Modern Dye Chemistry. Part 10," N. R. Ayyangar and K. V. Srinivasan, Colourage, Vol. 37, No. 2, pp. 29-30 (Jan. 16, 1990); European Patent Publication EP 0 172 283; Japanese Patent Publication JP 05169854; Japanese Patent Publication JP 04292988; Japanese Patent Publication JP 63161060; Japanese Patent Publication JP 61244595; Korean Patent Publication KR 119563; European Patent Publication EP 0 142 863; European Patent Publication EP 0 023 770; Japanese Patent Publication JP 00239549 (JP2000239549); Japanese Patent Publication JP 11269402; Japanese Patent Publication JP 09041267; Japanese Patent Publication JP 08039941; U.S. Pat. No. 4,994,564; Japanese Patent Publication JP 06294909; Japanese Patent Publication JP 06122829; Japanese Patent Publication JP 05255602; Japanese Patent Publication JP 05051536; Japanese Patent Publication JP 04235093; European Patent Publication EP 0 468 647; European Patent Publication EP 0 063 275; U.S. Pat. No. 4,216,145; and German Patent Publication DE 2606506; the disclosures of each of which are totally incorporated herein by reference.

While known compositions and processes are suitable for their intended purposes, a need remains for new yellow colorant compositions. In addition, a need remains for yellow colorant compositions particularly suitable for use in phase change inks. Further, a need remains for yellow colorants with desirable thermal stability. Additionally, a need remains for yellow colorants that exhibit minimal undesirable discoloration when exposed to elevated temperatures. There is also a need for yellow colorants that exhibit a desirable brilliance. In addition, there is a need for yellow colorants that exhibit a desirable hue. Further, there is a need for yellow colorants that are of desirable chroma. Additionally, there is a need for yellow colorants that have desirably high lightfastness characteristics. A need also remains for yellow colorants that have a desirably pleasing color. In addition, there is a need for yellow colorants that exhibit desirable solubility characteristics in phase change ink carrier compositions. Further, a need remains for yellow colorants that enable phase change inks to be jetted at temperatures of over 135° C. while maintaining thermal stability. Additionally, a need remains for yellow colorants that enable phase change inks that generate images with low pile height. There is also a need for yellow colorants that enable phase change inks that generate images that approach lithographic thin image quality. In addition, there is a need for yellow colorants that exhibit oxidative stability. Further, there is a need for yellow colorants that do not precipitate from phase change ink carriers. Additionally, there is a need for yellow colorants that do not, when included in phase change inks, diffuse into adjacently printed inks of different colors. A need also remains for yellow colorants that do not leach from media such as phase change ink carriers into tape adhesives, paper, or the like. In addition, a need remains for yellow colorants that, when incorporated into phase change inks, do not lead to clogging of a phase change ink jet printhead. Further, there is a need for yellow colorants that enable phase change inks that generate images with sharp edges that remain sharp over time. Additionally, there is a need for yellow colorants that enable phase change inks that generate images which retain their high image quality in warm climates. Further, there is a need for yellow colorants that enable phase change inks that generate images of desirably high optical density. Additionally, there is a need for yellow colorants that, because of their good solubility in phase change ink carriers, enable the generation of images of low pile height without the loss of desirably high optical density. A need also remains for yellow colorants that enable the use of substantially reduced amounts of colorant in, for example, an ink without decreasing the color and the spectral properties (L*a*b*) of the ink or jeopardizing the optical density or color of the prints generated with the ink. In addition, a need remains for yellow colorants that enable cost-effective inks.

SUMMARY

Disclosed herein is a compound comprising three or more moieties of the formula

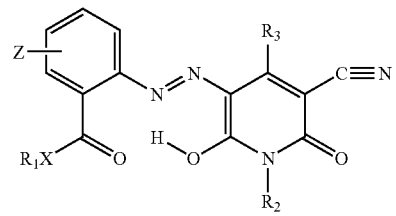

wherein (A) each $R_1$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, or (vi) a siloxy group, (B) each $R_2$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, (vi) a siloxy group, or (vii) a group of the formula

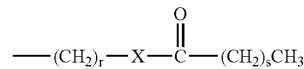

wherein r and s are each, independently of the other, integers representing a number of repeat —$CH_2$— groups, (C) each $R_3$, independently of the others, is (i) an alkyl group, (ii) an aryl group, (iii) an arylalkyl group, or (iv) an alkylaryl group, (D) each X, independently of the others, is (i) a direct bond, (ii) an oxygen atom, (iii) a sulfur atom, (iv) a group of the formula —$NR_{40}$— wherein $R_{40}$ is a hydrogen atom, an alkyl group, an aryl group, an arylalkyl group, or an alkylaryl group, or (v) a group of the formula —$CR_{50}R_{60}$— wherein $R_{50}$ and $R_{60}$ each, independently of the other, is a hydrogen atom, an alkyl group, an aryl group, an arylalkyl group, or an alkylaryl group, and (E) each Z, independently of the others, is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

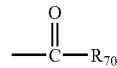

wherein $R_{70}$ is an alkyl group, an aryl group, an arylalkyl group, an alkylaryl group, a silyl group, or a siloxy group, (ix) a sulfonyl group of the formula —$SO_2R_{80}$ wherein $R_{80}$ is a hydrogen atom, an alkyl group, an aryl group, an arylalkyl group, an alkylaryl group, a silyl group, or a siloxy group, or (x) a phosphoryl group of the formula —$PO_3R_{90}$ wherein $R_{90}$ is a hydrogen atom, an alkyl group, an aryl group, an arylalkyl group, an alkylaryl group, a silyl group, or a siloxy group; said moieties being bonded to a central atom, monomeric group of atoms, oligomer, or polymer. Also disclosed herein is a phase change ink comprising a phase change ink carrier and a colorant compound comprising three or more moieties of the formula

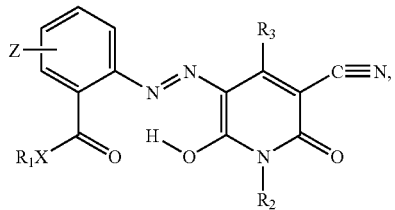

said moieties being bonded to a central atom, monomeric group of atoms, oligomer, or polymer.

DETAILED DESCRIPTION

Disclosed herein are colorant compounds containing three or more moieties of the formula

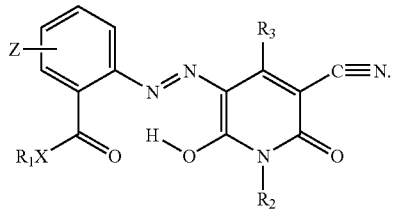

These moieties are linked by a central atom or monomeric group of atoms or bonded to an oligomer or polymer. For example, a moiety of this formula can be linked to a central atom or group of atoms through the $R_1$ group, in which case the $R_1$ group is divalent or polyvalent, as follows:

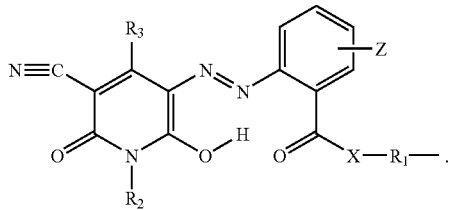

Or, for example, a moiety of this formula can be linked to a central atom or group of atoms through the $R_2$ group, in which case the $R_2$ group is divalent or polyvalent, as follows:

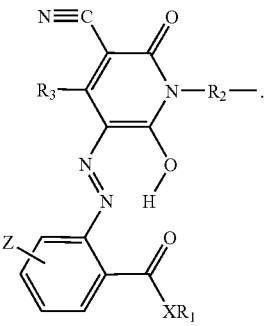

The moieties can be bonded to a single central atom, with four examples of such types of compounds being

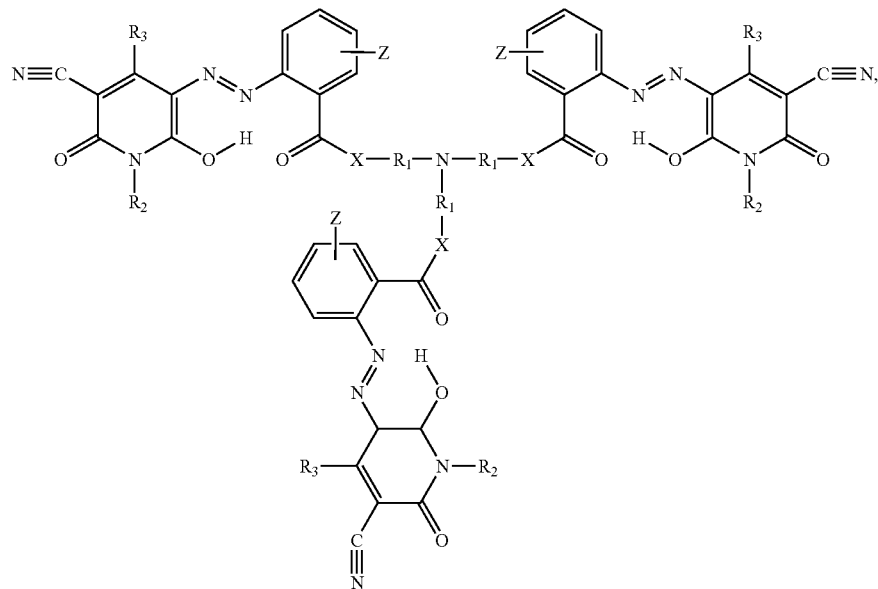

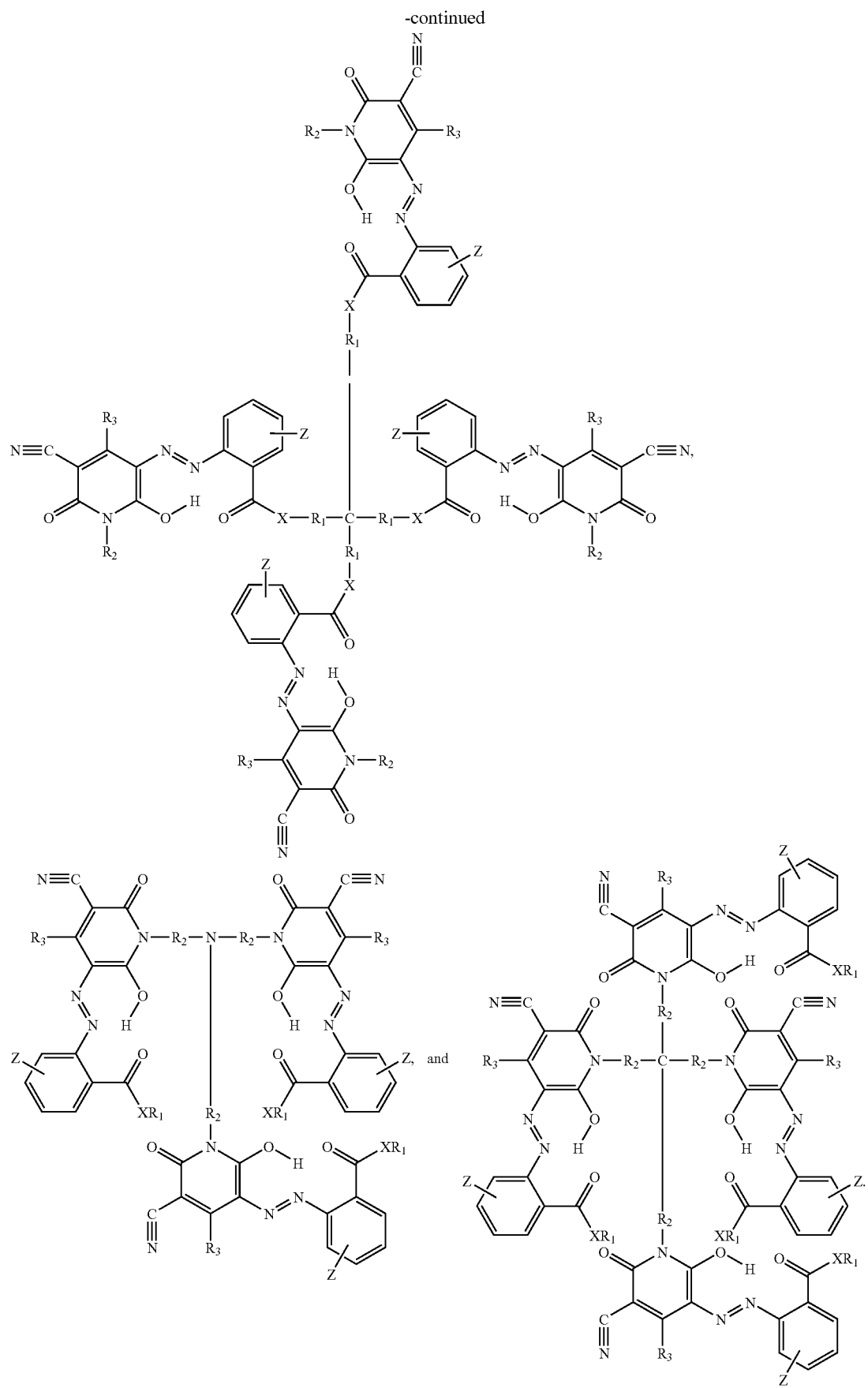

The moieties can also be linked to different atoms in a monomeric central group of atoms. The central group of atoms can be a small molecule, such as ethylene or propylene or benzene, or, if desired, a larger molecule. In addition, the central group of atoms can be an oligomer or a polymer. The central molecule can be selected for compatibility with the other components with which the colorant is to be admixed, if any, or for the purpose for which the colorant is to be used. For example, when the colorant is to be used in a phase change ink, in one specific embodiment polymers or oligomers with about 20 repeat monomer units or fewer can be employed. In another embodiment, polymers or oligomers with from about 10 to about 20 repeat monomer units are employed.

The chromogene moieties are of the general formula

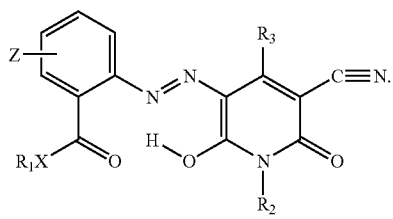

In this formula, each $R_1$, independently of the other $R_1$ groups in other chromogene moieties attached to the central atom or group of atoms, is (i) an alkyl or alkylene group (including linear, branched, saturated, unsaturated, cyclic, unsubstituted, and substituted alkyl and alkylene groups, and wherein hetero atoms, such as oxygen, nitrogen, sulfur, silicon, phosphorus, and the like either may or may not be present in the alkyl or alkylene group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (ii) an aryl or arylene group (including unsubstituted and substituted aryl and arylene groups, and wherein hetero atoms, such as oxygen, nitrogen, sulfur, silicon, phosphorus, and the like either may or may not be present in the aryl or arylene group), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, (iii) an arylalkyl or arylalkylene group (including unsubstituted and substituted arylalkyl and arylalkylene groups, and wherein hetero atoms, such as oxygen, nitrogen, sulfur, silicon, phosphorus, and the like either may or may not be present in either or both of the aryl portion and the alkyl portion of the arylalkyl or arylalkylene group), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (iv) an alkylaryl or alkylarylene group (including unsubstituted and substituted alkylaryl and alkylarylene groups, and wherein hetero atoms, such as oxygen, nitrogen, sulfur, silicon, phosphorus, and the like either may or may not be present in either or both of the aryl portion and the alkyl portion of the alkylaryl or alkylarylene group), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (v) a silyl or silylene group (including unsubstituted and substituted silyl and silylene groups, and including polysilylene groups, in one embodiment with from 2 to about 100 repeat silylene units, although the number of repeat units can be outside of this range), or (vi) a siloxy group (including unsubstituted and substituted siloxy groups, and including polysiloxane groups, in one embodiment with from 2 to about 200 repeat siloxane units, although the number of repeat units can be outside of this range), wherein the substituents on the substituted alkyl, alkylene, aryl, arylene, arylalkyl, arylalkylene, alkylaryl, alkylarylene, silyl, silylene, and siloxane groups can be (but are not limited to) hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silyl, silylene, and siloxy groups can also be alkyl groups, aryl groups, arylalkyl groups, and alkylaryl groups, wherein two or more substituents can be joined together to form a ring. Since hetero atoms can be present in the alkyl, alkylene, aryl, arylene, arylalkyl, arylalkylene, alkylaryl, and alkylarylene groups, these groups also include alkoxy, alkyleneoxy, aryloxy, aryleneoxy, arylalkyloxy, arylalkyleneoxy, alkylaryloxy, alkylaryleneoxy, and the like; in addition, these groups also include polyalkyleneoxy groups, including (but not limited to) those wherein the alkyl portion of the repeat alkyleneoxy group has from 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups is from about 2 to about 50, polyaryleneoxy groups, including (but not limited to) those wherein the aryl portion of the repeat aryleneoxy group has from about 6 to about 14 carbon atoms, such as a polyphenyleneoxy group, a polynaphthaleneoxy group, a polyphenanthreneoxy group, or the like, and wherein the number of repeat aryleneoxy groups is from about 2 to about 20, polyarylalkyleneoxy groups, including (but not limited to) those wherein the arylalkyl portion of the repeat arylalkyleneoxy group has from about 7 to about 50 carbon atoms, such as a polybenzyleneoxy group, a polyphenylethyleneoxy group, or the like, and wherein the number of repeat arylalkyleneoxy groups is from about 2 to about 20, polyalkylaryleneoxy groups, including (but not limited to) those wherein the alkylaryl portion of the repeat alkylaryleneoxy group has from about 7 to about 50 carbon atoms, such as a polytolueneoxy group or the like, and wherein the number of repeat alkylaryleneoxy groups is from about 2 to about 20, and the like. Further, since hetero atoms can be present in these groups, these groups also include heterocyclic groups.

Some specific examples of suitable monovalent $R_1$ groups include (but are not limited to) methyl, of the formula —$CH_3$, ethyl, of the formula —$C_2H_5$, n-octyl, of the formula —$(CH_2)_7CH_3$, stearyl, of the formula —$(CH_2)_{17}CH_3$, menthyl, of the formula

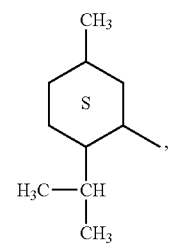

wherein the "S" indicates that the ring is saturated as opposed to being aromatic, branched saturated hydrocarbon groups containing 18 carbon atoms, of the general formula

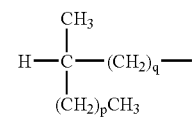

wherein q is an integer of from about 10 to about 15, p is an integer of from 0 to about 3, and the sum of p+q=15, such as isostearyl, oleyl, of the formula

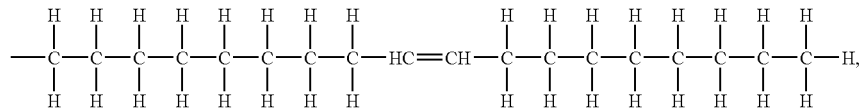

2-octyldodecyl, of the formula

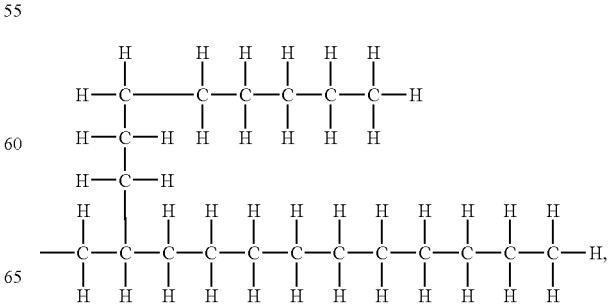

cholesteryl, of the formula

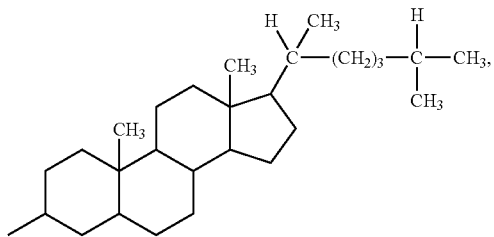

abietyl, including groups of the formula

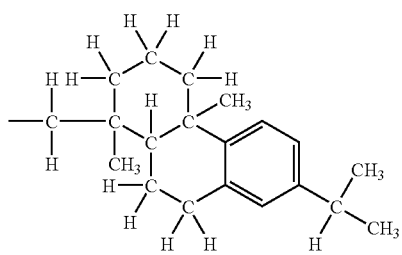

as well as hydrogenated and dehydrogenated isomers of the above formula that are also derivatives of the rosin-derived natural product abietic acid, such as didehydroabietyl and the like, 2-ethylhexyl, of the formula

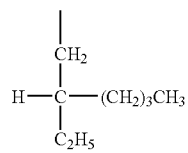

(1-oxypropyl)-2-octyldodecane, of the formula

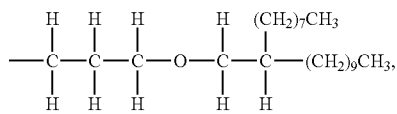

and the like. Some specific examples of suitable divalent $R_1$ groups include (but are not limited to) n-hexanediyl, of the formula —$(CH_2)_6$—, n-octanediyl, of the formula —$(CH_2)_8$—, n-decanediyl, of the formula —$(CH_2)_{10}$—, n-dodecanediyl, of the formula —$(CH_2)_{12}$—, 3-methyl-1,5-pentanediyl, of the formula

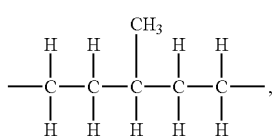

1,4-cyclohexanedimethylene, of the formula (which is not intended to be limited to any particular stereochemistry and includes all cis and trans isomers)

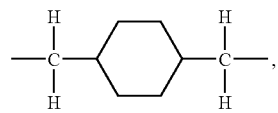

4,4'-isopropylidenedicyclohexanediyl, of the formula (which is not intended to be limited to any particular stereochemistry and includes all cis and trans isomers)

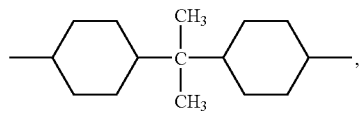

4,4'-bicyclohexyanediyl, of the formula (which is not intended to be limited to any particular stereochemistry and includes all cis and trans isomers)

a branched alkylene group having 36 carbon atoms, including isomers of the formula

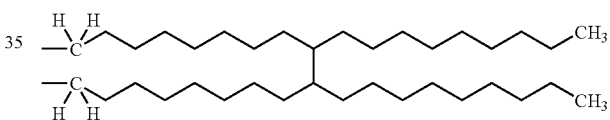

and other branched alkylene isomers (which may include unsaturations and cyclic groups), 4,8-bis(methylene)tricyclo($5210^{2,6}$)decanediyl, of the formula (which is not intended to be limited to any particular stereochemistry and includes all cis and trans isomers)

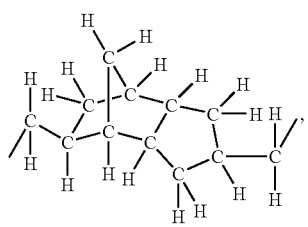

and the like.

In the chromogene moieties of the above formula, each $R_2$, independently of the other $R_2$ groups in other chromogene moieties attached to the central atom or group of atoms, is (i) an alkyl or alkylene group (including linear, branched, saturated, unsaturated, cyclic, unsubstituted, and substituted alkyl and alkylene groups, and wherein hetero atoms, such as oxygen, nitrogen, sulfur, silicon, phosphorus, and the like either may or may not be present in the alkyl or alkylene group), in one embodiment with at least 1 carbon atom, in another embodiment with at least about 8 carbon atoms, in yet another embodiment with at least about 10 carbon atoms, in still another embodiment with at least about 12 carbon atoms, in another embodiment with at least about 14 carbon atoms, in yet another embodiment with at least about 16 carbon atoms, in still another embodiment with at least about 18 carbon atoms, in another embodiment with at least about 20 carbon atoms, in yet another embodiment with at least about 22 carbon atoms, in still another embodiment with at least about 24 carbon atoms, in another embodiment with at least about 26 carbon atoms, in yet another embodiment with at least about 28 carbon atoms, in still another embodiment with at least about 30 carbon atoms, in another embodiment with at least about 32 carbon atoms, in yet another embodiment with at least about 34 carbon atoms, and in still another embodiment with at least about 36 carbon atoms, and in one embodiment with no more than about 200 carbon atoms, in another embodiment with no more than about 100 carbon atoms, in yet another embodiment with no more than about 75 carbon atoms, in still another embodiment with no more than about 60 carbon atoms, in another embodiment with no more than about 50 carbon atoms, and in yet another embodiment with no more than about 40 carbon atoms, although the number of carbon atoms can be outside of these ranges, (ii) an aryl or arylene group (including unsubstituted and substituted aryl and arylene groups, and wherein hetero atoms, such as oxygen, nitrogen, sulfur, silicon, phosphorus, and the like either may or may not be present in the aryl or arylene group), in one embodiment with at least about 6 carbon atoms, in another embodiment with at least about 10 carbon atoms, in yet another embodiment with at least about 13 carbon atoms, in still another embodiment with at least about 14 carbon atoms, in another embodiment with at least about 16 carbon atoms, in yet another embodiment with at least about 17 carbon atoms, in still another embodiment with at least about 18 carbon atoms, in another embodiment with at least about 19 carbon atoms, in yet another embodiment with at least about 20 carbon atoms, in still another embodiment with at least about 21 carbon atoms, in another embodiment with at least about 22 carbon atoms, and in yet another embodiment with at least about 23 carbon atoms, and in one embodiment with no more than about 100 carbon atoms, in another embodiment with no more than about 75 carbon atoms, and in yet another embodiment with no more than about 50 carbon atoms, although the number of carbon atoms can be outside of these ranges, (iii) an arylalkyl or arylalkylene group (including unsubstituted and substituted arylalkyl and arylalkylene groups, and wherein hetero atoms, such as oxygen, nitrogen, sulfur, silicon, phosphorus, and the like either may or may not be present in either or both of the aryl portion and the alkyl portion of the arylalkyl or arylalkylene group), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (iv) an alkylaryl or alkylarylene group (including unsubstituted and substituted alkylaryl and alkylarylene groups, and wherein hetero atoms, such as oxygen, nitrogen, sulfur, silicon, phosphorus, and the like either may or may not be present in either or both of the aryl portion and the alkyl portion of the alkylaryl or alkylarylene group), in one embodiment with at least about 7 carbon atoms, in another embodiment with at least about 8 carbon atoms, in another embodiment with at least about 10 carbon atoms, in yet another embodiment with at least about 12 carbon atoms, in still another embodiment with at least about 14 carbon atoms, in another embodiment with at least about 16 carbon atoms, in yet another embodiment with at least about 18 carbon atoms, in still another embodiment with at least about 20 carbon atoms, in another embodiment with at least about 22 carbon atoms, in yet another embodiment with at least about 24 carbon atoms, in still another embodiment with at least about 26 carbon atoms, in another embodiment with at least about 28 carbon atoms, in yet another embodiment with at least about 30 carbon atoms, in still another embodiment with at least about 32 carbon atoms, in another embodiment with at least about 34 carbon atoms, in yet another embodiment with at least about 36 carbon atoms, in another embodiment with at least about 38 carbon atoms, in yet another embodiment with at least about 40 carbon atoms, and in still another embodiment with at least about 42 carbon atoms, and in one embodiment with no more than about 200 carbon atoms, in another embodiment with no more than about 100 carbon atoms, and in yet another embodiment with no more than about 44 carbon atoms, although the number of carbon atoms can be outside of these ranges, (v) a silyl or silylene group (including unsubstituted and substituted silyl and silylene groups, and including polysilylene groups, in one embodiment with from 2 to about 100 repeat silylene units, although the number of repeat units can be outside of this range), (vi) a siloxy group (including unsubstituted and substituted siloxane groups, and including polysiloxane groups, in one embodiment with from 2 to about 200 repeat siloxane units, although the number of repeat units can be outside of this range), or (vii) a group of the formula

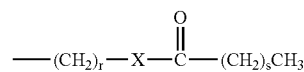

wherein r is an integer representing the number of repeat —$CH_2$— groups, in one embodiment being at least 1, in another embodiment at least about 5, and in yet another embodiment at least about 10, and in one embodiment being no more than about 100, in another embodiment no more than about 50, and in yet another embodiment no more than about 25, although the value of r can be outside of these ranges, and wherein s is an integer representing the number of repeating —$CH_2$— groups, in one embodiment being at least 1, in another embodiment at least about 5, and in yet another embodiment at least about 10, and in one embodiment being no more than about 100, in another embodiment no more than about 50, and in yet another embodiment no more than about 25, although the value of s can be outside of these ranges, wherein the substituents on the substituted alkyl, alkylene, aryl, arylene, arylalkyl, arylalkylene, alkylaryl, alkylarylene, silyl, silylene, and siloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silyl and siloxy groups can also be alkyl groups, aryl groups, arylalkyl groups, and alkylaryl groups, wherein two or more substituents can be joined together to form a ring. Since hetero atoms can be present in the alkyl, alkylene, aryl, arylene, arylalkyl, arylalkylene, alkylaryl, and alkylarylene groups, these groups also include alkoxy, alkyleneoxy, aryloxy, aryleneoxy, arylalkyloxy, arylalkyleneoxy, alkylaryloxy, alkylaryleneoxy, and the like; in addition, these groups also include polyalkyleneoxy groups, including (but not limited to) those wherein the alkyl portion of the repeat alkyleneoxy group has from 1 to about 12 carbon atoms, although the number of carbon atoms can be outside of these ranges, such as a polyethyleneoxy group, a polypropyleneoxy group, a polybutyleneoxy group, or the like, and wherein the number of repeat alkyleneoxy groups is from about 2 to about 50, polyaryleneoxy groups, including (but not limited to) those wherein the aryl portion of the repeat aryleneoxy group has from about 6 to about 14-carbon atoms, such as a polyphenyleneoxy group, a polynaphthaleneoxy group, a polyphenanthreneoxy group, or the like, and wherein the number of repeat aryleneoxy groups is from about 2 to about 20, polyarylalkyleneoxy groups, including (but not limited to) those wherein the arylalkyl portion of the repeat arylalkyleneoxy group has from about 7 to about 50 carbon atoms, such as a polybenzyleneoxy group, a polyphenylethyleneoxy group, or the like, and wherein the number of repeat arylalkyleneoxy groups is from about 2 to about 20, polyalkylaryleneoxy groups, including (but not limited to) those wherein the alkylaryl portion of the repeat alkylaryleneoxy group has from about 7 to about 50 carbon atoms, such as a polytolueneoxy group or the like, and wherein the number of repeat alkylaryleneoxy groups is from about 2 to about 20, and the like. Further, since hetero atoms can be present in these groups, these groups also include heterocyclic groups.

Some specific examples of suitable monovalent $R_2$ groups include (but are not limited to) ethyl, of the formula —$CH_2CH_3$, n-butyl, of the formula —$(CH_2)_3CH_3$, n-octyl, of the formula —$(CH_2)_7CH_3$, n-decyl, of the formula —$(CH_2)_9CH_3$, n-dodecyl, of the formula —$(CH_2)_{11}CH_3$, n-tetradecyl, of the formula —$(CH_2)_{13}CH_3$, cetyl, of the formula —$(CH_2)_{15}CH_3$, stearyl, of the formula —$(CH_2)_{17}CH_3$, 2-ethylhexyl, of the formula

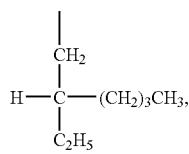

abietyl, including groups of the formula

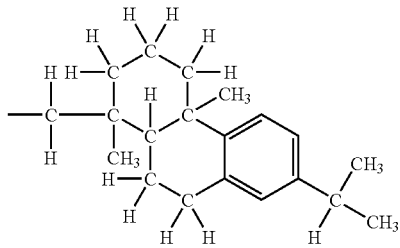

as well as hydrogenated and dehydrogenated isomers of the above formula that are also derivatives of the rosin-derived natural product abietic acid, such as didehydroabietyl and the like, 3-propyl octadecanoyl, of the formula

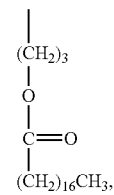

2,2-dimethyl-1,3-dioxolane-4-methylene, of the formula

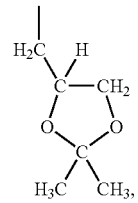

and the like. Some specific examples of suitable divalent $R_2$ groups include (but are not limited to) n-hexanediyl, of the formula —$(CH_2)_6$—, n-octanediyl, of the formula —$(CH_2)_8$—, n decanediyl, of the formula —$(CH_2)_{10}$—, n-dodecanediyl, of the formula —$(CH_2)_{12}$—, 2-methyl-1,5-pentanediyl, of the formula

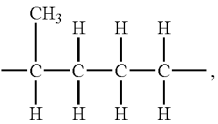

butane-1,4-di(oxypropyl), of the formula —$CH_2CH_2CH_2$—O—$CH_2CH_2CH_2CH_2$—O—$CH_2CH_2CH_2$—, 1,3-cyclohexanedimethylene, of the formula (which is not intended to be limited to any particular stereochemistry and includes all cis and trans isomers)

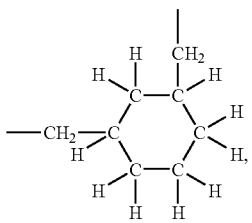

dicyclohexylmethane-4,4'-diyl, of the formula (which is not intended to be limited to any particular stereochemistry and includes all cis and trans isomers)

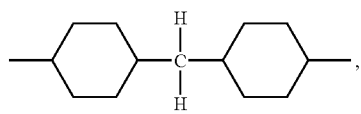

4,8-bis(methylene)tricyclo(5210$^{2,6}$)decanediyl, of the formula (which is not intended to be limited to any particular stereochemistry and includes all cis and trans isomers)

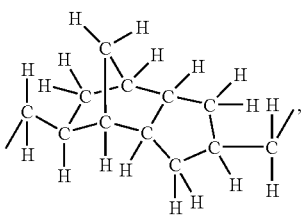

a branched alkylene group having 36 carbon atoms, including isomers of the formula

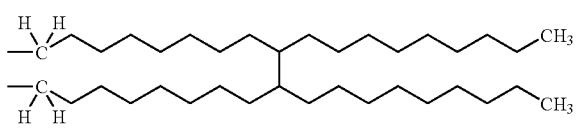

and other branched isomers (which may include unsaturations and cyclic groups), a branched alkylene diester group having 36 carbon atoms, including isomers of the formula

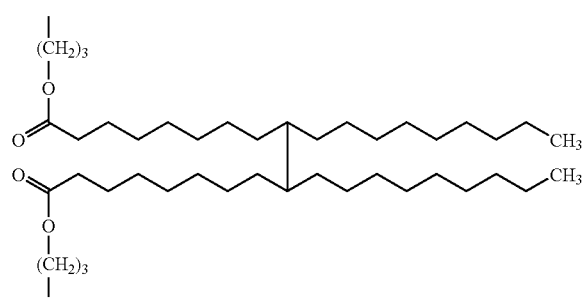

and other branched isomers (which may include unsaturations and cyclic groups), and the like.

In the chromogene moieties of the above formula, each $R_3$, independently of the other $R_3$ groups in other chromogene moieties attached to the central atom or group of atoms, is (i) an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 100 carbon atoms, in another embodiment with no more than about 10 carbon atoms, and in yet another embodiment with no more than about 5 carbon atoms, although the number of carbon atoms can be outside of these ranges, (ii) an aryl group (including unsubstituted and substituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 100 carbon atoms, and in another embodiment with no more than about 10 carbon atoms, although the number of carbon atoms can be outside of these ranges, (iii) an arylalkyl group (including unsubstituted and substituted arylalkyl groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 100 carbon atoms, and in another embodiment with no more than about 10 carbon atoms, although the number of carbon atoms can be outside of these ranges, or (iv) an alkylaryl group (including unsubstituted and substituted alkylaryl groups, and wherein hetero atoms, such as oxygen, nitrogen, sulfur, silicon, phosphorus, and the like either may or may not be present in either or both of the aryl portion and the alkyl portion of the alkylaryl group), in one embodiment with at least about 7 carbon atoms, and in one embodiment with no more than about 100 carbon atoms, and in another embodiment with no more than about 10 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein two or more substituents can be joined together to form a ring. Since hetero atoms can be present in the alkyl, aryl, arylalkyl, and alkylaryl groups, these groups also include alkoxy, aryloxy, arylalkyloxy, alkylaryloxy, and the like; in addition, these groups also include polyalkyleneoxy groups, polyaryleneoxy groups, polyarylalkyleneoxy groups, polyalkylaryleneoxy groups, and the like. Further, since hetero atoms can be present in these groups, these groups also include heterocyclic groups.

Some specific examples of suitable $R_3$ groups include methyl (—$CH_3$), linear alkyl groups of the formula —$(CH_2)_C CH_3$ wherein c is an integer of 1, 2, 3, 4, 5, 6, 7, 8, or 9, and the like.

In the chromogene moieties of the above formula, each X, independently of the other X moieties in other chromogene moieties attached to the central atom or group of atoms, is (i) a direct bond, (ii) an oxygen atom, (iii) a sulfur atom, (iv) a group of the formula —$NR_{40}$— wherein $R_{40}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, in another embodiment with at least about 2 carbon atoms, and in yet another embodiment with at least about 4 carbon atoms, and in one embodiment with no more than about 50 carbon atoms, in another embodiment with no more than about 20 carbon atoms, and in yet another embodiment with no more than about 12 carbon atoms, although the number of carbon atoms can be outside of these ranges, an aryl group (including substituted and unsubstituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 50 carbon atoms, in another embodiment with no more than about 20 carbon atoms, and in yet another embodiment with no more than about 10 carbon atoms, although the number of carbon atoms can be outside of these ranges, an arylalkyl group (including substituted and unsubstituted arylalkyl groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 100 carbon atoms, in another embodiment with no more than about 50 carbon atoms, and in yet another embodiment with no more than about 20 carbon atoms, although the number of carbon atoms can be outside of these ranges, or an alkylaryl group (including substituted alkylaryl and unsubstituted groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 100 carbon atoms, in another embodiment with no more than about 50 carbon atoms, and in yet another embodiment with no more than about 20 carbon atoms, although the number of carbon atoms can be outside of these ranges, or (v) a group of the formula —$CR_{50}R_{60}$— wherein $R_{50}$ and $R_{60}$ each, independently of the other, is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, in another embodiment with at least about 2 carbon atoms, and in yet another embodiment with at least about 4 carbon atoms, and in one embodiment with no more than about 50 carbon atoms, in another embodiment with no more than about 20 carbon atoms, and in yet another embodiment with no more than about 12 carbon atoms, although the number of carbon atoms can be outside of these ranges, an aryl group (including substituted and unsubstituted aryl groups, and wherein hetero atoms, such as oxygen, nitrogen, sulfur, silicon, phosphorus, and the like either may or may not be present in the aryl group), in one embodiment with at least about 6 carbon atoms, and in one-embodiment with no more than about 50 carbon atoms, in another embodiment with no more than about 20 carbon atoms, and in yet another embodiment with no more than about 10 carbon atoms, although the number of carbon atoms can be outside of these ranges, an arylalkyl group (including substituted and unsubstituted arylalkyl groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 100 carbon atoms, in another embodiment with no more than about 50 carbon atoms, and in yet another embodiment with no more than about 20 carbon atoms, although the number of carbon atoms can be outside of these ranges, or an alkylaryl group (including substituted and unsubstituted alkylaryl groups, and wherein hetero atoms, such as oxygen, nitrogen, sulfur, silicon, phosphorus, and the like either may or may not be present in either or both of the aryl portion and the alkyl portion of the alkylaryl group), in one embodiment with at least about 7 carbon atoms, and in one embodiment with no more than about 100 carbon atoms, in another embodiment with no more than about 50 carbon atoms, and in yet another embodiment with no more than about 20 carbon atoms, although the number of carbon atoms can be outside of these ranges, wherein the substituents on the substituted alkyl, aryl, arylalkyl, and alkylaryl groups can be (but are not limited to) hydroxy groups, halogen atoms, amine groups, imine groups, ammonium groups, pyridine groups, pyridinium groups, ether groups, aldehyde groups, ester groups, amide groups, carbonyl groups, thiocarbonyl groups, sulfate groups, sulfonate groups, sulfide groups, sulfoxide groups, phosphine groups, phosphonium groups, phosphate groups, nitrile groups, mercapto groups, nitro groups, nitroso groups, sulfone groups, acyl-groups, acid anhydride groups, azide groups, cyanato groups, isocyanato groups, thiocyanato groups, isothiocyanato groups, mixtures thereof, and the like, wherein two or more substituents can be joined together to form a ring. Since hetero atoms can be present in the alkyl, aryl, arylalkyl, and alkylaryl groups, these groups also include alkoxy, aryloxy, arylalkyloxy, alkylaryloxy, and the like; in addition, these groups also include polyalkyleneoxy groups, polyaryleneoxy groups, polyarylalkyleneoxy groups, polyalkylaryleneoxy groups, and the like. Further, since hetero atoms can be present in these groups, these groups also include heterocyclic groups.

In the chromogene moieties of the above formula, each Z, independently of the other Z moieties in other chromogene moieties attached to the central atom or group of atoms, is (i) a hydrogen atom, (ii) a halogen atom, including fluorine, chlorine, bromine, and iodine, (iii) a nitro group, (iv) an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 50 carbon atoms, in another embodiment with no more than about 20 carbon atoms, and in yet another embodiment with no more than about 10 carbon atoms, although the number of carbon atoms can be outside of these ranges, (v) an aryl group (including substituted and unsubstituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 50 carbon atoms, in another embodiment with no more than about 14 carbon atoms, and in yet another embodiment with no more than about 10 carbon atoms, although the number of carbon atoms can be outside of these ranges, (vi) an arylalkyl group (including substituted and unsubstituted arylalkyl groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, (vii) an alkylaryl group (including substituted and unsubstituted alkylaryl groups, and wherein hetero atoms, such as oxygen, nitrogen, sulfur, silicon, phosphorus, and the like either may or may not be present in either or both of the aryl portion and the alkyl portion of the alkylaryl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, (viii) a group of the formula $$-\overset{O}{\underset{\|}{C}}-R_{70}$$

wherein $R_{70}$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 50 carbon atoms, in another embodiment with no more than about 20 carbon atoms, and in yet another embodiment with no more than about 10 carbon atoms, although the number of carbon atoms can be outside of these ranges, an aryl group (including substituted and unsubstituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 50 carbon atoms, in another embodiment with no more than about 20 carbon atoms, and in yet another embodiment with no more than about 14 carbon atoms, although the number of carbon atoms can be outside of these ranges, an arylalkyl group (including substituted and unsubstituted arylalkyl groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, an alkylaryl group (including substituted and unsubstituted alkylaryl groups, and wherein hetero atoms, such as oxygen, nitrogen, sulfur, silicon, phosphorus, and the like either may or may not be present in either or both of the aryl portion and the alkyl portion of the alkylaryl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, a silyl group (including unsubstituted and substituted silyl groups, and including polysilylene groups, in one embodiment with from 2 to about 100 repeat silylene units, although the number of repeat units can be outside of this range), or a siloxy group (including unsubstituted and substituted siloxy groups, and including polysiloxane groups, in one embodiment with from 2 to about 200 repeat siloxane units, although the number of repeat units can be outside of this range), (ix) a sulfonyl group of the formula $-SO_2R_{80}$, wherein $R_{80}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 50 carbon atoms, in another embodiment with no more than about 20 carbon atoms, and in yet another embodiment with no more than about 10 carbon atoms, although the number of carbon atoms can be outside of these ranges, an aryl group (including substituted and unsubstituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 50 carbon atoms, in another embodiment with no more than about 20 carbon atoms, and in yet another embodiment with no more than about 14 carbon atoms, although the number of carbon atoms can be outside of these ranges, an arylalkyl group (including substituted and unsubstituted arylalkyl groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, an alkylaryl group (including substituted and unsubstituted alkylaryl groups, and wherein hetero atoms, such as oxygen, nitrogen, sulfur, silicon, phosphorus, and the like either may or may not be present in either or both of the aryl portion and the alkyl portion of the alkylaryl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, a silyl group (including unsubstituted and substituted silyl groups, and including polysilylene groups, in one embodiment with from 2 to about 100 repeat silylene units, although the number of repeat units can be outside of this range), or a siloxy group (including unsubstituted and substituted siloxy groups, and including polysiloxane groups, in one embodiment with from 2 to about 200 repeat siloxane units, although the number of repeat units can be outside of this range), or (x) a phosphoryl group of the formula $-PO_3R_{90}$, wherein $R_{90}$ is a hydrogen atom, an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 50 carbon atoms, in another embodiment with no more than about 20 carbon atoms, and in yet another embodiment with no more than about 10 carbon atoms, although the number of carbon atoms can be outside of these ranges, an aryl group (including substituted and unsubstituted aryl groups, and wherein hetero atoms, such as oxygen, nitrogen, sulfur, silicon, phosphorus, and the like either may or may not be present in the aryl group), in one embodiment with at least about 6 carbon atoms, and in one embodiment with no more than about 50 carbon atoms, in another embodiment with no more than about 20 carbon atoms, and in yet another embodiment with no more than about 14 carbon atoms, although the number of carbon atoms can be outside of these ranges, an arylalkyl group (including substituted and unsubstituted arylalkyl groups, and wherein hetero atoms, such as oxygen, nitrogen, sulfur, silicon, phosphorus, and the like either may or may not be present in either or both of the aryl portion and the alkyl portion of the arylalkyl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, an alkylaryl group (including substituted and unsubstituted alkylaryl groups, and wherein hetero atoms, such as oxygen, nitrogen, sulfur, silicon, phosphorus, and the like either may or may not be present in either or both of the aryl portion and the alkyl portion of the alkylaryl group), in one embodiment with at least about 7 carbon atoms, and in one embodiment with no more than about 50 carbon atoms, in another embodiment with no more than about 25 carbon atoms, and in yet another embodiment with no more than about 15 carbon atoms, although the number of carbon atoms can be outside of these ranges, a silyl group (including unsubstituted and substituted silyl groups, and including polysilylene groups, in one embodiment with from 2 to about 100 repeat silylene units, although the number of repeat units can be outside of this range), or a siloxy group (including unsubstituted and substituted siloxy groups, and including polysiloxane groups, in one embodiment with from 2 to about 200 repeat siloxane units, although the number of repeat units can be outside of this range), wherein the substituents on the substituted alkyl, aryl, arylalkyl, alkylaryl, silyl, and siloxy groups are hydroxy groups, halogen atoms, cyano groups, ether groups, aldehyde groups, ketone groups, carboxylic acid groups, ester groups, amide groups, carbonyl groups, thiocarbonyl groups, sulfate groups, sulfonate groups, sulfide groups, sulfoxide groups, phosphate groups, nitrile groups, mercapto groups, nitro groups, nitroso groups, sulfone groups, acyl groups, acid anhydride groups, azide groups, cyanato groups, isocyanato groups, thiocyanato groups, isothiocyanato groups, mixtures thereof, and the like, wherein the substituents on the silyl and siloxy groups can also be alkyl groups, aryl groups, arylalkyl groups, and alkylaryl groups, wherein two or more substituents can be joined together to form a ring. Up to 4 Z groups can be present on each chromophore moiety. Since hetero atoms can be present in the alkyl, aryl, arylalkyl, and alkylaryl groups, these groups also include alkoxy, aryloxy, arylalkyloxy, alkylaryloxy, and the like; in addition, these groups also include polyalkyleneoxy groups, polyaryleneoxy groups, polyarylalkyleneoxy groups, polyalkylaryleneoxy groups, and the like. Further, since hetero atoms can be present in these groups, these groups also include heterocyclic groups.

Two or more of the groups $R_1$, Z, and X can be joined together to form a ring.

Some specific examples of these colorants include

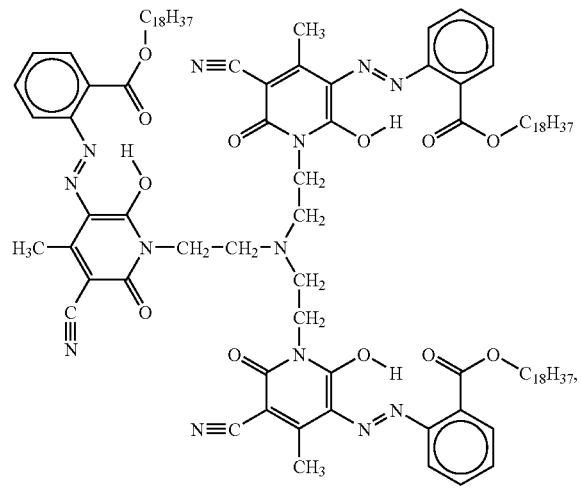

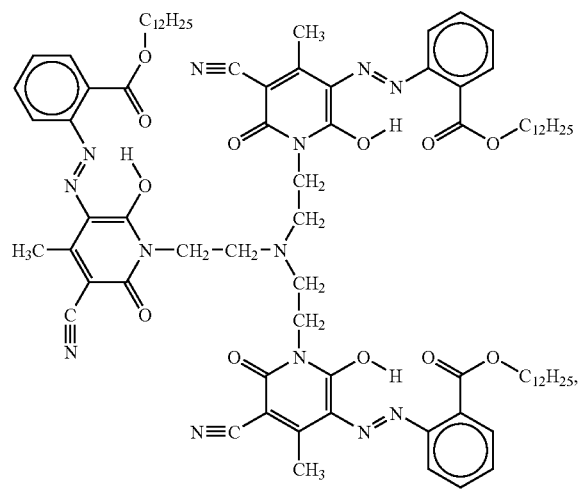

-continued
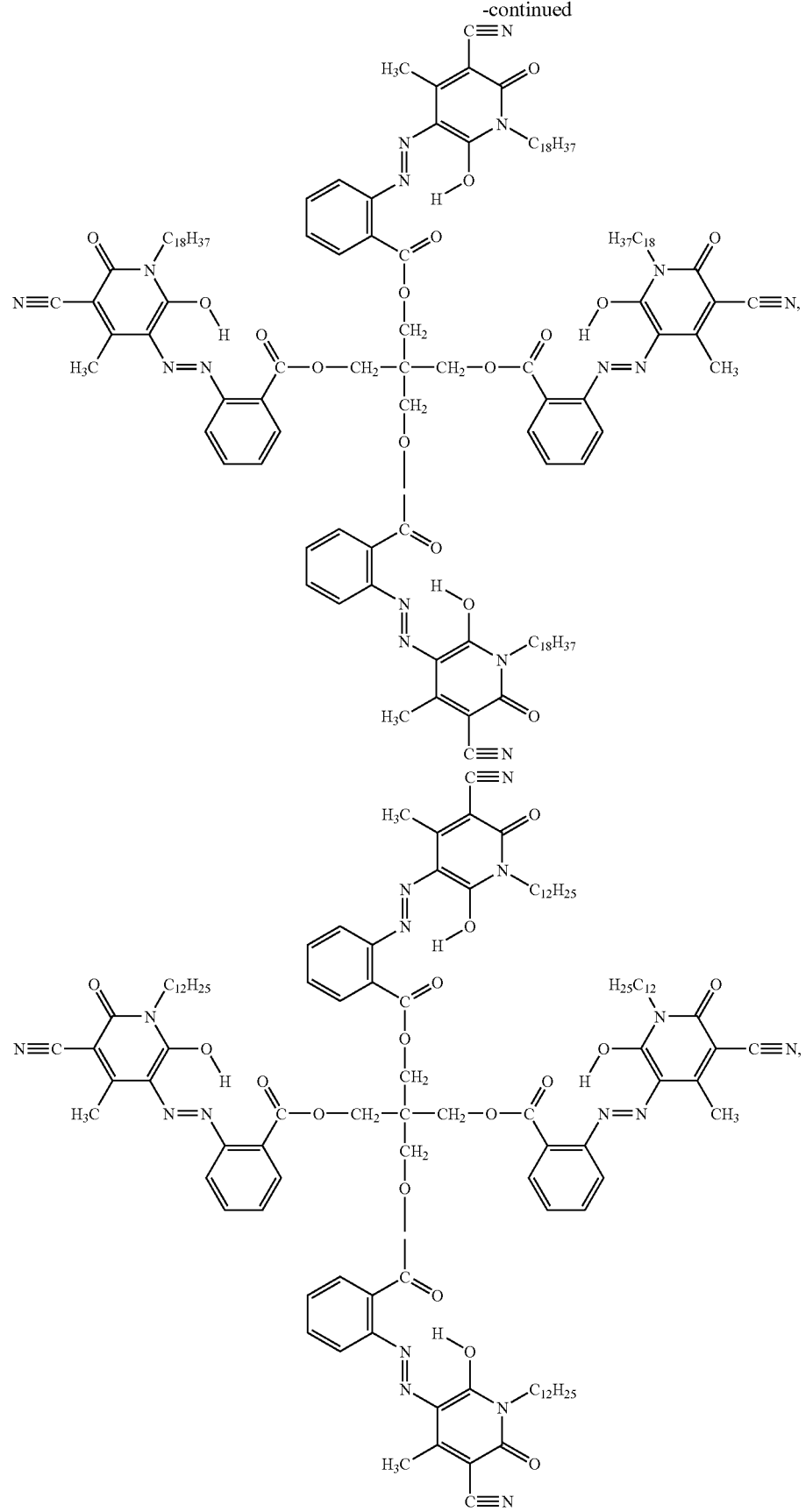

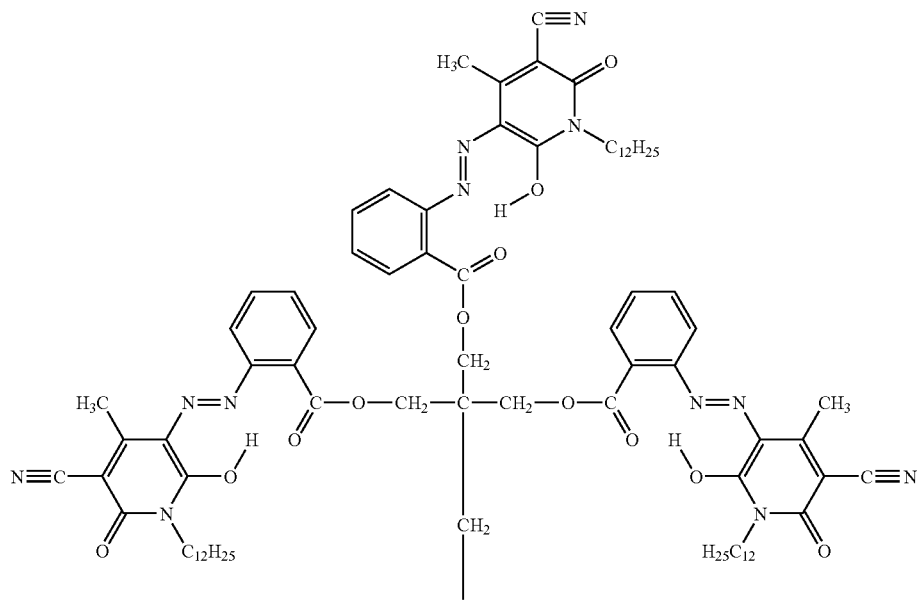
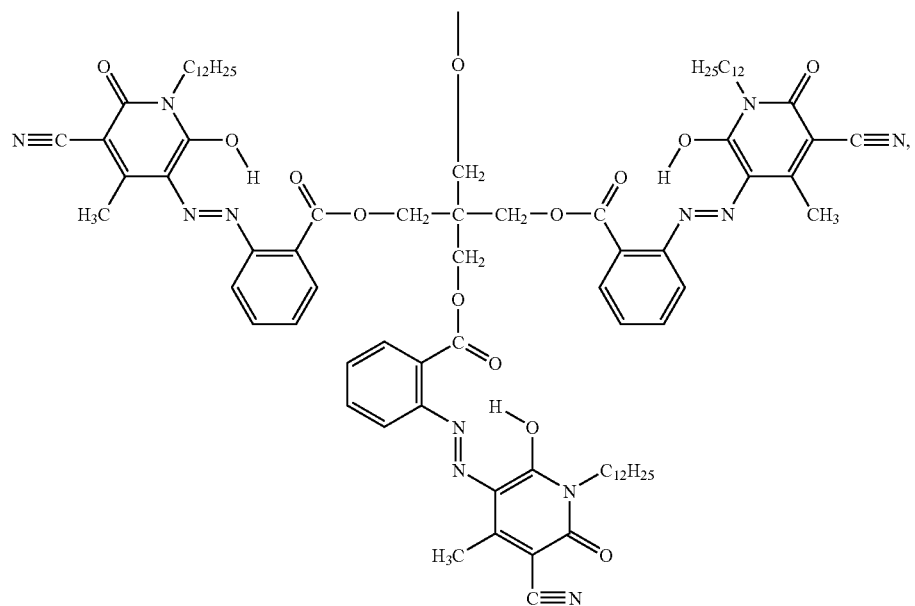

-continued
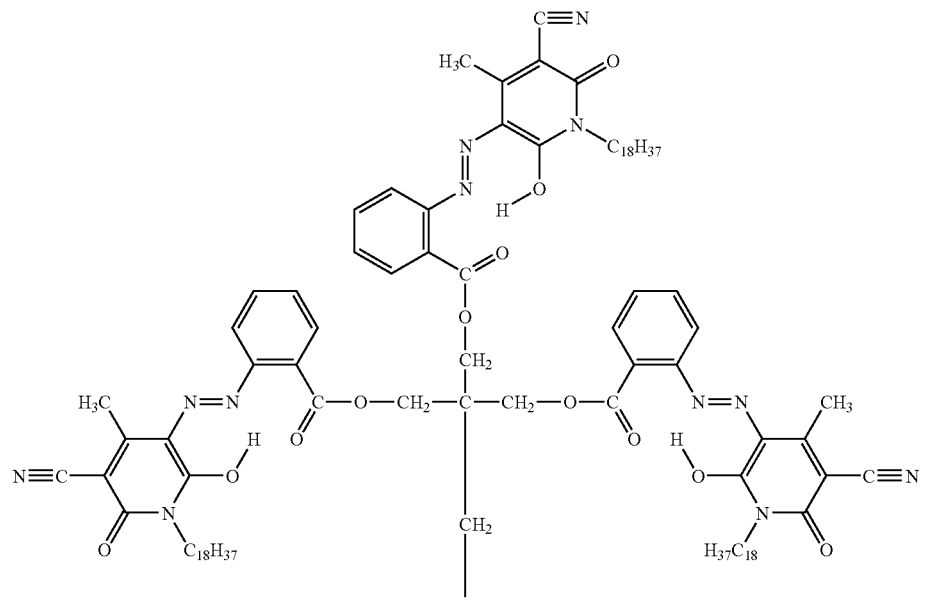
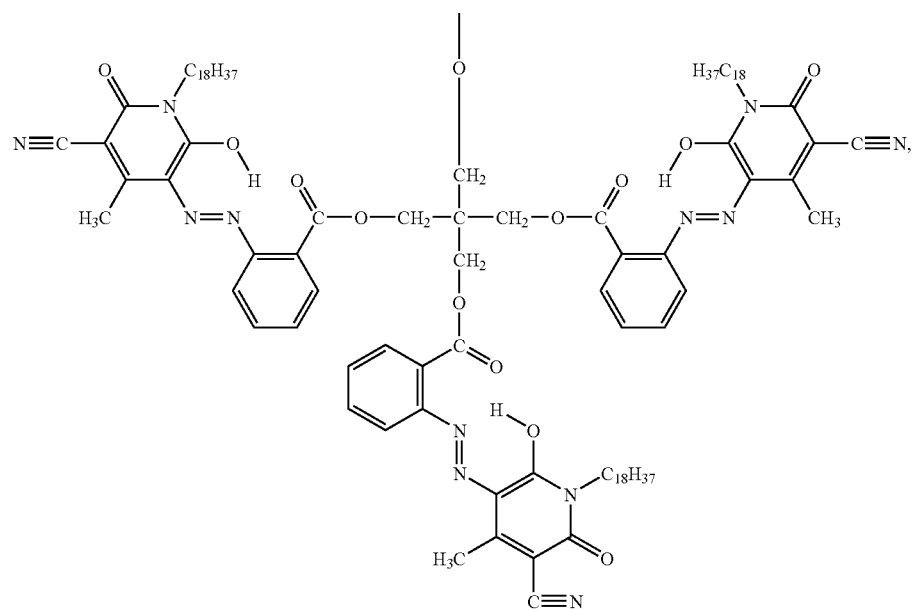

-continued
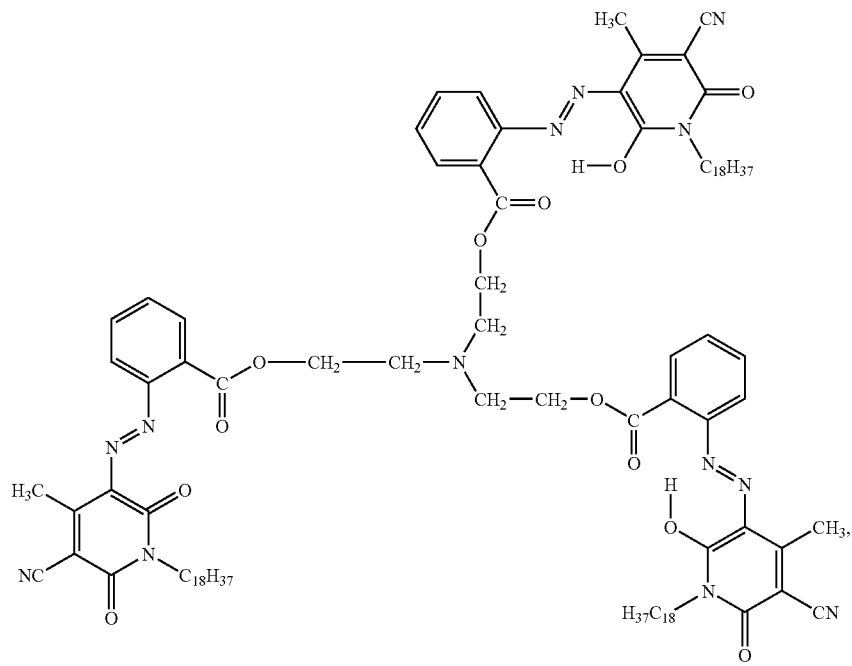
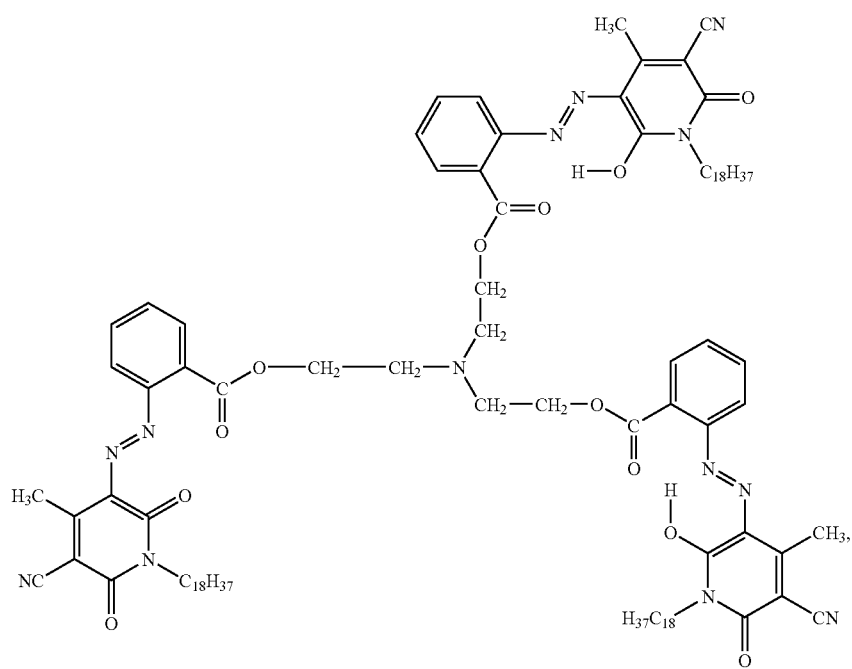

-continued

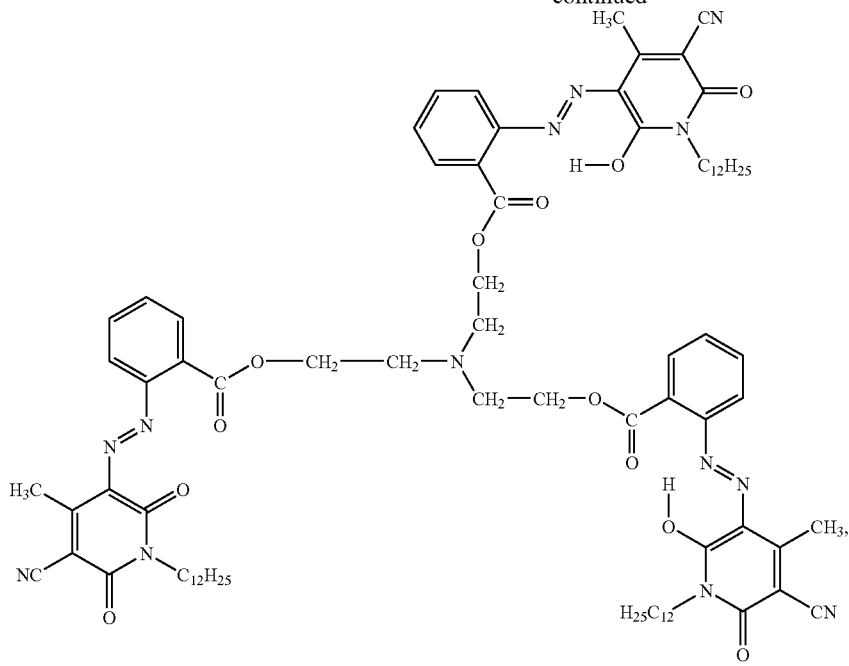

and the like.

The colorant compounds for the inks of the present invention can be prepared by any desired or effective method. For example, colorants wherein the

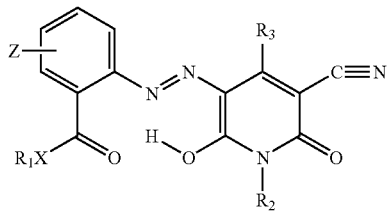

moieties are linked to the central atom or group of atoms or bonded to a polymer through $R_1$ can be prepared by formation of anthranilate moieties on the central atom or group of atoms or oligomer or polymer. Anthranilate moieties can be formed by, for example, converting primary or secondary hydroxyl groups to anthranilate moieties by reaction of the hydroxyl groups with isatoic anhydride in the presence of a catalyst, such as 1,4-diazabicyclo(2.2.2)octane, N,N,N',N'-tetramethylethylene diamine, or the like, and heating. The anthranilate moieties on the central atom or group of atoms or oligomer or polymer can then be diazotized with nitrosylsulfuric acid under cold temperature conditions, followed by coupling with the correspondingly substituted pyridone in a buffered alkaline aqueous solution under cold temperature conditions. More specifically, the correspondingly substituted polyanthranilate is first subjected to a diazotization reaction by dissolving it in acetic acid diluted with a solvent and, optionally, a second acid, such as sulfuric acid, dodecylbenzene sulfonic acid, propionic acid, hydrochloric acid, phosphoric acid, any other acid useful for a diazotization reaction, or the like, as well as mixtures thereof. The solvent can be any solvent useful in a diazotization reaction, such as water, acetone, dimethylformamide, dimethylacetamide, tetrahydrofuran, dimethoxyethane, analogous higher-boiling ether solvents, and the like, as well as mixtures thereof.

The solvent and the polyanthranilate are present in any desired or effective relative amounts; if, for purposes of determining relative amounts, "solvent" is defined to include whatever solvent has been selected plus any amount of acetic acid and second acid present, the reactants are present in this combined solvent in relative amounts of in one embodiment at least about 100 grams of polyanthranilate per liter of solvent, in another embodiment at least about 200 grams of polyanthranilate per liter of solvent, and in yet another embodiment at least about 230 grams of polyanthranilate per liter of solvent, and in one embodiment of no more than about 400 grams of polyanthranilate per liter of solvent, in another embodiment of no more than about 300 grams of polyanthranilate per liter of solvent, and in yet another embodiment of no more than about 270 grams of polyanthranilate per liter of solvent, although the relative amounts can be outside of these ranges.

The acetic acid is present in any desired or effective amount, in one embodiment at least about 1 gram of acetic acid per gram of polyanthranilate, in another embodiment at least about 2 grams of acetic acid per gram of polyanthranilate, and in yet another embodiment at least about 3 grams of acetic acid per gram of polyanthranilate, and in one embodiment no more than about 10 grams of acetic acid per gram of polyanthranilate, in another embodiment no more than about 7 grams of acetic acid per gram of polyanthranilate, and in yet another embodiment no more than about 5 grams of acetic acid per gram of polyanthranilate, although the relative amounts can be outside of these ranges.

When present, the optional second acid is present in any desired or effective amount, in one embodiment at least about 0.05 gram of acid per gram of polyanthranilate, and in another embodiment at least about 0.1 gram of acid per gram of polyanthranilate, and in one embodiment no more than about 0.5 grams of acid per gram of polyanthranilate, in another embodiment no more than about 0.3 grams of acid per gram of polyanthranilate, and in yet another embodiment no more than about 0.2 grams of acid per gram of polyanthranilate, although the relative amounts can be outside of these ranges.

In the mixture comprising the selected solvent, any optional second acid, and acetic acid, the acetic acid is present in any desired or effective amount, in one embodiment at least about 50 percent by volume of the mixture, in another embodiment at least about 70 percent by volume of the mixture, in yet another embodiment at least about 75 percent by volume of the mixture, and in still another embodiment at least about 95 percent by volume of the mixture, although the relative amount can be outside of these ranges.

Upon complete dissolution of the ingredients, the mixture is cooled, in one embodiment to a temperature of no more than about +15° C., in another embodiment to a temperature of no more than about +10° C., in yet another embodiment to a temperature of no more than about +5° C., in still another embodiment to a temperature of no more than about +3° C., and in one embodiment to a temperature of no lower than about −5° C., and in another embodiment to a temperature of no lower than about −10° C., although the temperature can be outside of these ranges.

Thereafter, nitrosylsulfuric acid is added to the mixture in any desired or effective amount, in one embodiment at least 1 mole of nitrosylsulfuric acid per every one mole of aniline moiety in the polyanthranilate, and in another embodiment at least about 1.05 moles of nitrosylsulfuric acid per every one mole of aniline moiety in the polyanthranilate, and in one embodiment no more than about 1.5 moles of nitrosylsulfuric acid per every one mole of aniline moiety in the polyanthranilate, in another embodiment no more than about 1.25 moles of nitrosylsulfuric acid per every one mole of aniline moiety in the polyanthranilate, and in yet another embodiment no more than about 1.15 moles of nitrosylsulfuric acid per every one mole of aniline moiety in the polyanthranilate, although the relative amounts can be outside of these ranges. In a specific embodiment, the nitrosylsulfuric acid is added dropwise at a rate such that the temperature of the reaction mixture does not exceed 15° C.

The reaction to form the diazonium salt is essentially instantaneous, and upon completion of addition of the nitrosylsulfuric acid the reaction is essentially complete, although, if desired, a qualitative test can be performed to confirm reaction completion.

Thereafter, residual excess nitrosylsulfuric acid present in the reaction mixture can be quenched by the addition of a quenching agent, such as sulfamic acid, urea, or the like as well as mixtures thereof, in any desired or effective amount, in one embodiment at least about 0.01 mole of quenching agent per mole of nitrosylsulfuric acid (i.e., per mole of nitrosylsulfuric acid originally added to the reaction mixture), in another embodiment at least about 0.05 mole of quenching agent per mole of nitrosylsulfuric acid, and in yet another embodiment at least about 0.1 mole of quenching agent per mole of nitrosylsulfuric acid, and in one embodiment no more than about 0.5 mole of quenching agent per mole of nitrosylsulfuric acid, in another embodiment no more than about 0.3 mole of quenching agent per mole of nitrosylsulfuric acid, and in yet another embodiment no more than about 0.2 mole of quenching agent per mole of nitrosylsulfuric acid, although the amount can be outside of these ranges. Upon completion of the reaction, the reaction mixture contains the corresponding diazonium salt.

A precursor solution of the pyridone having the desired substituents thereon is prepared in an appropriate solvent, such as a mixture of water, organic solvents, including lower alcohols such as methanol, ethanol, isopropanol, and the like, water-miscible nonbasic organic solvents such as tetrahydrofuran, acetone, dimethoxyethane, N,N-dimethylformamide, N,N-dimethylacetamide, and the like, as well as mixtures thereof. Mixtures of water with an organic solvent can be helpful for ease of solvating inorganic or organic salts that are a reaction by-product. In this instance, water and the organic solvent are present in any desired or effective relative amounts, in one embodiment at least about 0.25 gram of organic solvent per gram of water, in another embodiment at least about 0.3 gram of organic solvent per gram of water, and in yet another embodiment at least about 0.4 gram of organic solvent per gram of water, and in one embodiment no more than about 4 grams of organic solvent per gram of water, in another embodiment no more than about 3 grams of organic solvent per gram of water, and in yet another embodiment no more than about 2 grams of organic solvent per gram of water, although the relative amounts can be outside of these ranges.

The pyridone is present in the precursor solution in any desired or effective amount, in one embodiment at least about 10 grams of pyridone per liter of solvent, in another embodiment at least about 30 grams of pyridone per liter of solvent, and in yet another embodiment at least about 50 grams of pyridone per liter of solvent, and in one embodiment no more than about 200 grams of pyridone per liter of solvent, in another embodiment no more than about 100 grams of pyridone per liter of solvent, and in yet another embodiment no more than about 70 grams of pyridone per liter of solvent, although the relative amounts can be outside of these ranges.

The pyridone precursor solution is maintained at an alkaline pH, typically of at least about 10, and in one embodiment no more than about 14, and in another embodiment no more than about 12, although the pH can be outside of these ranges. The pyridone precursor solution can contain a mixture of a base and an optional buffering salt.

Examples of suitable bases include mineral bases, such as sodium hydroxide, potassium hydroxide, and the like, as well as water-miscible organic tertiary amines, such as triethanolamine, N,N-diethylethanolamine, and the like, as well as mixtures thereof, present in any desired or effective amount, in one embodiment at least about 1 mole of base per mole of pyridone, in another embodiment at least about 2 moles of base per mole of pyridone, in yet another embodiment at least about 3 moles of base per mole of pyridone, and in still another embodiment at least about 5 moles of base per mole of pyridone, and in one embodiment no more than about 10 moles of base per mole of pyridone, in another embodiment no more than about 7 moles of base per mole of pyridone, and in yet another embodiment no more than about 5 moles of base per mole of pyridone, although the relative amounts can be outside of these ranges.

Examples of suitable optional buffer salts include those corresponding to the principal acid solvent; for example, when the principal acid solvent is acetic acid, suitable buffers include sodium acetate, potassium acetate, sodium hydrogen phosphate, citric acid, and the like, as well as mixtures thereof. When present, the optional buffer salt is present in any desired or effective amount, in one embodiment at least about 1 mole of buffer per mole of pyridone, in another embodiment at least about 2 moles of buffer per mole of pyridone, in yet another embodiment at least about 3 moles of buffer per mole of pyridone, and in still another embodiment at least about 5 moles of buffer per mole of pyridone, and in one embodiment no more than about 10 moles of buffer per mole of pyridone, in another embodiment no more than about 7 moles of buffer per mole of pyridone, and in yet another embodiment no more than about 5 moles of buffer per mole of pyridone, although the relative amounts can be outside of these ranges. In a specific embodiment, upon dissolution of the pyridone, the thus-formed precursor pyridone solution can be filtered to remove any undissolved solids.

The solution containing the diazonium salt, maintained at a cold temperature, is then slowly added to the pyridone solution in any desired or effective relative amounts, in one embodiment at least about 1 mole of pyridone per mole of diazonium salt, in another embodiment at least about 1.2 moles of pyridone per mole of diazonium salt, and in yet another embodiment at least about 1.5 moles of pyridone per mole of diazonium salt, and in one embodiment no more than about 3 moles of pyridone per mole of diazonium salt, in another embodiment no more than about 2 moles of pyridone per mole of diazonium salt, and in yet another embodiment no more than about 1.6 moles of pyridone per mole of diazonium salt, although the relative amounts can be outside of these ranges, resulting in the immediate formation of a bright yellow precipitate. Thereafter, the yellow precipitate can be collected by filtration and, if desired, washed.

Precursor polyanilines can be prepared by any desired or effective method, such as that disclosed in, for example, "The Chemistry of Isatoic Anhydride," G. M. Coppola, *Synthesis*, p. 505 (1980); "Isatoic Anhydride. IV. Reactions with Various Nucleophiles," R. P. Staiger et al., *J. Org. Chem.*, Vol. 24, p. 1214 (1959); R. P. Staiger et al., *J. Chem. Eng.* Data B, p. 454 (1963); and U.S. Pat. No. 4,016,143; the disclosures of each of which are totally incorporated herein by reference.

In addition, precursor polyanthranilates can be prepared by admixing (1) the correspondingly substituted triol or higher alcohol having the desired structure wherein the hydroxy groups are primary or secondary, with (2) isatoic anhydride, (3) a base catalyst, and (4) a solvent; and (b) heating the mixture thus formed to form the desired polyanthranilate precursor compound.

Isatoic anhydride and the selected polyol are present in any desired or effective relative amounts, in one embodiment at least about 1 mole of isatoic anhydride per every one mole of hydroxy groups present in the polyol, in another embodiment at least about 1.02 moles of isatoic anhydride per every one mole of hydroxy groups present in the polyol, in yet another embodiment at least about 1.05 moles of isatoic anhydride per every one mole of hydroxy groups present in the polyol, and in still another embodiment at least about 1.1 moles of isatoic anhydride per every one mole of hydroxy groups present in the polyol, and in one embodiment no more than about 2.5 moles of isatoic anhydride per every one mole of hydroxy groups present in the polyol, in another embodiment no more than about 1.5 moles of isatoic anhydride per every one mole of hydroxy groups present in the polyol, and in yet another embodiment no more than about 1.2 moles of isatoic anhydride per every one mole of hydroxy groups present in the polyol, although the relative amounts of reactants can be outside of these ranges.

Examples of suitable catalysts include 1,4-diazabicyclo (2.2.2) octane, N,N,N',N'-tetramethylethylene diamine, mixtures thereof, and the like. The catalyst is present in the reaction mixture in any desired or effective amount, in one embodiment at least about 0.1 mole of catalyst per every one mole of hydroxy groups present in the polyol, in another embodiment at least about 0.11 mole of catalyst per every one mole of hydroxy groups present in the polyol, in yet another embodiment at least about 0.12 mmole of catalyst per every one mole of hydroxy groups present in the polyol, and in still another embodiment at least about 0.25 mole of catalyst per every one mole of hydroxy groups present in the polyol, and in one embodiment no more than about 1 mole of catalyst per every one mole of hydroxy groups present in the polyol, in another embodiment no more than about 0.5 mole of catalyst per every one mole of hydroxy groups present in the polyol, and in yet another embodiment no more than about 0.26 mole of catalyst per every one mole of hydroxy groups present in the polyol, although the relative amount of catalyst can be outside of these ranges.

The reactants typically are present in a suitable solvent. The reactants can be either soluble or insoluble in the solvent, resulting in a homogeneous or a heterogeneous reaction mixture. Examples of suitable solvents include toluene, xylene, methyl ethyl ketone, ethyl acetate, butyl acetate, chlorobenzene, dioxane, dimethylformamide, N-methyl-2-pyrrolidinone, dimethylsulfoxide, sulfolane, pyridone, and the like, as well as mixtures thereof, with toluene and butyl acetate being preferred.

The reactants can be present in the solvent in any desired or effective relative amounts. The solvent is present in an amount of in one embodiment at least about 0.1 mole of polyol per liter of solvent, in another embodiment at least about 0.25 mole of polyol per liter of solvent, in yet another embodiment at least about 0.5 mole of polyol per liter of solvent, and in still another embodiment at least about 0.75 mole of polyol per liter of solvent, and is present in an amount of in one embodiment no more than about 3 moles of polyol per liter of solvent, in another embodiment no more than about 2 moles of polyol per liter of solvent, in yet another embodiment no more than about 1.5 moles of polyol per liter of solvent, and in still another embodiment no more than about 0.75 mole of polyol per liter of solvent, although the relative amount of solvent can be outside of these ranges.

The reaction mixture is heated to any desired or effective temperature, in one embodiment to a temperature of at least about 40° C., in another embodiment to a temperature of at least about 75° C., and in yet another embodiment to a temperature of at least about 100° C., and is heated in one embodiment to a temperature of no more than about 200° C., in another embodiment to a temperature of no more than about 170° C., and in yet another embodiment of no more than about 150° C., although the temperature can be outside of these ranges.

The reaction is carried out by heating for any desired or effective amount of time, in one embodiment for a period of at least about 1 hour, in another embodiment for a period of at least about 2.5 hours, and in yet another embodiment for a period of at least about 3 hours, and in one embodiment for a period of no more than about 10 hours, in another embodiment for a period of no more than about 6 hours, and in yet another embodiment for a period of no more than about 3.5 hours, although the reaction time can be outside of these ranges.

Subsequent to completion of the reaction, excess isatoic anhydride can be quenched, by, for example, the dropwise addition of a dilute solution (about 5 percent, for example) of aqueous sodium or potassium hydroxide to convert isatoic anhydride to the water-soluble sodium or potassium salt of anthranilic acid. Alternately, excess isatoic anhydride can be reacted with methanol or ethanol, which converts it to methyl or ethyl anthranilate, both of which are liquids soluble in common organic solvents, such as alcohols, ethers, ketones, esters, and the like.

The polyanthranilate product can be separated from the reaction mixture by any desired or effective method. For example, liquid-liquid extraction, which may be desirable when the polyanthranilate is not crystalline at ambient temperature, can be carried out between the organic phase and the aqueous phase of the mixture. (Said aqueous phase can be added when the reaction mixture is subjected to quenching with an aqueous solution; when such quenching is not carried out, water can be added to create the aqueous phase.) In the event of formation of an emulsion between these phases, which could make separation of the layers difficult or very slow, techniques known to those skilled in the art of extractive separation, such as, for example, adding more of the same or a different organic solvent to the organic layer, such as ethyl acetate or the like, and/or adding a salt, such as, for example, sodium chloride, potassium chloride, ammonium sulfate, or the like (typically in amounts from about 5 to about 30 percent by weight in water) can be performed. The organic phase can then, if desired, be dried by any desired or effective method, such as by drying over magnesium sulfate, or the like. The product can then be isolated by removal of the solvent by any desired or effective method, such as vacuum distillation or the like. If desired, the resulting product, while it is still dissolved in the organic phase, can be treated with acidic media, such as an acid-leached bentonite clay (available from Englehart Industries under the Trade name FILTROL® 24), which treatment can serve to remove any undesirable colored basic impurities.

The polyanthranilate product can also be separated from the reaction mixture by precipitation using a non-solvent, which may be desirable when the polyanthranilate product is crystalline. In this situation, a low alcohol, such as methanol or ethanol, is added to the reaction mixture in a molar amount greater than or equal to the amount of unreacted isatoic anhydride, either after cooling to room temperature or at a temperature of up to about 80° C., which serves to convert excess isatoic anhydride to the liquid methyl or ethyl anthranilate. Addition of a non-solvent for the polyanthranilate, such as water, methanol, isopropanol, or the like is then used to precipitate the product, which can then be separated by filtration, washing with a suitable solvent, and drying.

Precursor pyridones can be prepared by any desired or effective method, such as that disclosed in, for example, "Investigation of the Reaction Conditions for the Synthesis of 4,6-Disubstituted-3-cyano-2-pyridones and 4-Methyl-3-cyano-6-hydroxy-2-pyridone," D. Z. Mijin et al., *J. Serb. Chem. Soc.*, Vol. 59, No. 12, p. 959 (1994); "Synthesis of Isoquinoline Alkaloids. II. The Synthesis and Reactions of 4-Methyl-3-pyridinecarboxaldehyde and Other 4-Methyl-3-substituted Pyridines," J. M. Bobbitt et al., *J. Org. Chem.*, Vol. 25, p. 560 (1960); "Synthesis and Dyeing Characteristics of 5-(4-Arylazophenyl)azo-3-cyano-4-methyl-6-hydroxy-2-pyridones," J. M. Kanhere et al., *Indian Journal of Textile Research*, Vol. 13, p. 213 (1988); "Synthesis of Some Pyridone Azo Dyes from 1-Substituted 2-Hydroxy-6-pyridone Derivatives and their Colour Assessment," C. Chen et al., *Dyes and Pigments*, Vol. 15, p. 69 (1991); "Synthesis of 3-Cyano-6-hydroxy-5-(2-(perfluoroalkyl)phenylazo)-2-pyridones and their Application for Dye Diffusion Thermal Transfer Printing," M. Matsui et al., *Bull. Chem. Soc. Jpn.*, 1993, Vol. 66, Iss. 6, Pp. 1790-4; "Synthesis of N-alkylcyanopyridones," B. Peng et al., *Faming Zhuanli Shenqing Gongkai Shuomingshu* (1997), CN 1158845; "Synthesis of 1-Butyl-3-cyano-4-methyl-6-hydroxypyrid-2-one," X. Kong et al., *Huaxue Shiji* (1998), 20(1), 58-59; "Regioselective Conversion of 3-Cyano-6-hydroxy-2-pyridones into 3-Cyano-6-amino-2-pyridones," A. R. Katritzky et al., *J. Heterocycl. Chem.* (1995), 32(3), 1007-10; "The Synthesis of Some Hetarylazopyridone Dyes and Solvent Effects on their Absorption Spectra," N. Ertan et al., *Dyes Pigm.* (1995), 27(4), 313-20; "Process for the Preparation of Pyridone Compounds," H. Schmid, Ger. Offen. DE 4314430 (1994); "Tautomerism of 4-Methyl-6-hydroxy-2-pyridone derivatives," H. Liu et al., *Dalian Ligong Daxue Xueboo* (1992), 32(4), 405-11; "Preparation of 1-Alkyl-3-cyano-4-methyl-6-hydroxy-2-pyridone-type Mixed Azo Coupling Components," J. Prikryl et al., Czech. (1991) 8 pp. CODEN: CZXXA9 CS 273045 B1 19911220 CAN 118:256604 AN 1993:256604 CAPLUS; "Structural Characteristics of Hydroxypyridone Derivatives," Q. Peng et al., *Dalian Ligong Daxue Xueboo* (1991), 31(3), 279-86; and "6-Hydroxypyridin-2-ones," F. Schmidt, Ger. Offen. DE 2845863 (1980); the disclosures of each of which are totally incorporated herein by reference.

When polymeric products are desired, polymers having three or more pendant primary or secondary alcohol or hydroxy groups, in one embodiment at least about 6 alcohol or hydroxy groups, and in another embodiment at least about 10 alcohol or hydroxy groups, and in one embodiment no more than about 30 alcohol or hydroxy groups, and in another embodiment no more than about 20 alcohol or hydroxy groups, although the number of alcohol or hydroxy groups can be outside of these ranges, can be converted to polyanthranilates by the method described hereinabove. Any desired or effective polymer can be employed, such as polyvinyl alcohol, commercially available, polyvinyl acetate which has been reduced, or the like.

Colorants wherein the

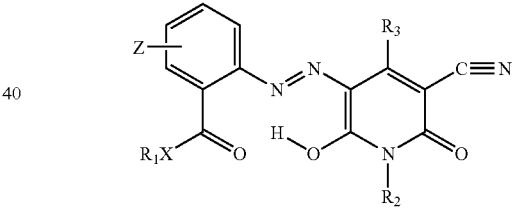

moieties are linked to the central atom or group of atoms or bonded to a polymer through $R_2$ can be prepared by any desired or effective method. For example, they can be prepared by formation of pyridone moieties on the central atom or group of atoms or oligomer or polymer. Pyridone moieties can be formed by, for example, converting primary amino groups to pyridone moieties by reactions with esters as described in further detail hereinbelow. The pyridone moieties can in turn be coupled in a buffered alkaline aqueous solution under cold temperature conditions with a stoichiometric number of anthranilate moieties which have been previously diazotized with nitrosylsulfuric acid under cold temperature conditions. More specifically, the anthranilate is first subjected to a diazotization reaction by dissolving it in acetic acid diluted with a solvent and, optionally, a second acid, such as sulfuric acid, dodecylbenzene sulfonic acid, propionic acid, hydrochloric acid, phosphoric acid, any other acid useful for a diazotization reaction, or the like, as well as mixtures thereof. The solvent can be any solvent useful in a diazotization reaction, such as water, acetone, dimethylformamide, dimethyacetamide, tetrahydrofuran, dimethoxyethane, analogous higher-boiling ether solvents, and the like, as well as mixtures thereof.

The solvent and the anthranilate are present in any desired or effective relative amounts; if, for purposes of determining relative amounts, "solvent" is defined to include whatever solvent has been selected plus any amount of acetic acid and second acid present, the reactants are present in this combined solvent in relative amounts of in one embodiment at least about 100 grams of anthranilate per liter of solvent, in another embodiment at least about 200 grams of anthranilate per liter of solvent, and in yet another embodiment at least about 230 grams of anthranilate per liter of solvent, and in one embodiment of no more than about 400 grams of anthranilate per liter of solvent, in another embodiment of no more than about 300 grams of anthranilate per liter of solvent, and in yet another embodiment of no more than about 270 grams of anthranilate per liter of solvent, although the relative amounts can be outside of these ranges.

The acetic acid is present in any desired or effective amount, in one embodiment at least about 1 gram of acetic acid per gram of anthranilate, in another embodiment at least about 2 grams of acetic acid per gram of anthranilate, and in yet another embodiment at least about 3 grams of acetic acid per gram of anthranilate, and in one embodiment no more than about 10 grams of acetic acid per gram of anthranilate, in another embodiment no more than about 7 grams of acetic acid per gram of anthranilate, and in yet another embodiment no more than about 5 grams of acetic acid per gram of anthranilate, although the relative amounts can be outside of these ranges.

When present, the optional second acid is present in any desired or effective amount, in one embodiment at least about 0.05 gram of acid per gram of anthranilate, and in another embodiment at least about 0.1 gram of acid per gram of anthranilate, and in one embodiment no more than about 0.5 grams of acid per gram of anthranilate, in another embodiment no more than about 0.3 grams of acid per gram of anthranilate, and in yet another embodiment no more than about 0.2 grams of acid per gram of anthranilate, although the relative amounts can be outside of these ranges.

In the mixture comprising the selected solvent, any optional second acid, and acetic acid, the acetic acid is present in any desired or effective amount, in one embodiment at least about 50 percent by volume of the mixture, in another embodiment at least about 70 percent by volume of the mixture, in yet another embodiment at least about 75 percent by volume of the mixture, and in still another embodiment at least about 95 percent by volume of the mixture, although the relative amount can be outside of these ranges.

Upon complete dissolution of the ingredients, the mixture is cooled, in one embodiment to a temperature of no more than about +15° C., in another embodiment to a temperature of no more than about +10° C., in yet another embodiment to a temperature of no more than about +5° C., in still another embodiment to a temperature of no more than about +3° C., and in one embodiment to a temperature of no lower than about −5° C., and in another embodiment to a temperature of no lower than about −10° C., although the temperature can be outside of these ranges.

Thereafter, nitrosylsulfuric acid is added to the mixture in any desired or effective amount, in one embodiment at least about 1 mole of nitrosylsulfuric acid per mole of anthranilate, and in another embodiment at least about 1.05 moles of nitrosylsulfuric acid per mole of anthranilate, and in one embodiment no more than about 1.5 moles of nitrosylsulfuric acid per mole of anthranilate, in another embodiment no more than about 1.25 moles of nitrosylsulfuric acid per mole of anthranilate, and in yet another embodiment no more than about 1.15 moles of nitrosylsulfuric acid per mole of anthranilate, although the relative amounts can be outside of these ranges. In a specific embodiment, the nitrosylsulfuric acid is added dropwise at a rate such that the temperature of the reaction mixture does not exceed 15° C.

The reaction is essentially instantaneous, and upon completion of addition of the nitrosylsulfuric acid the reaction is essentially complete, although, if desired, a qualitative test can be performed to confirm reaction completion.

Thereafter, residual excess nitrosylsulfuric acid present in the reaction mixture can be quenched by the addition of a quenching agent, such as sulfamic acid, urea, or the like as well as mixtures thereof, in any desired or effective amount, in one embodiment at least about 0.01 mole of quenching agent per mole of nitrosylsulfuric acid (i.e., per mole of nitrosylsulfuric acid originally added to the reaction mixture), in another embodiment at least about 0.05 mole of quenching agent per mole of nitrosylsulfuric acid, and in yet another embodiment at least about 0.1 mole of quenching agent per mole of nitrosylsulfuric acid, and in one embodiment no more than about 0.5 mole of quenching agent per mole of nitrosylsulfuric acid, in another embodiment no more than about 0.3 mole of quenching agent per mole of nitrosylsulfuric acid, and in yet another embodiment no more than about 0.2 mole of quenching agent per mole of nitrosylsulfuric acid, although the amount can be outside of these ranges. Upon completion of the reaction, the reaction mixture contains the corresponding diazonium salt.

A precursor solution of the tripyridone, tetrapyridone, pentapyridone, hexapyridone, or otherwise desirably substituted pyridone having the desired structure (hereinafter referred to as the "polypyridone"; this term includes monomeric tripyridones, tetrapyridones, pentapyridones, hexapyridones, and the like, oligomeric pyridones, and polymeric pyridones) is prepared in an appropriate solvent, such as a mixture of water, organic solvents, including lower alcohols such as methanol, ethanol, isopropanol, and the like, water-miscible nonbasic organic solvents such as tetrahydrofuran, acetone, dimethoxyethane, N,N-dimethylformamide, N,N-dimethylacetamide, and the like, as well as mixtures thereof. Mixtures of water with an organic solvent can be helpful for ease of solvating inorganic and organic salts that are a reaction by-product. In this instance, water and the organic solvent are present in any desired or effective relative amounts, in one embodiment at least about 0.25 gram of organic solvent per gram of water, in another embodiment at least about 0.3 gram of organic solvent per gram of water, and in yet another embodiment at least about 0.4 gram of organic solvent per gram of water, and in one embodiment no more than about 4 grams of organic solvent per gram of water, in another embodiment no more than about 3 grams of organic solvent per gram of water, and in yet another embodiment no more than about 2 grams of organic solvent per gram of water, although the relative amounts can be outside of these ranges.

The polypyridone is present in the precursor solution in any desired or effective amount, in one embodiment at least about 10 grams of polypyridone per liter of solvent, in another embodiment at least about 30 grams of polypyridone per liter of solvent, and in yet another embodiment at least about 50 grams of polypyridone per liter of solvent, and in one embodiment no more than about 200 grams of polypyridone per liter of solvent, in another embodiment no more than about 100 grams of polypyridone per liter of solvent, and in yet another embodiment no more than about 70 grams of polypyridone-per liter of solvent, although the relative amounts can be outside of these ranges.

The polypyridone precursor solution is maintained at an alkaline pH, typically of at least about 10, and in one embodiment no more than about 14, and in another embodiment no more than about 12, although the pH can be outside of these ranges. The polypyridone precursor solution can contain a mixture of a base and an optional buffering salt.

Examples of suitable bases include mineral bases, such as sodium hydroxide, potassium hydroxide, and the like, as well as water-miscible organic tertiary amines, such as triethanolamine, N,N-diethylethanolamine, and the like, as well as mixtures thereof, present in any desired or effective amount, in one embodiment at least about 1 mole of base per every one mole of pyridone moiety in the polypyridone, in another embodiment at least about 2 moles of base per every one mole of pyridone moiety in the polypyridone, in yet another embodiment at least about 3 moles of base per mole of dipyridone, and in still another embodiment at least about 5 moles of base per every one mole of pyridone moiety in the polypyridone, and in one embodiment no more than about 10 moles of base per every one mole of pyridone moiety in the polypyridone, in another embodiment no more than about 7 moles of base per every one mole of pyridone moiety in the polypyridone, and in yet another embodiment no more than about 5 moles of base per every one mole of pyridone moiety in the polypyridone, although the relative amounts can be outside of these ranges.

Examples of suitable buffer salts include those corresponding to the principal acid solvent; for example, when the principal acid solvent is acetic acid, suitable buffers include sodium acetate, potassium acetate, sodium hydrogenphosphate, citric acid, and the like, as well as mixtures thereof, present in any desired or effective amount, in one embodiment at least about 1 mole of buffer per every one mole of pyridone moieties in the polypyridone, in another embodiment at least about 2 moles of buffer per every one mole of pyridone moieties in the polypyridone, in yet another embodiment at least about 3 moles of buffer per every one mole of pyridone moieties in the polypyridone, and in still another embodiment at least about 5 moles of buffer per every one mole of pyridone moieties in the polypyridone, and in one embodiment no more than about 10 moles of buffer per every one mole of pyridone moieties in the polypyridone, in another embodiment no more than about 7 moles of buffer per every one mole of pyridone moieties in the polypyridone, and in yet another embodiment no more than about 5 moles of buffer per every one mole of pyridone moieties in the polypyridone, although the relative amounts can be outside of these ranges. In a specific embodiment, upon dissolution of the dipyridone, the thus-formed precursor polypyridone solution can be filtered to remove any undissolved solids.

The solution containing the diazonium salt, maintained at a cold temperature, is then slowly added to the polypyridone solution in any desired or effective relative amounts, in one embodiment at least about 1 mole of pyridone moiety per mole of diazonium salt, in another embodiment at least about 1.2 moles of pyridone moieties per mole of diazonium salt, and in yet another embodiment at least about 1.5 moles of pyridone moieties per mole of diazonium salt, and in one embodiment no more than about 3 moles of pyridone moieties per mole of diazonium salt, in another embodiment no more than about 2 moles of pyridone moieties per mole of diazonium salt, and in yet another embodiment no more than about 1.6 moles of pyridone moieties per mole of diazonium salt, although the relative amounts can be outside of these ranges, resulting in the immediate formation of a bright yellow precipitate. Thereafter, the yellow precipitate can be collected by filtration and, if desired, washed.

Precursor anthranilates can be prepared by any desired or effective method, such as that disclosed in, for example, "The Chemistry of Isatoic Anhydride," G. M. Coppola, *Synthesis*, p. 505 (1980); "Isatoic Anhydride. IV. Reactions with Various Nucleophiles," R. P. Staiger et al., *J. Org. Chem.*, Vol. 24, p. 1214 (1959); R. P. Staiger et al., *J. Chem. Eng. Data B*, p. 454 (1963); and U.S. Pat. No. 4,016,143; the disclosures of each of which are totally incorporated herein by reference.

Precursor polypyridones can be prepared by any desired or effective method, such as that disclosed in, for example, "Investigation of the Reaction Conditions for the Synthesis of 4,6-Disubstituted-3-cyano-2-pyridones and 4-Methyl-3-cyano-6-hydroxy-2-pyridone," D. Z. Mijin et al., *J. Serb. Chem. Soc.*, Vol. 59, No. 12, p. 959 (1994); "Synthesis of Isoquinoline Alkaloids. II. The Synthesis and Reactions of 4-Methyl-3-pyridinecarboxaldehyde and Other 4-Methyl-3-substituted Pyridines," J. M. Bobbitt et al., *J. Org. Chem.*, Vol. 25, p. 560 (1960); "Synthesis and Dyeing Characteristics of 5-(4-Arylazophenyl)azo-3-cyano-4-methyl-6-hydroxy-2-pyridones," J. M. Kanhere et al., *Indian Journal of Textile Research*, Vol. 13, p. 213 (1988); "Synthesis of Some Pyridone Azo Dyes from 1-Substituted 2-Hydroxy-6-pyridone Derivatives and their Colour Assessment," C. Chen et al., *Dyes and Pigments*, Vol. 15, p. 69 (1991); "Synthesis of 3-Cyano-6-hydroxy-5-(2-(perfluoroalkyl)phenylazo)-2-pyridones and their Application for Dye Diffusion Thermal Transfer Printing," M. Matsui et al., *Bull. Chem. Soc. Jpn.*, 1993, Vol. 66, Iss. 6, Pp. 1790-4; "Synthesis of N-alkylcyanopyridones," B. Peng et al., *Faming Zhuanli Shenqing Gongkai Shuomingshu* (1997), CN 1158845; "Synthesis of 1-Butyl-3-cyano-4-methyl-6-hydroxypyrid-2-one," X. Kong et al., *Huaxue Shiji* (1998), 20(1), 58-59; "Regioselective Conversion of 3-Cyano-6-hydroxy-2-pyridones into 3-Cyano-6-amino-2-pyridones," A. R. Katritzky et al., *J. Heterocycl. Chem.* (1995), 32(3), 1007-10; "The Synthesis of Some Hetarylazopyridone Dyes and Solvent Effects on their Absorption Spectra," N. Ertan et al., *Dyes Pigm.* (1995), 27(4), 313-20; "Process for the Preparation of Pyridone Compounds," H. Schmid, Ger. Offen. DE 4314430 (1994); "Tautomerism of 4-Methyl-6-hydroxy-2-pyridone derivatives," H. Liu et al., *Dalian Ligong Daxue Xuebao* (1992), 32(4), 405-11; "Preparation of 1-Alkyl-3-cyano-4-methyl-6-hydroxy-2-pyridone-type Mixed Azo Coupling Components," J. Prikryl et al., Czech. (1991) 8 pp. CODEN: CZXXA9 CS 273045 B1 19911220 CAN 118:256604 AN 1993:256604 CAPLUS; "Structural Characteristics of Hydroxypyridone Derivatives," Q. Peng et al., *Dalian Ligong Daxue Xuebao* (1991), 31(3), 279-86; and "6-Hydroxypyridin-2-ones, " F. Schmidt, Ger. Offen. DE 2845863 (1980); the disclosures of each of which are totally incorporated herein by reference.

In addition, precursor polypyridones can be prepared by first preparing a corresponding intermediate compound by reacting a polyamine with a first ester compound, as follows:

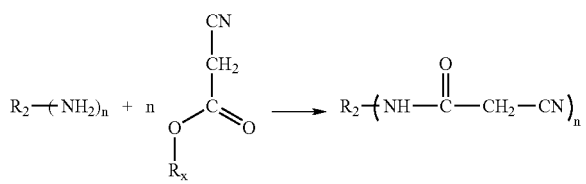

wherein $R_2$ is as defined hereinabove, n is an integer of three or greater, and $R_x$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 5 carbon atoms, although the number of carbon atoms can be outside of these ranges, such as methyl, ethyl, n-propyl, isopropyl, n-butyl, sec-butyl, t-butyl, pentyl, 1-methyl butyl, 2-methyl butyl, 3-methyl butyl, 2,2-dimethyl propyl, 1,3-dimethyl propyl, and the like. For example, some examples of triamines that can be used in this reaction include (but are not limited to) tris(2-aminoethyl)amine, of the formula

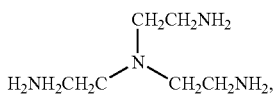

3-methyleneoctane-1,8-diyl triamine, of the formula

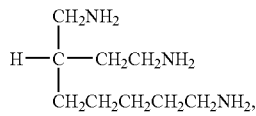

and the like, as well as mixtures thereof. Examples of suitable first ester compounds include methyl cyanoacetate, ethyl cyanoacetate, n-propyl cyanoacetate, isopropyl cyanoacetate, n-butyl cyanoacetate, tert-butyl cyanoacetate, and the like, as well as mixtures thereof. This reaction can, if desired, take place in the absence of any solvent.

The polyamine and the first ester are present in any desired or effective relative amounts, in one embodiment at least about 0.75 mole of amine moiety per every one mole of ester moiety (i.e., in the instance of a triamine, 0.25 mole of triamine molecule per every mole of ester molecule), in another embodiment at least about 0.9 mole of amine moiety per every one mole of ester moiety, and in yet another embodiment at least about 0.95 mole of amine moiety per every one mole of ester moiety, and in one embodiment no more than about 1.25 moles of amine moiety per every one mole of ester moiety, in another embodiment no more than about 1.1 moles of amine moiety per every one mole of ester moiety, and in yet another embodiment no more than about 1.0 mole of amine moiety per every one mole of ester moiety, although the relative amounts of reactants can be outside of these ranges.

The mixture of the polyamine and the first ester is heated to any desired or effective temperature to effect the conversion to the intermediate compound, in one embodiment to a temperature of at least about 80° C., in another embodiment to a temperature of at least about 100° C., and in yet another embodiment to a temperature of at least about 110° C., and is heated in one embodiment to a temperature of no more than about 160° C., in another embodiment to a temperature of no more than about 140° C., and in yet another embodiment of no more than about 120° C., although the temperature can be outside of these ranges.

The reaction between the polyamine and the first ester is carried out by heating for any desired or effective amount of time, in one embodiment for a period of at least about 10 minutes, in another embodiment for a period of at least about 30 minutes, and in yet another embodiment for a period of at least about 45 minutes, and in one embodiment for a period of no more than about 480 minutes, in another embodiment for a period of no more than about 240 minutes, and in yet another embodiment for a period of no more than about 120 minutes, although the reaction time can be outside of these ranges.

The intermediate compound thus formed is then reacted with a second ester and a base ("B") to form the desired pyridone or a salt thereof, as follows:

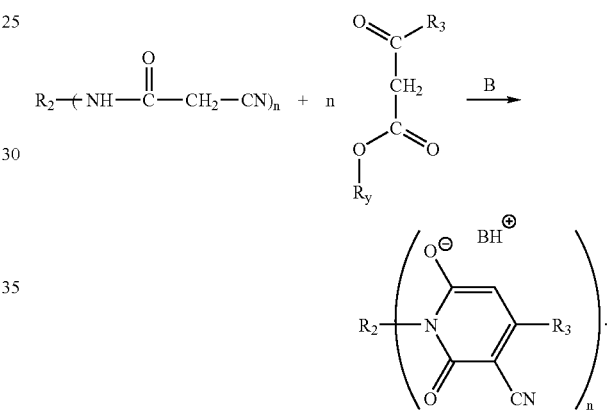

If a salt is formed, it can later be converted to the hydroxy compound by acidification, as follows:

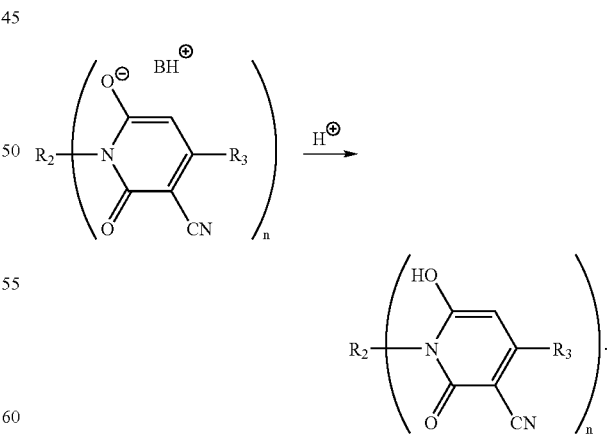

In the second ester, $R_3$ is as defined hereinabove and $R_y$ is an alkyl group (including linear, branched, saturated, unsaturated, cyclic, unsubstituted, and substituted alkyl groups, and wherein hetero atoms, such as oxygen, nitrogen, sulfur, silicon, phosphorus, and the like either may or may not be present in the alkyl group), in one embodiment with at least 1 carbon atom, and in one embodiment with no more than about 5 carbon atoms, although the number of carbon atoms can be outside of this range, such as methyl, ethyl, n-propyl, isopropyl, n-butyl, sec-butyl, t-butyl, pentyl, 1-methyl butyl, 2-methyl butyl, 3-methyl butyl, 2,2-dimethyl propyl, 1,3-dimethyl propyl, and the like. Specific examples of second esters include methyl acetoacetate, ethyl acetoacetate, t-butyl acetoacetate, ethyl butyrylacetate, and the like, as well as mixtures thereof.

Examples of suitable bases include piperidine, 1-methyl piperidine, 1-ethylpiperidine, piperazine, 1-ethylpiperazine, 2-ethylpiperazine, 1-methylpiperazine, 2-methylpiperazine, sodium hydroxide, triethylamine, tributylamine, dimethylethanolamine, diethylethanolamine, 1,4-diazabicyclo(2.2.2) octane, morpholine, 4-ethylmorpholine, t-octylamine, hexamethyl disilazane, tetramethyl ethylenediamine, diethylcyclohexylamine, di-isopropylethylamine, 4,4'-trimethylene-dipiperidine, 1,4-dimethyl-piperazine, benzimidazole, benzoxazole, dipiperidino-methane, tris-(2-(2-methoxyethoxy)-ethyl)amine, and the like, as well as mixtures thereof.

The intermediate compound and the second ester are present in relative amounts such that the second ester is present in a molar excess, i.e., the molar ratio of second ester to amide moiety in the intermediate is greater than 1:1. The relative amounts of second ester and amide moiety in the intermediate are in one embodiment at least about 1.1 moles of second ester per every one mole of amide moiety in the intermediate, in another embodiment at least about 1.2 moles of second ester per every one mole of amide moiety in the intermediate, in yet another embodiment at least about 1.5 moles of second ester per every one mole of amide moiety in the intermediate, and in still another embodiment at least about 2 moles of second ester per every one mole of amide moiety in the intermediate, and in one embodiment no more than about 8 moles of second ester per every one mole of amide moiety in the intermediate, in another embodiment no more than about 4 moles of second ester per every one mole of amide moiety in the intermediate, and in yet another embodiment no more than about 2 moles of second ester per every one mole of amide moiety in the intermediate, although the relative amounts of reactants can be outside of these ranges.

The intermediate compound and the base are present in relative amounts such that the base is present in a molar excess, i.e., the molar ratio of base to amide moiety in the intermediate is greater than 1:1. The relative amounts of base and amide moiety in the intermediate are in one embodiment at least about 1.1 moles of base per every one mole of amide moiety in the intermediate, in another embodiment at least about 1.2 moles of base per every one mole of amide moiety in the intermediate, in yet another embodiment at least about 1.5 moles of base per every one mole of amide moiety in the intermediate, and in still another embodiment at least about 2 moles of base per every one mole of amide moiety in the intermediate, and in one embodiment no more than about 8 moles of base per every one mole of amide moiety in the intermediate, in another embodiment no more than about 4 moles of base per every one mole of amide moiety in the intermediate, and in yet another embodiment no more than about 2 moles of base per every one mole of amide moiety in the intermediate, although the relative amounts of reactants can be outside of these ranges.

The reaction between the intermediate compound and the second ester can take place in the absence of a solvent, or, if desired for reasons such as lowering the viscosity of the product solution, ease of product recovery, or improved control of the reaction temperature, a solvent can be used. Any desired or suitable solvent can be used. Examples of suitable solvents include dimethyl formamide, N-methylpyrrolidinone, toluene, sulfolane, and the like, as well as mixtures thereof.

When present, the solvent is present in any desired or effective amount, in one embodiment at least about 1 mole of intermediate per liter of solvent, in another embodiment at least about 2 moles of intermediate per liter of solvent, and in yet another embodiment at least about 2.5 moles of intermediate per liter of solvent, and is present in an amount of in one embodiment no more than about 10 moles of intermediate per liter of solvent, in another embodiment no more than about 5 moles of intermediate per liter of solvent, and in yet another embodiment no more than about 3.5 moles of intermediate per liter of solvent, although the relative amount of solvent can be outside of these ranges.

The mixture of the intermediate, the base, and the second ester is heated to any desired or effective temperature to effect the conversion to the polypyridone product, in one embodiment to a temperature of at least about 80° C., in another embodiment to a temperature of at least about 100° C., and in yet another embodiment to a temperature of at least about 110° C., and is heated in one embodiment to a temperature of no more than about 160° C., in another embodiment to a temperature of no more than about 140° C., and in yet another embodiment of no more than about 120° C., although the temperature can be outside of these ranges.

The reaction between the intermediate, the base, and the second ester is carried out by heating for any desired or effective amount of time, in one embodiment for a period of at least about 30 minutes, in another embodiment for a period of at least about 60 minutes, and in yet another embodiment for a period of at least about 120 minutes, and in one embodiment for a period of no more than about 1,440 minutes, in another embodiment for a period of no more than about 480 minutes, and in yet another embodiment for a period of no more than about −240 minutes, although the reaction time can be outside of these ranges.

Subsequent to completion of the reaction, the polypyridone product can be recovered by cooling the reaction mixture to room temperature and pouring it into a non-solvent for the polypyridone product. Examples of suitable non-solvents include water, methanol, ethanol, n-propanol, isopropanol, butanol, ethyl acetate, propyl acetate, butyl acetate, and the like, as well as mixtures thereof. For example, mixtures containing from 50 to 80 parts by volume methanol and from 20 to 50 parts by volume water, and more preferably containing from 60 to 80 parts by volume methanol and from 20 to 40 parts by volume water, were found to be particularly effective.

If desired, to convert any polypyridone salt product to the hydroxy form, the non-solvent into which the reaction mixture is poured can be acidified. Any desired or suitable acid can be employed, such as hydrochloric acid, nitric acid, sulfuric acid, and the like, as well as mixtures thereof. In this instance, the acid is present in any desired or effective amount, in one embodiment at least about 1 mole of acid per mole of base used in the synthesis process (including any unreacted polyamine believed to be present from the reaction of the polyamine with the first ester), in another embodiment at least about 1.2 moles of acid per mole of base used in the synthesis process, and in yet another embodiment at least about 1.3 moles of acid per mole of base used in the synthesis process, and in one embodiment no more than about 3 moles of acid per mole of base used in the synthesis process, in another embodiment no more than about 2 moles of acid per mole of base used in the synthesis process, and in yet another embodiment no more than about 1.5 moles of acid per mole of base used in the synthesis process, although the amount of acid can be outside of these ranges.

The precipitated product can then be collected by any desired method, such as filtration or the like, washed, and dried. For washing, a mixture of 50 parts by weight methanol and 50 parts by weight water was found to be particularly effective.

When polymeric products are desired, polymers having three or more pendant primary amino groups, in one embodiment at least about 6 amino groups, and in another embodiment at least about 10 amino groups, and in one embodiment no more than about 30 amino groups, and in another embodiment no more than about 20 amino groups, although the number of amino groups can be outside of these ranges, can be converted to polypyridones by the method described hereinabove. Any desired or effective polymer can be employed, such as commercially available polymers having primary amino groups thereon, polyacrylonitrile which has been reduced, or the like.

While not being limited to any particular theory, it is believed that the ortho-substitution structural feature of the colorant molecules enables the formation of strong intramolecular hydrogen bonds between the azo group, the hydroxyl group, and the carbonyl group that imparts rigidity and significant photostability to the colorant under visible light conditions. It is believed that these bonds form as follows (showing here both the enol and the hydrazone tautomers in which this type of molecule exists, as taught by, for example, "Synthesis of Some Pyridone Azo Dyes from 1-Substituted 2-Hydroxy-6-pyridone Derivatives and their Colour Assessment," C. Chen et al., *Dyes and Pigments*, Vol. 15, p. 69 (1991), the disclosure of which is totally incorporated herein by reference):

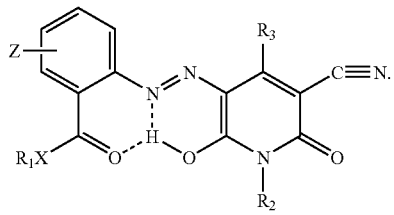

It is believed that this structural feature can also impart thermal stability and chemical stability to the colorant molecule. Further, while not being limited to any particular theory, it is believed that the high molecular weight of the colorant molecule further reduces diffusion or leaching of the colorant molecule from a medium such as a phase change ink vehicle into adjacent inks of different colors (leading to intercolor bleed), adjacent unprinted areas (leading to edge raggedness), directly through the substrate (leading to show through) tape adhesives (leading to edge raggedness and possible illegibility), and the like. Additionally, it is believed that by including multiple azo pyridone chromophores within the colorant molecule, the spectral strength of the colorant is substantially increased, enabling the use of substantially reduced amounts of colorant in, for example, an ink without decreasing the color and the spectral properties (L*a*b*) of the ink or jeopardizing the optical density or color of the prints generated with the ink.

In addition to being suitable for use in phase change inks, the colorants of the present invention can be used in applications such as textile dying, biological dying applications that rely on high spectral strength chromophores, electronics applications, such as organic photoconductors, optical filters, and the like, color filters for liquid crystal display systems, and the like.

Phase change inks as disclosed herein contain a phase change carrier system or composition. The phase change carrier composition is typically designed for use in either a direct printing mode or an indirect or offset printing transfer system.

In the direct printing mode, the phase change carrier composition in one embodiment contains one or more materials that enable the phase change ink (1) to be applied in a thin film of uniform thickness on the final recording substrate (such as paper, transparency material, and the like) when cooled to ambient temperature after printing directly to the recording substrate, (2) to be ductile while retaining sufficient flexibility so that the applied image on the substrate will not fracture upon bending, and (3) to possess a high degree of lightness, chroma, transparency, and thermal stability.

In an offset printing transfer or indirect printing mode, the phase change carrier composition in one embodiment exhibits not only the characteristics desirable for direct printing mode inks, but also certain fluidic and mechanical properties desirable for use in such a system, as described in, for example, U.S. Pat. No. 5,389,958, the disclosure of which is totally incorporated herein by reference.

Any desired or effective carrier composition can be used. Examples of suitable ink carrier materials include fatty amides, such as monoamides, tetra-amides, mixtures thereof, and the like. Specific examples of suitable fatty amide ink carrier materials include stearyl stearamide, a dimer acid based tetra-amide that is the reaction product of dimer acid, ethylene diamine, and stearic acid, a dimer acid based tetra-amide that is the reaction product of dimer acid, ethylene diamine, and a carboxylic acid having at least about 36 carbon atoms, and the like, as well as mixtures thereof. When the fatty amide ink carrier is a dimer acid based tetra-amide that is the reaction product of dimer acid, ethylene diamine, and a carboxylic acid having at least about 36 carbon atoms, the carboxylic acid is of the general formula

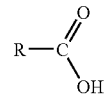

wherein R is an alkyl group, including linear, branched, saturated, unsaturated, and cyclic alkyl groups, said alkyl group in one embodiment having at least about 36 carbon atoms, in another embodiment having at least about 40 carbon atoms, said alkyl group in one embodiment having no more than about 200 carbon atoms, in another embodiment having no more than about 150 carbon atoms, and in yet another embodiment having no more than about 100 carbon atoms, although the number of carbon atoms can be outside of these ranges. Carboxylic acids of this formula are commercially available from, for example, Baker Petrolite, Tulsa, Okla., and can also be prepared as described in Example 1 of U.S. Pat. No. 6,174,937, the disclosure of which is totally incorporated herein by reference. Further information on fatty amide carrier materials is disclosed in, for example, U.S. Pat. Nos. 4,889,560, 4,889,761, 5,194,638, 4,830,671, 6,174,937, 5,372,852, 5,597,856, 6,174,937, and British Patent GB 2 238 792, the disclosures of each of which are totally incorporated herein by reference.

Also suitable as phase change ink carrier materials are isocyanate-derived resins and waxes, such as urethane isocyanate-derived materials, urea isocyanate-derived materials, urethane/urea isocyanate-derived materials, mixtures thereof, and the like. Further information on isocyanate-derived carrier materials is disclosed in, for example, U.S. Pat. Nos. 5,750,604, 5,780,528, 5,782,966, 5,783,658, 5,827,918, 5,830,942, 5,919,839, 6,255,432, 6,309,453, British Patent GB 2 294 939, British Patent GB 2 305 928, British Patent GB 2 305 670, British Patent GB 2 290 793, PCT Publication WO 94/14902, PCT Publication WO 97/12003, PCT Publication WO 97/13816, PCT Publication WO 96/14364, PCT Publication WO 97/33943, and PCT Publication WO 95/04760, the disclosures of each of which are totally incorporated herein by reference.

Mixtures of fatty amide materials and isocyanate-derived materials can also be employed as the ink carrier composition.

Additional suitable phase change ink carrier materials include paraffins, microcrystalline waxes, polyethylene waxes, ester waxes, amide waxes, fatty acids, fatty alcohols, fatty amides and other waxy materials, sulfonamide materials, resinous materials made from different natural sources (such as, for example, tall oil rosins and rosin esters), and many synthetic resins, oligomers, polymers and copolymers, such as ethylene/vinyl acetate copolymers, ethylene/acrylic acid copolymers, ethylene/vinyl acetate/acrylic acid copolymers, copolymers of acrylic acid with polyamides, and the like, ionomers, and the like, as well as mixtures thereof. One or more of these materials can also be employed in a mixture with a fatty amide material and/or an isocyanate-derived material.

In one specific embodiment, the phase change ink carrier comprises (a) a polyethylene wax, present in the ink in an amount in one embodiment of at least about 25 percent by weight of the ink, in another embodiment of at least about 30 percent by weight of the ink, and in yet another embodiment of at least about 37 percent by weight of the ink, and in one embodiment of no more than about 60 percent by weight of the ink, in another embodiment of no more than about 53 percent by weight of the ink, and in yet another embodiment of no more than about 48 percent by weight of the ink, although the amount can be outside of these ranges; (b) a stearyl stearamide wax, present in the ink in an amount in one embodiment of at least about 8 percent by weight of the ink, in another embodiment of at least about 10 percent by weight of the ink, and in yet another embodiment of at least about 12 percent by weight of the ink, and in one embodiment of no more than about 32 percent by weight of the ink, in another embodiment of no more than about 28 percent by weight of the ink, and in yet another embodiment of no more than about 25 percent by weight of the ink, although the amount can be outside of these ranges; (c) a dimer acid based tetra-amide that is the reaction product of dimer acid, ethylene diamine, and a long chain hydrocarbon having greater than thirty six carbon atoms and having a terminal carboxylic acid group, present in the ink in an amount in one embodiment of at least about 10 percent by weight of the ink, in another embodiment of at least about 13 percent by weight of the ink, and in yet another embodiment of at least about 16 percent by weight of the ink, and in one embodiment of no more than about 32 percent by weight of the ink, in another embodiment of no more than about 27 percent by weight of the ink, and in yet another embodiment of no more than about 22 percent by weight of the ink, although the amount can be outside of these ranges; (d) a urethane resin derived from the reaction of two equivalents of hydroabietyl alcohol and one equivalent of isophorone diisocyanate, present in the ink in an amount in one embodiment of at least about 6 percent by weight of the ink, in another embodiment of at least about 8 percent by weight of the ink, and in yet another embodiment of at least about 10 percent by weight of the ink, and in one embodiment of no more than about 16 percent by weight of the ink, in another embodiment of no more than about 14 percent by weight of the ink, and in yet another embodiment of no more than about 12 percent by weight of the ink, although the amount can be outside of these ranges; (e) a urethane resin that is the adduct of three equivalents of stearyl isocyanate and a glycerol-based propoxylate alcohol, present in the ink in an amount in one embodiment of at least about 2 percent by weight of the ink, in another embodiment of at least about 3 percent by weight of the ink, and in yet another embodiment of at least about 4.5 percent by weight of the ink, and in one embodiment of no more than about 13 percent by weight of the ink, in another embodiment of no more than about 10 percent by weight of the ink, and in yet another embodiment of no more than about 7.5 percent by weight of the ink, although the amount can be outside of these ranges; and (f) an antioxidant, present in the ink in an amount in one embodiment of at least about 0.01 percent by weight of the ink, in another embodiment of at least about 0.05 percent by weight of the ink, and in yet another embodiment of at least about 0.1 percent by weight of the ink, and in one embodiment of no more than about 1 percent by weight of the ink, in another embodiment of no more than about 0.5 percent by weight of the ink, and in yet another embodiment of no more than about 0.3 percent by weight of the ink, although the amount can be outside of these ranges.

The ink carrier is present in the phase change ink in any desired or effective amount, in one embodiment of at least about 0.1 percent by weight of the ink, in another embodiment of at least about 50 percent by weight of the ink, and in yet another embodiment of at least about 90 percent by weight of the ink, and in one embodiment of no more than about 99 percent by weight of the ink, in another embodiment of no more than about 98 percent by weight of the ink, and in yet another embodiment of no more than about 95 percent by weight of the ink, although the amount can be outside of these ranges.

The phase change inks contain a colorant compound comprising three or more moieties of the formula

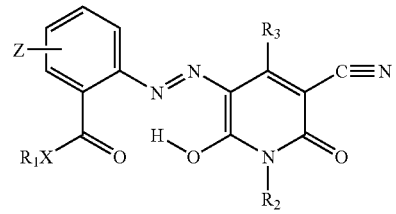

wherein (A) each $R_1$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, or (vi) a siloxy group, (B) each $R_2$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, (vi) a siloxy group, or (vii) a group of the formula

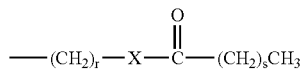

wherein r and s are each, independently of the other, integers representing a number of repeat —CH$_2$— groups, (C) each R$_3$, independently of the others, is (i) an alkyl group, (ii) an aryl group, (iii) an arylalkyl group, or (iv) an alkylaryl group, (D) each X, independently of the others, is (i) a direct bond, (ii) an oxygen atom, (iii) a sulfur atom, (iv) a group of the formula —NR$_{40}$— wherein R$_{40}$ is a hydrogen atom, an alkyl group, an aryl group, an arylalkyl group, or an alkylaryl group, or (v) a group of the formula —CR$_{50}$R$_{60}$— wherein R$_{50}$ and R$_{60}$ each, independently of the other, is a hydrogen atom, an alkyl group, an aryl group, an arylalkyl group, or an alkylaryl group, and (E) each Z, independently of the others, is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

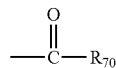

wherein R$_{70}$ is an alkyl group, an aryl group, an arylalkyl group, an alkylaryl group, a silyl group, or a siloxy group, (ix) a sulfonyl group of the formula —SO$_2$R$_{80}$ wherein R$_{80}$ is a hydrogen atom, an alkyl group, an aryl group, an arylalkyl group, an alkylaryl group, a silyl group, or a siloxy group, or (x) a phosphoryl group of the formula —PO$_3$R$_{90}$ wherein R$_{90}$ is a hydrogen atom, an alkyl group, an aryl group, an arylalkyl group, an alkylaryl group, a silyl group, or a siloxy group, said moieties being bonded to a central atom, monomeric group of atoms, oligomer, or polymer. This colorant is present in the ink in any desired or effective amount to obtain the desired color or hue, in one embodiment of at least about 0.1 percent by weight of the ink, in another embodiment of at least about 0.5 percent by weight of the ink, in yet another embodiment of at least about 1 percent by weight of the ink, in still another embodiment of at least about 2 percent by weight of the ink, and in another embodiment of at least about 3 percent by weight of the ink, and in one embodiment of no more than about 20 percent by weight of the ink, in another embodiment of no more than about 13 percent by weight of the ink, and in yet another embodiment of no more than about 6 percent by weight of the ink, although the amount can be outside of these ranges. The colorant as disclosed herein can either be the sole colorant in the ink or can be present in combination with other colorants, such as dyes, pigments, mixtures thereof, and the like.

The inks can also optionally contain an antioxidant. The optional antioxidants of the ink compositions protect the images from oxidation and also protect the ink components from oxidation during the heating portion of the ink preparation process. Specific examples of suitable antioxidants include NAUGUARD® 524, NAUGUARD® 76, and NAUGUARD® 512 (commercially available from Uniroyal Chemical Company, Oxford, Conn.), IRGANOX® 1010 (commercially available from Ciba Geigy), and the like. When present, the optional antioxidant is present in the ink in any desired or effective amount, in one embodiment of at least about 0.01 percent by weight of the ink, in another embodiment of at least about 0.1 percent by weight of the ink, and in yet another embodiment of at least about 1 percent by weight of the ink, and in one embodiment of no more than about 20 percent by weight of the ink, in another embodiment of no more than about 5 percent by weight of the ink, and in yet another embodiment of no more than about 3 percent by weight of the ink, although the amount can be outside of these ranges.

The inks can also optionally contain a viscosity modifier. Examples of suitable viscosity modifiers include aliphatic ketones, such as stearone, and the like. When present, the optional viscosity modifier is present in the ink in any desired or effective amount, in one embodiment of at least about 0.1 percent by weight of the ink, in another embodiment of at least about 1 percent by weight of the ink, and in yet another embodiment of at least about 10 percent by weight of the ink, and in one embodiment of no more than about 99 percent by weight of the ink, in another embodiment of no more than about 30 percent by weight of the ink, and in yet another embodiment of no more than about 15 percent by weight of the ink, although the amount can be outside of these ranges.

Other optional additives to the inks include clarifiers, such as UNION CAMP® X37-523-235 (commercially available from Union Camp), in an amount in one embodiment of at least about 0.01 percent by weight of the ink, in another embodiment of at least about 0.1 percent by weight of the ink, and in yet another embodiment of at least about 5 percent by weight of the ink, and in one embodiment of no more than about 98 percent by weight of the ink, in another embodiment of no more than about 50 percent by weight of the ink, and in yet another embodiment of no more than about 10 percent by weight of the ink, although the amount can be outside of these ranges, tackifiers, such as FORAL® 85, a glycerol ester of hydrogenated abietic (rosin) acid (commercially available from Hercules), FORAL® 105, a pentaerythritol ester of hydroabietic (rosin) acid (commercially available from Hercules), CELLOLYN® 21, a hydroabietic (rosin) alcohol ester of phthalic acid (commercially available from Hercules), ARAKAWA KE-311 and KE-100 Resins, triglycerides of hydrogenated abietic (rosin) acid (commercially available from Arakawa Chemical Industries, Ltd.), synthetic polyterpene resins such as NEVTAC® 2300, NEVTAC® 100, and NEVTAC® 80 (commercially available from Neville Chemical Company), WINGTACK® 86, a modified synthetic polyterpene resin (commercially available from Goodyear), and the like, in an amount in one embodiment of at least about 0.1 percent by weight of the ink, in another embodiment of at least about 5 percent by weight of the ink, and in yet another embodiment of at least about 10 percent by weight of the ink, and in one embodiment of no more than about 98 percent by weight of the ink, in another embodiment of no more than about 75 percent by weight of the ink, and in yet another embodiment of no more than about 50 percent by weight of the ink, although the amount can be outside of these range, adhesives, such as VERSAMID® 757, 759, or 744 (commercially available from Henkel), in an amount in one embodiment of at least about 0.1 percent by weight of the ink, in another embodiment of at least about 1 percent by weight of the ink, and in yet another embodiment of at least about 5 percent by weight of the ink, and in one embodiment of no more than about 98 percent by weight of the ink, in another embodiment of no more than about 50 percent by weight of the ink, and in yet another embodiment of no more than about 10 percent by weight of the ink, although the amount can be outside of these ranges, plasticizers, such as UNIPLEX® 250 (commercially available from Uniplex), the phthalate ester plasticizers commercially available from Monsanto under the trade name SANTICIZER®, such as dioctyl phthalate, diundecyl phthalate, alkylbenzyl phthalate (SANTICIZER® 278), triphenyl phosphate (commercially available from Monsanto), KP-140®, a tributoxyethyl phosphate (commercially available from FMC Corporation), MORFLEX® 150, a dicyclohexyl phthalate (commercially available from Morflex Chemical Company Inc.), trioctyl trimellitate (commercially available from Eastman Kodak Co.), and the like, in an amount in one embodiment of at least about 0.1 percent by weight of the ink, in another embodiment of at least about 1 percent by weight of the ink, and in yet another embodiment of at least about 2 percent by weight of the ink, and in one embodiment of no more than about 50 percent by weight of the ink, in another embodiment of no more than about 30 percent by weight of the ink, and in yet another embodiment of no more than about 10 percent by weight of the ink, although the amount can be outside of these ranges, and the like.

The ink compositions in one embodiment have melting points of no lower than about 50° C., in another embodiment of no lower than about 70° C., and in yet another embodiment of no lower than about 80° C., and have melting points in one embodiment of no higher than about 160° C., in another embodiment of no higher than about 140° C., and in yet another embodiment of no higher than about 100° C., although the melting point can be outside of these ranges.

The ink compositions generally have melt viscosities at the jetting temperature (in one embodiment no lower than about 75° C., in another embodiment no lower than about 100° C., and in yet another embodiment no lower than about 120° C., and in one embodiment no higher than about 180° C., and in another embodiment no higher than about 150° C., although the jetting temperature can be outside of these ranges) in one embodiment of no more than about 30 centipoise, in another embodiment of no more than about 20 centipoise, and in yet another embodiment of no more than about 15 centipoise, and in one embodiment of no less than about 2 centipoise, in another embodiment of no less than about 5 centipoise, and in yet another embodiment of no less than about 7 centipoise, although the melt viscosity can be outside of these ranges.

The ink compositions can be prepared by any desired or suitable method. For example, the ink ingredients can be mixed together, followed by heating, to a temperature in one embodiment of at least about 100° C., and in one embodiment of no more than about 140° C., although the temperature can be outside of these ranges, and stirring until a homogeneous ink composition is obtained, followed by cooling the ink to ambient temperature (typically from about 20 to about 25° C.). The inks are solid at ambient temperature. In a specific embodiment, during the formation process, the inks in their molten state are poured into molds and then allowed to cool and solidify to form ink sticks.

The inks can be employed in apparatus for direct printing ink jet processes and in indirect (offset) printing ink jet applications. Another embodiment disclosed herein is directed to a process which comprises incorporating an ink as disclosed herein into an ink jet printing apparatus, melting the ink, and causing droplets of the melted ink to be ejected in an imagewise pattern onto a recording substrate. A direct printing process is also disclosed in, for example, U.S. Pat. No. 5,195,430, the disclosure of which is totally incorporated herein by reference. Yet another embodiment disclosed herein is directed to a process which comprises incorporating an ink as disclosed herein into an ink jet printing apparatus, melting the ink, causing droplets of the melted ink to be ejected in an imagewise pattern onto an intermediate transfer member, and transferring the ink in the imagewise pattern from the intermediate transfer member to a final recording substrate. In a specific embodiment, the intermediate transfer member is heated to a temperature above that of the final recording sheet and below that of the melted ink in the printing apparatus. An offset or indirect printing process is also disclosed in, for example, U.S. Pat. No. 5,389,958, the disclosure of which is totally incorporated herein by reference. In one specific embodiment, the printing apparatus employs a piezoelectric printing process wherein droplets of the ink are caused to be ejected in imagewise pattern by oscillations of piezoelectric vibrating elements. Inks as disclosed herein can also be employed in other hot melt printing processes, such as hot melt acoustic ink jet printing, hot melt thermal ink jet printing, hot melt continuous stream or deflection ink jet printing, and the like. Phase change inks as disclosed herein can also be used in printing processes other than hot melt ink jet printing processes.

Any suitable substrate or recording sheet can be employed, including plain papers such as XEROX® 4024 papers, XEROX® Image Series papers, Courtland 4024 DP paper, ruled notebook paper, bond paper, silica coated papers such as Sharp Company silica coated paper, JuJo paper, HAMMERMILL LASERPRINT® paper, and the like, transparency materials, fabrics, textile products, plastics, polymeric films, inorganic substrates such as metals and wood, and the like.

Specific embodiments will now be described in detail. These examples are intended to be illustrative, and the claims are not limited to the materials, conditions, or process parameters set forth in these embodiments. All parts and percentages are by weight unless otherwise indicated.

EXAMPLE I

Part A: Dipentaerythritol Hexaanthranilate Synthesis

Into a 1 liter round bottom flask equipped with mechanical stirrer, dropping funnel, and thermometer, was charged dipentaerythritol (76.2 grams, 0.03 mol; obtained from Sigma-Aldrich, Milwaukee, Wis.), isatoic anhydride (342 grams, 2.1 mol; obtained from Sigma-Aldrich), 1,4-diazabicyclo(2.2.2)octane (DABCO) (33 grams, 0.3 mol; obtained from Sigma-Aldrich), and dimethylformamide (500 milliliters). The mixture was stirred and heated to 120° C. for a period of about 16 hours. The mixture was then cooled to room temperature and methanol (2 liters) was added. Deionized water (100 milliliters) was subsequently added, causing the solution to turn cloudy. This solution was stirred for four hours and then filtered, washed with 5×200 milliliters of methanol, and oven dried at 60° C. to yield 135 grams of a beige solid.

Part B: Dodecyl Pyridone Synthesis

Into a 2 liter Erlenmeyer flask equipped with magnetic stirring was charged dodecylamine (185.0 grams, 1.0 mol; obtained from Sigma-Aldrich) followed with ethyl cyanoacetate (ECA, 135.5 grams, 1.20 mol; obtained from Sigma-Aldrich). The mixture was then heated to 140° C. and stirred at this temperature for 1 hour, during which time the ethanol by-product was allowed to distill away. Thereafter, to the hot reaction mixture stirring at 140° C. internal temperature was sequentially added dimethylformamide (DMF; 250 milliliters), ethyl acetoacetate (EAA; 266.0 grams, 2.0 mol; obtained from Sigma-Aldrich), and piperazine (PIP; 129.0 grams, 1.5 mol; obtained from Sigma-Aldrich). The mixture was then heated to 110° C. for 4 hours. The mixture was then allowed to cool to room temperature and was poured slowly into a mixture of deionized water (1,500 milliliters), methanol (3,500 milliliters), and concentrated nitric acid (270.0 grams, 3.0 mol). A white precipitate formed immediately and was allowed to stir at room temperature for 3 hours, and then was filtered and washed with a 70:30 (v/v) mixture of methanol/deionized water (500 milliliters). The precipitate was then oven dried at 60° C. to give 270.5 grams of an off white solid at 85 percent yield.

Part C: Dye Coupling

Into a 500 milliliter round bottom flask equipped with mechanical stirrer, dropping funnel, and thermometer was charged under agitation the hexaanthranilate prepared in Part A above (14.5 grams, 0.015 mol), followed with a prepared solution containing 150 milliliters of glacial acetic acid, 50 milliliters of deionized water, and 10 milliliters of concentrated sulfuric acid. The resulting dark, slightly cloudy solution was chilled to an internal temperature of 5° C. Nitrosylsulfuric acid (NSA, commercial solution containing 40 percent by weight NSA in sulfuric acid, obtained from Sigma-Aldrich Co., Milwaukee, Wis., 29.2 grams, 0.092 mol) was charged into the dropping funnel and then dripped slowly into the solution at a rate whereby the internal temperature was maintained between 0° C. and 10° C. After 15 minutes, the NSA addition was completed and the mixture was stirred for an additional 15 minutes while being cooled at 0° C. An aqueous urea solution (20 milliliters/2 Molar, 0.04 mol) was then added to the mixture to quench any residual NSA reagent and the mixture was stirred for 15 more minutes.

A coupling solution of the dodecyl pyridone prepared in Part B above was prepared in a 2 liter kettle equipped with mechanical stirrer. Into this vessel was charged dodecyl pyridone (31.8 grams, 0.1 mol) prepared as described in Part B above, followed with a solution containing 500 milliliters of isopropanol and 500 milliliters of deionized water. Diethylaminoethanol (39.0 grams, 0.33 mol; obtained from Sigma-Aldrich) was then added, and the solution cleared, leaving a slightly cloudy beige solution.

The cold diazonium salt solution was then slowly poured into the vigorously stirred dodecyl pyridone coupling solution. A bright yellow precipitate formed immediately, and after complete addition of the diazonium salt solution the yellow slurry was stirred for an additional 1 hour.

The yellow slurry thus formed was vacuum filtered and the yellow dye cake was then washed in the funnel with a 50:50 mixture of isopropanol and deionized water (3×250 milliliters) and then water (250 milliliters). The filter cake was then redispersed multiple times in deionized water (250 milliliters), stirred for 30 minutes, and refiltered until the pH of the resulting filtrate was greater than 5.0 and the conductivity of the filtrate was low. The filter cake was given two final rinses with methanol (250 milliliters). The cake was then dried in a vacuum-oven at 40° C. for 36 hours, affording 39.8 grams of the crude product as a bright yellow powder. If desired, this material can be further purified by recrystallization or reprecipitation. The product thus obtained was believed to be of the formula

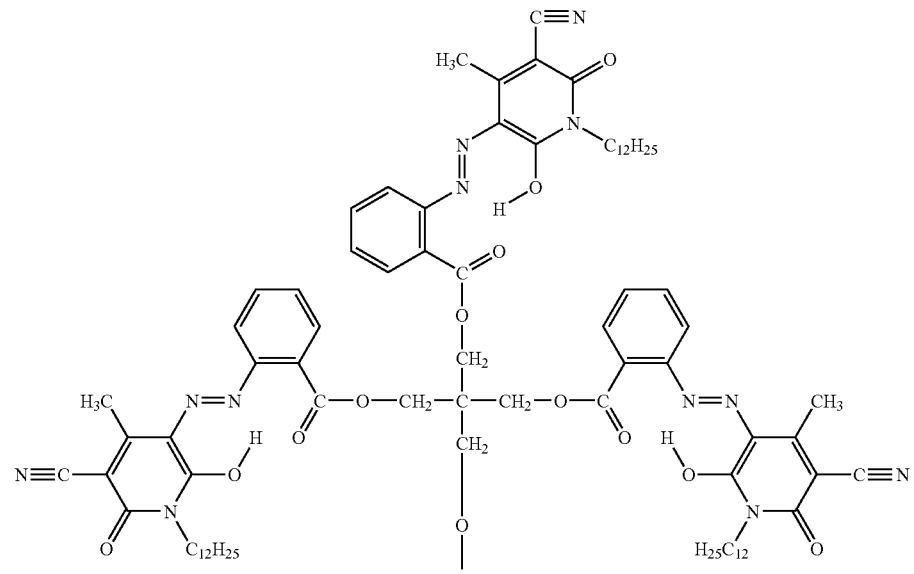

-continued

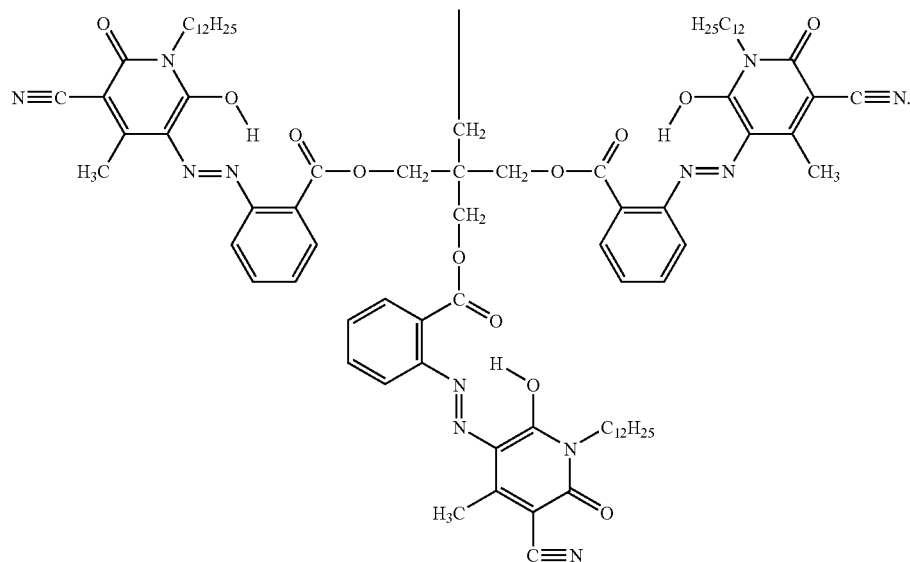

EXAMPLE II

Part A: Pentaerythritol Tetraanthranilate Synthesis

Into a 1 liter round bottom flask equipped with mechanical stirrer, dropping funnel, and thermometer was charged pentaerythritol (68.5 grams, 0.5 mol; obtained from Sigma-Aldrich), isatoic anhydride (407.0 grams, 2.5 mol), 1,4-diazabicyclo(2.2.2)octane (DABCO) (33 grams, 0.3 mol), and dimethylformamide (400 milliliters). The mixture was stirred and heated to 120° C. for a period of about 2 hours. The mixture was then cooled to room temperature and methanol (2 liters) added. Deionized water (300 milliliters) was subsequently added, causing the solution to form a thick suspension. Methanol (700 milliliters) was added to enable stirring of the thick slurry. The solution was stirred for 3 hours and then filtered, washed with 5×200 milliliters of methanol, and oven dried at 60° C. to yield 239 grams of a beige solid at 78 percent yield.

Part B: Stearyl Pyridone Synthesis

Into a 2 liter Erlenmeyer flask equipped with magnetic stirring was charged stearylamine (118 g, 0.44 mol; obtained from Sigma-Aldrich) and ethyl cyanoacetate (ECA, 45.2 grams, 0.4 mol). The mixture was heated to 120° C. for 90 minutes, after which ethyl acetoacetate (EAA, 114 grams, 0.88 mol), piperidine (PIP; 70 grams, 0.82 mol), and dimethylformamide (DMF; 140 milliliters) were added. The mixture was heated to 120° C. for 4 hours. The mixture was then allowed to cool to room temperature and was poured slowly into well stirred methanol (1,200 milliliters), which contained concentrated hydrochloric acid (100 milliliters). The resulting suspension was allowed to stir for 10 minutes, and was then filtered and washed with 3×200 milliliter portions of methanol. The resulting solid was oven dried at 60° C. to give 91.3 grams of a beige powder at 57 percent yield.

Part C: Dye Coupling

Into a 500 milliliter round bottom flask equipped with mechanical stirrer, dropping funnel, and thermometer was charged under agitation tetrakisanthranilate (12.2 grams, 0.02 mol), prepared as described in Part A above, followed with a prepared solution containing 150 milliliters of glacial acetic acid, 50 milliliters of deionized water, and 12 milliliters of concentrated sulfuric acid. The resulting dark, slightly cloudy solution was chilled to an internal temperature of 5° C. Nitrosylsulfuric acid (NSA, commercial solution containing 40 percent by weight NSA in sulfuric acid, obtained from Sigma-Aldrich Co., Milwaukee, Wis., 26.0 grams, 0.082 mol) was charged into the dropping funnel and then dripped slowly into the solution at a rate whereby the internal temperature was maintained between 0° C. and 10° C. After 15 minutes, the NSA addition was completed and the mixture was stirred for an additional-15 minutes while being cooled at 0° C. An aqueous urea solution (20 milliliters/2 Molar, 0.04 mol) was then added to the mixture to quench any residual NSA reagent and the mixture was stirred for 15 more minutes.

A coupling solution of stearyl pyridone was prepared in a 2 liter kettle equipped with mechanical stirrer. Into this vessel was charged stearyl pyridone (30.3 grams, 0.075 mol) prepared as described in Part B above, followed with a solution containing 500 milliliters of isopropanol and 500 milliliters of deionized water. Diethylaminoethanol (39.0 grams, 0.33 mol) was then added, and the solution cleared, leaving a slightly cloudy beige solution.

The cold diazonium salt solution was then slowly poured into the vigorously stirred stearyl pyridone coupling solution. A bright yellow precipitate was formed immediately, and after complete addition of the diazonium salt solution, the yellow slurry was stirred for an additional 1 hour.

The yellow slurry was vacuum filtered, and the yellow dye cake was then washed in the funnel with a 50:50 mixture of isopropanol and deionized water (3×250 milliliters) and then water (250 milliliters). The filter cake was then redispersed multiple times in deionized water (250 milliliters), stirred for 30 minutes, and filtered until the pH of the resulting filtrate was greater than 5.0 and the conductivity of the filtrate was low. The filter cake was given two final rinses with methanol (250 milliliters). The cake was then dried in a vacuum-oven at 40° C. for 36 hours, affording, 39.5 grams of the crude product as a dull yellow powder. If desired, this material can be further purified by recrystallization or reprecipitation. The product thus obtained was believed to be of the formula

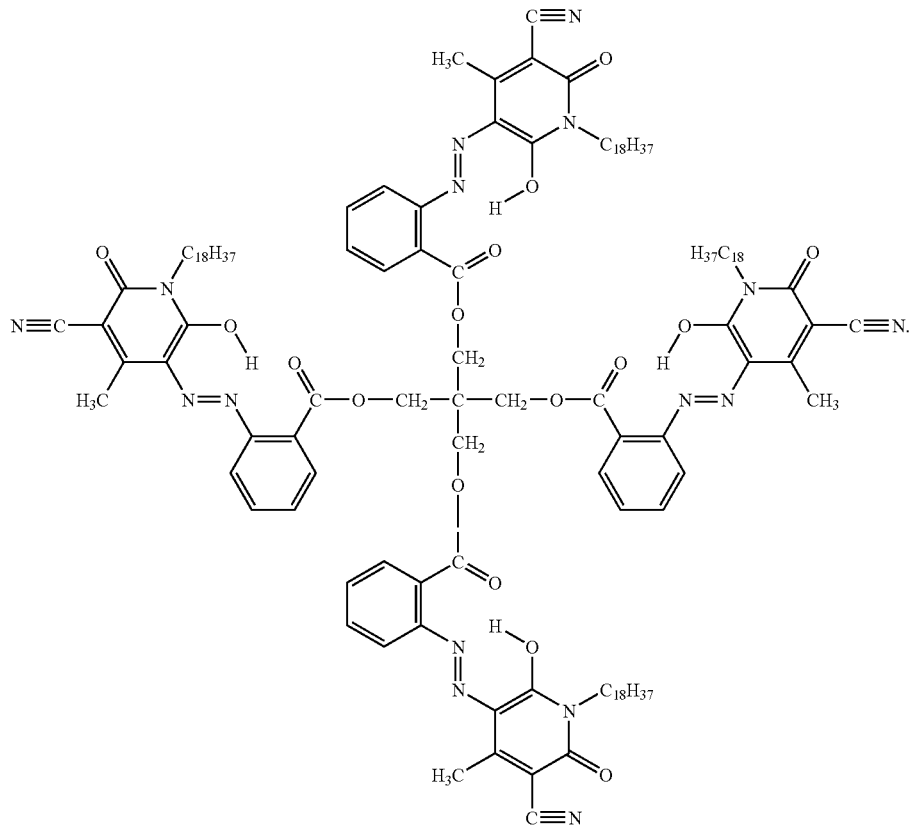

EXAMPLE III

Part A: Dipentaerythritol Hexaanthranilate Synthesis

The anthranilate was prepared as described in Part A of Example I.

Part B: Stearyl Pyridone Synthesis

The pyridone was prepared as described in Part B of Example II.

Part C: Dye Coupling

Into a 500 milliliter round bottom flask equipped with mechanical stirrer, dropping funnel, and thermometer was charged under agitation the hexaanthranilate (14.5 grams, 0.015 mol), prepared as described in Part A of Example I, followed with a prepared solution containing 150 milliliters of glacial acetic acid, 50 milliliters of deionized water, and 15 milliliters of concentrated sulfuric acid. The resulting dark, slightly cloudy solution was chilled to an internal temperature of 5° C. Nitrosylsulfuric acid (NSA, commercial solution containing 40 percent by weight NSA in sulfuric acid, obtained from Sigma-Aldrich Co., Milwaukee, Wis., 29.2 grams, 0.092 mol) was charged into the dropping funnel and then dripped slowly into the solution at a rate whereby the internal temperature was maintained between 0° C. and 10° C. After 15 minutes, the NSA addition was completed and the mixture was stirred for an additional 15 minutes while being cooled at 0° C. An aqueous urea solution (20 milliliters/2 Molar, 0.04 mol) was then added to the mixture to quench any residual NSA reagent and the mixture was stirred for 15 more minutes.

A coupling solution of stearyl pyridone was prepared in a 2 liter kettle equipped with mechanical stirrer. Into this vessel was charged stearyl pyridone (42.6 grams, 0.079 mol) prepared as described in Part B of Example II, followed with a solution consisting of 500 milliliters of isopropanol and 500 milliliters of deionized water. Diethylaminoethanol (39.0 grams, 0.33 mol) was then added and the solution cleared, leaving a slightly cloudy brown solution.

The cold diazonium salt solution was then slowly poured into the vigorously stirred stearyl pyridone coupling solution. A bright yellow precipitate formed immediately, and after complete addition of the diazonium salt solution the yellow slurry was stirred an additional 1 hour.

The yellow slurry was vacuum filtered, and the yellow dye cake was then washed in the funnel with a 50:50 mixture of isopropanol and deionized water (3×250 milliliters) and then water (250 milliliters). The filter cake was then redispersed multiple times in deionized water (250 milliliters), stirring for 30 minutes, and filtered until the pH of the resulting filtrate was greater than 5.0 and the conductivity of the filtrate was low. The filter cake was given two final rinses with methanol (250 milliliters). The cake was then dried in a vacuum-oven at 40° C. for 36 hours, affording 44.1 grams of the crude product as a bright yellow powder. If desired, this material can be further purified by recrystallization or reprecipitation. The product thus obtained was believed to be of the formula liters) was added. A thick white precipitate formed, which was filtered and then washed with 3×1 liter portions of methanol and oven dried at 60° C. to yield 295.8 grams of a beige solid at 76 percent yield.

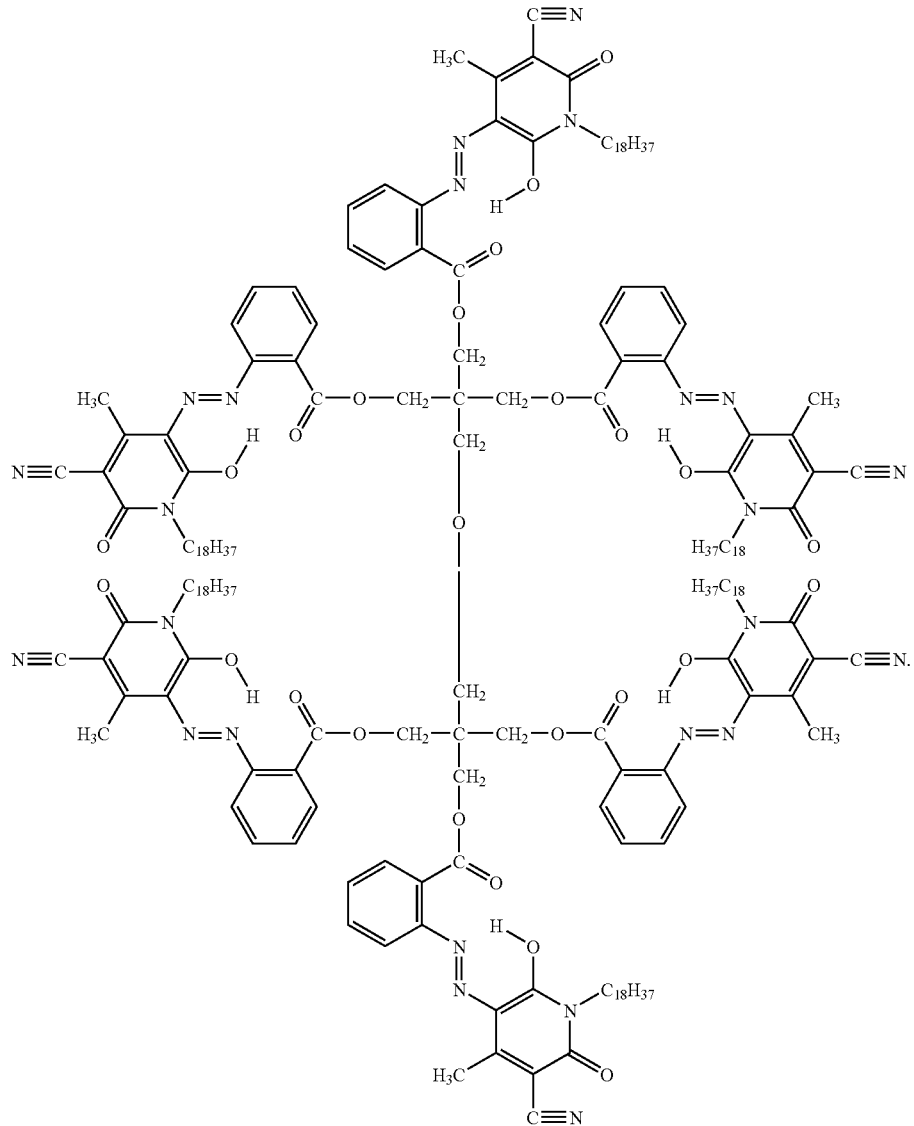

EXAMPLE IV

Part A: Stearyl Anthranilate Synthesis

Into a 4 liter beaker equipped with magnetic stirrer, dropping funnel, and thermometer, was charged stearyl alcohol (270.0 grams, 1.0 mol; obtained from Sigma-Aldrich), isatoic anhydride (244.0 grams, 1.5 mol), 1,4-diazabicyclo(2.2.2)octane (DABCO) (56 grams, 0.5 mol), and dimethylformamide (750 milliliters). The mixture was stirred and heated to 120° C. for a period of about 2 hours. The mixture was then cooled to 50° C., and methanol (3

Part B: Tripyridone Synthesis

Into a 125 milliliter Erlenmeyer flask equipped with magnetic stirring was charged tris(2-aminoethyl)amine (48.0 g, 0.33 mol; obtained from Sigma-Aldrich) and ethyl cyanoacetate (ECA, 135.0 grams, 1.20 mol). The mixture was then heated to 150° C. and stirred at this temperature for 1 hour, during which time the ethanol by-product was allowed to distill away (~15 milliliters). To the hot reaction mixture was sequentially added ethyl acetoacetate (EAA, 390.0 grams, 3.0 mol), piperazine (PIP; 172.0 grams, 2.0 mol) and dimethylformamide (300 milliliters). The mixture was then heated to 120° C. for 5 hours, cooled, and then poured slowly into a mixture of deionized water (700 milliliters), methanol (2,100 milliliters), and concentrated nitric acid (258 grams, 4.0 mol). A white precipitate formed immediately, and the precipitate was allowed to stir at room temperature for 3 hours, and then was filtered and washed with a 50:50 (v/v) mixture of methanol/deionized water (5×500 milliliters). The precipitate was then oven dried at 60° C. to give 130 grams of an off white solid at 72 percent yield.

Part C: Dye Coupling

Into a 500 milliliter round bottom flask equipped with mechanical stirrer, dropping funnel, and thermometer was charged under agitation the stearyl anthranilate (35.8 grams, 0.092 mol) prepared as described in Part A above, followed with a prepared solution containing 100 milliliters of glacial acetic acid, 100 milliliters of dodecylbenzenesulfonic acid, and 50 milliliters of propionic acid (obtained from Sigma-Aldrich). The resulting dark, slightly cloudy solution was chilled to an internal temperature of 5° C. Nitrosylsulfuric acid (NSA, commercial solution containing 40 percent by weight NSA in sulfuric acid, obtained from Sigma-Aldrich Co., Milwaukee, Wis., 28.3 grams, 0.089 mol) was charged into the dropping funnel and then dripped slowly into the solution at a rate whereby the internal temperature was maintained between 0° C. and 10° C. After 15 minutes, the NSA addition was completed and the mixture was stirred for an additional 15 minutes while being cooled at 0° C. An aqueous urea solution (20 milliliters/2 Molar, 0.04 mol) was then added to the mixture to quench any residual NSA reagent and the mixture was stirred for 15 more minutes.

A coupling solution of tripyridone was prepared in a 2 liter kettle equipped with mechanical stirrer. Into this vessel was charged tripyridone (16.35 grams, 0.03 mol) prepared as described in Part B above, followed with a solution consisting of 650 milliliters of isopropanol and 250 milliliters of deionized water. Diethylaminoethanol (23.1 grams, 0.2 mol) was then added, and the solution cleared, leaving a slightly cloudy brown solution.

The cold diazonium salt solution was then slowly poured into the vigorously stirred tripyridone coupling solution. A bright yellow precipitate was formed immediately, and after complete addition of the diazonium salt solution, the yellow slurry was stirred for an additional 1 hour.

The resulting yellow slurry was vacuum filtered and the yellow dye cake was then washed in the funnel with a 50:50 mixture of isopropanol and deionized water (3×250 milliliters) and then water (250 milliliters). The filter cake was then redispersed multiple times in deionized water (250 milliliters), stirred for 30 minutes, and filtered until the pH of the resulting filtrate was greater than 5.0 and the conductivity of the filtrate was low. The filter cake was given two final rinses with methanol (250 milliliters). The cake was then dried in a vacuum-oven at 40° C. for 36 hours, affording 52.8 grams of the crude product as a bright yellow powder. If desired, this material can be further purified by recrystallization or reprecipitation. The product thus obtained was believed to be of the formula

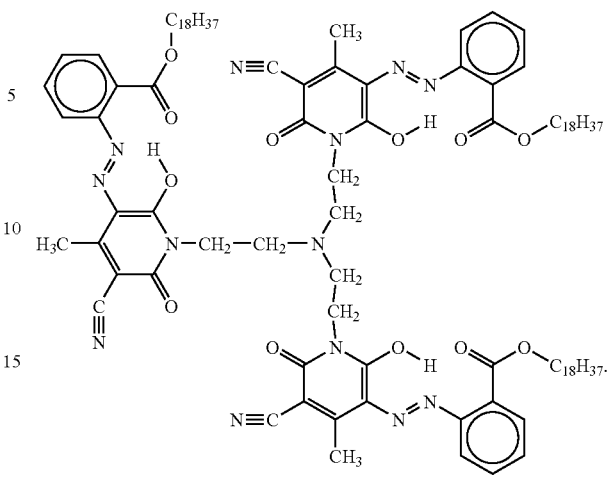

EXAMPLE V

Part A: Triethanolamine Trianthranilate Synthesis

Into a 1 liter round bottom flask-equipped with mechanical stirrer, dropping funnel, and thermometer was charged triethanolamine (149.2 grams, 1.0 mol; obtained from Sigma-Aldrich), isatoic anhydride (520.0 grams, 3.5 mol), 1,4-diazabicyclo(2.2.2)octane (DABCO) (45.0 grams, 0.4 mol), and dimethylformamide (1,500 milliliters). The mixture was stirred and heated to 120° C. for a period of about 2 hours. The mixture was then cooled to room temperature, and methanol (2 liters) was added. Deionized water (1 liter) was added, causing the solution to turn cloudy. This solution was stirred for 2 hours, and then filtered, washed with 5×250 milliliters of methanol, and oven dried at 60° C. to yield 506 grams of a beige solid.

Part B: Stearyl Pyridone Synthesis

The pyridone was prepared as described in Part B of Example II.

Part C: Dye Coupling

Into a 500 milliliter round bottom flask equipped with mechanical stirrer, dropping funnel, and thermometer was charged under agitation the trianthranilate (15.2 grams, 0.03 mol) prepared as described in Part A, followed with a prepared solution containing 96 milliliters of glacial acetic acid, 40 milliliters of deionized water, and 25 milliliters of concentrated sulfuric acid. The resulting dark, slightly cloudy solution was chilled to an internal temperature of 5° C. Nitrosylsulfuric acid (NSA, commercial solution containing 40 percent by weight NSA in sulfuric acid, obtained from Sigma-Aldrich Co., Milwaukee, Wis., 28.3 grams, 0.089 mol) was charged into the dropping funnel and then dripped slowly into the solution at a rate whereby the internal temperature was maintained between 0° C. and 10° C. After 15 minutes, the NSA addition was completed and the mixture was stirred for an additional 15 minutes while being cooled at 0° C. An aqueous urea solution (20 milliliters/2 Molar, 0.04 mol) was then added to the mixture to quench any residual NSA reagent and the mixture was stirred for 15 more minutes.

A coupling solution of stearyl pyridone was prepared in a 2 liter kettle equipped with mechanical stirrer. Into this vessel was charged stearyl pyridone (37.4 grams, 0.092 mol) prepared as described in Part B of Example II, followed with a solution containing 250 milliliters of isopropanol and 250 milliliters of deionized water. Diethylaminoethanol (26.0 grams, 0.22 mol) was then added, and the solution cleared, leaving a slightly cloudy brown solution.

The cold diazonium salt solution was then slowly poured into the vigorously stirred stearyl pyridone coupling solution. A bright yellow precipitate formed immediately, and after complete addition of the diazonium salt solution, the yellow slurry was stirred an additional 1 hour.

The yellow slurry was vacuum filtered, and the yellow dye cake was then washed in the funnel with a 50:50 mixture of isopropanol and deionized water (3×250 milliliters) and then water (250 milliliters). The filter cake was then redispersed multiple times in deionized water (250 milliliters), stirred for 30 minutes, and filtered until the pH of the resulting filtrate was greater than 5.0 and the conductivity of the filtrate was low. The filter cake was given two final rinses with methanol (250 milliliters). The cake was then dried in a vacuum-oven at 40° C. for 36 hours, affording 55.1 grams of the crude product as a bright yellow powder. If desired, this material can be further purified by recrystallization or reprecipitation. The product thus obtained was believed to be of the formula Part B: Dodecyl Pyridone Synthesis The pyridone is prepared as described in Part B of Example I.

Part C: Dye Coupling

Diazo coupling is effected by the procedure described in Example I, using approximately stoichiometrically equivalent amounts of anthranilate and pyridone moieties, to form a polymeric compound having pendant therefrom from about 6 to about 30 groups of the formula

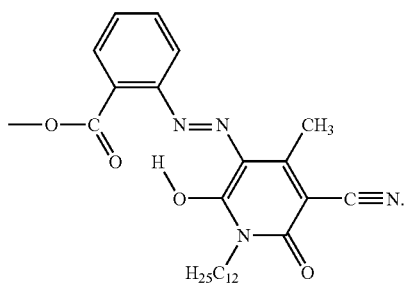

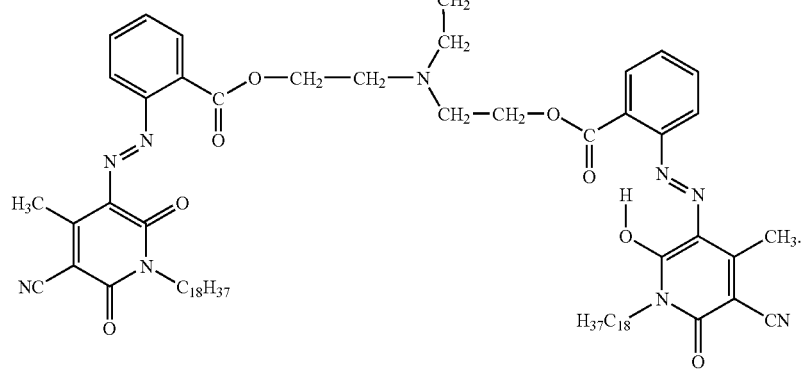

EXAMPLE VI

Part A: Polyanthranilate Synthesis

A polyanthranilate is prepared as described in Part A of Example I except that poly(vinyl alcohol) is used instead of dipentaerythritol, said poly(vinyl alcohol) having from about 6 to about 30 pendant hydroxyl groups. Stoichiometry of the additional reagents is modified accordingly. The resulting product has from about 6 to about 30 pendant anthranilate groups.

EXAMPLE VII

Part A: Stearyl Anthranilate Synthesis

The pyridone is prepared as described in Part A of Example IV.

Part B: Polypyridone Synthesis

A polypyridone is prepared as in Part A of Example IV except that poly(vinylamine) is used instead of dodecyl aniline, said poly(vinylamine) having from about 6 to about 30 pendant —NH$_2$ groups. Stoichiometry of the additional reagents is modified accordingly. The resulting product has from about 6 to about 30 pendant pyridone groups.

Part C: Dye Coupling

Diazo coupling is effected by the procedure described in Example IV, using approximately stoichiometrically equivalent amounts of anthranilate and pyridone moieties, to form a polymeric compound having pendant therefrom from about 6 to about 30 groups of the formula

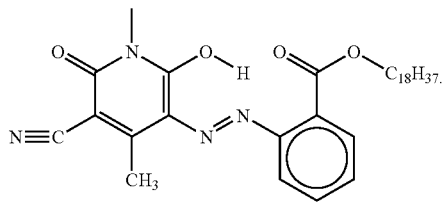

INK EXAMPLE 1

A phase change ink is prepared as follows. In a stainless steel beaker are combined 430 grams of polyethylene wax (PE 655, available from Baker Petrolite, Tulsa, Okla., of the formula $CH_3(CH_2)_{50}CH_3$), 194 grams of stearyl stearomide wax (KEMAMIDE® S-180, available from Crompton Corporation, Greenwich, Conn.), 219 grams of a tetra-amide resin obtained from the reaction of one equivalent of a C-36 dimer acid available from Uniqema, New Castle, Del. with two equivalents of ethylene diamine and UNICID® 700 (available from Baker Petrolite, Tulsa, Okla., a long chain hydrocarbon having a terminal carboxylic acid group), prepared as described in Example 1 of U.S. Pat. No. 6,174,937, the disclosure of which is totally incorporated herein by reference, 77 grams of a urethane resin obtained from the reaction of two equivalents of ABITOL® E hydroabietyl alcohol (available from Hercules Inc., Wilmington, Del.) and one equivalent of isophorone diisocyanate, prepared as described in Example 1 of U.S. Pat. No. 5,782,966, the disclosure of which is totally incorporated herein by reference, 46 grams of a urethane resin that is the adduct of three equivalents of stearyl isocyanate and a glycerol-based alcohol, prepared as described in Example 4 of U.S. Pat. No. 6,309,453, the disclosure of which is totally incorporated herein by reference, and 2.0 gram of NAUGUARD® 445 antioxidant (available from Uniroyal Chemical Co., Middlebury, Conn.). The materials are melted together at a temperature of about 140° C. in an oven, then blended by stirring in a temperature controlled mantle at about 135° C. for about 0.5 hour. To this mixture is then added about 20 grams of the colorant prepared as described in Example I. After stirring for about 3 additional hours, the yellow ink thus formed is filtered through a heated MOTTO apparatus (obtained from Mott Metallurgical) using #3 Whatman filter paper and a pressure of about 15 pounds per square inch. The filtered phase change ink is poured into molds and allowed to solidify to form ink sticks.

INK EXAMPLES 2 TO 7

The process of Ink Example 1 is repeated except that the colorants of Examples II through VII are substituted for the colorant of Example I.

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A phase change ink composition comprising a phase change ink carrier and a colorant compound comprising three or more moieties of the formula

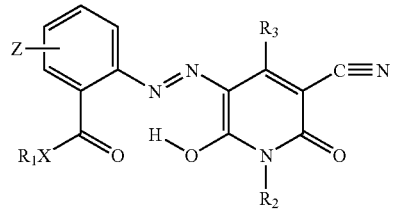

wherein (A) each $R_1$, independently of the others, is (i) an alkyl or alkylene group, including linear, branched, saturated, unsaturated, cyclic, unsubstituted, and substituted alkyl and alkylene groups, and wherein hetero atoms either may or may not be present in the alkyl or alkylene group, (ii) an aryl or arylene group, including unsubstituted and substituted aryl and arylene groups, and wherein hetero atoms either may or may not be present in the aryl or arylene group, (iii) an arylalkyl or arylalkylene group, including unsubstituted and substituted arylalkyl and arylalkylene groups, and wherein hetero atoms either may or may not be present in either or both of the aryl portion and the alkyl portion of the arylalkyl or arylalkylene group, (iv) an alkylaryl or alkylarylene group, including unsubstituted and sustituted alkylaryl and alkylarylene groups, and wherein hetero atoms either may or may not be present in either or both of the aryl portion and the alkyl portion of the alkylaryl or alkylarylene group, (v) a silyl and silylene groups, and including polysilylene groups, or (vi) a siloxy group, including unsubstituted and substituted siloxy groups, and including polysiloxane groups, (B) each $R_2$, independently of the others, is (i) an alkyl or alkylene group, including linear, branched, saturated, unsaturated, cyclic, unsubstituted, and substituted alkyl and alkylene groups, and wherein hetero atoms either may or may not be present in the alkyl or alkylene group, (ii) an aryl or arylene group, including unsubstituted and substituted aryl and arylene groups, and wherein hetero atoms either may or may not be present in the aryl or arylene group, (iii) an arylalkyl or arylalkylene group, including unsubstituted and substituted arylalkyl and arylalkylene groups, and wherein hetero atoms either may or may not be present in either or both of the and portion and the alkyl portion of the arylalkyl or arylalkylene group, (iv) an alkylaryl or alkylarylene group, including unsubstituted and substituted alkylaryl and alkylarylene groups, and wherein hetero atoms either may or may not be present in either or both of the aryl portion and the alkyl portion of the alkylaryl or alkylarylene group, (v) a silyl or silylene group, including unsubstituted and substituted silyl and silylene groups, and including polysilylene groups, (vi) a siloxy group, including unsubstituted and substituted siloxane groups, and including polysiloxane groups, (vii) a group of the formula

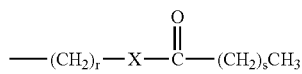

wherein r and s are each, independently of the other, integers representing a number of repeat —CH$_2$— groups, (C) each R$_3$, independently of the others, is (i) an alkyl group, including linear, branched, saturated, unsaturated, cyclic, unsubstituted, and substituted alkyl groups, and wherein hetero atoms either may or may not be present in the alkyl group, (ii) an aryl group, including unsubstituted and substituted aryl groups, and wherein hetero atoms either may or may not be present in the arly group, (iii) an arylalkyl group, including unsubstituted and substituted arylalkyl groups, and wherein hetero atoms either may or may not be present in either or both of the aryl portion and the alkyl portion of the arylalkyl group, or (iv) an alkylaryl group, including unsubstituted and substituted alkylaryl groups, and wherein hetero atoms either may or may not be present in either or both of the aryl portion and the alkyl portion of the alkylaryl group, (D) each X, independently of the others, is (i) a direct bond, (ii) an oxygen atom, (iii) a sulfur atom, (iv) a group of the formula —NR$_{40}$— wherein R$_{40}$ is a hydrogen atom, an alkyl group, including linear, branched, saturated, unsaturated, cyclic, unsubstituted, and substituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in either or both of the aryl portion and the alkyl portion of the arylalkyl group, or an alkylaryl group, including substituted alkylaryl and unsubstituted groups, and wherein hetero atoms either may or may not be present in either or both of the aryl portion and the alkyl portion of the arylalkyl group, or (v) a group of the formula —CR$_{50}$R$_{60}$— wherein R$_{50}$ and R$_{60}$ each, independently of the other, is a hydrogen atom, an alkyl group, including linear, branched, saturated, unsaturated, cyclic, unsubstituted, and substituted alkyl groups, and wherein hetero atoms either may or may not be present in the alkyl group, an aryl group, including substituted and unsubstituted and groups, and wherein hetero atoms either may or may not be present in the aryl group, an arylalkyl group, including substituted and unsubstituted arylalkyl groups, and wherein hetero atoms either may or may not be present in either or both of the aryl portion and the alkyl portion of the arylalkyl group, or an alkylaryl group, including substituted and unsubstituted alkylaryl groups, and wherein hetero atoms either may or may not be present in either or both of the aryl portion and the alkyl portion of the alkylaryl group, and (E) each Z, independently of the others, is (i) a hydrogen atom, (ii) a halogen atom, (iii) a nitro group, (iv) an alkyl group, including linear, branched, saturated, unsaturated, cyclic, unsubstituted, and substituted alkyl groups, and wherein hetero atoms either may or may not be present in the alkyl group, (v) an aryl group, including substituted and unsubstituted aryl groups, and wherein hetero atoms either may or may not be present in the aryl group, (vi) an arylalkyl group, including substituted and unsubstituted arylalkyl groups, and wherein hetero atoms either may or may not be present in either or both of the aryl portion and the alkyl portion of the arylalkyl group, (vii) an alkylaryl group, including substituted and unsubstituted alkylaryl groups, and wherein hetero atoms either may or may not be present in either or both of the aryl portion and the alkyl portion of the alkylaryl group, (viii) a group of the formula

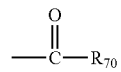

wherein R$_{70}$ is an alkyl group, including linear, branched, saturated, unsaturated, cyclic, unsubstituted, and substituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in either or both of the and portion and the alkyl portion of the arylalkyl group, an alkylaryl group, including substituted and unsubstituted alkylaryl groups, and wherein hetero atoms either may or may not be present in either or both of the aryl portion and the alkyl portion of the alkylaryl group, a silyl group, including unsubstituted and substituted silyl groups, and including polysilylene groups, or a siloxy group, including unsubstituted and substituted siloxy groups, and including polysiloxane groups, (ix) a sulfonyl group of the formula —SO$_2$R$_{80}$ wherein R$_{80}$ is a hydrogen atom, an alkyl group, including linear, branched, saturated, unsaturated, cyclic, unsubstituted, and substituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in either or both of the aryl portion and the alkyl portion of the arylalkyl group, an alkylaryl group, including substituted and unsubstituted alkylaryl groups, and wherein hetero atoms either may or may not be present in either or both of the and portion and the alkyl portion of the alkylaryl group, a silyl group, including unsubstituted and substituted silyl groups, and including polysilylene groups, or a siloxy group, including unsubstituted and substituted siloxy groups, and including polysiloxane groups, or (x) a phosphoryl group of the formula —PO$_{30}$R$_{90}$ wherein R$_{90}$ is a hydrogen atom, an alkyl group, including linear, branched, saturated, unsaturated, cyclic, unsubstituted, and substituted alkyl groups, and wherein hetero atoms either may or may not be present in the alkyl group, an aryl group, including substituted and unsubstituted aryl groups, and wherein hetero atoms either may or may not be present in the aryl group, an arylalkyl group, including substituted and unsubstituted arylalkyl groups, and wherein hetero atoms either may or may not be present in either or both of the aryl portion and the alkyl portion of the arylalkyl group, an alkylaryl group, including substituted and unsubsiltuted alkylaryl groups, and wherein hetero atoms either may or may not be present in either or both of the aryl portion and the alkyl portion of the alkylaryl group, a silyl group, including unsubstituted and substituted silyl groups, and including polysilylene groups, or a siloxy group, including unsubstituted and substituted siloxy groups, and including polysiloxane groups; said moieties being bonded to a central atom, monomeric group of atoms, oligomer, or polymer.

2. A phase change ink according to claim 1 wherein the colorant compound contains four or more moieties of the formula

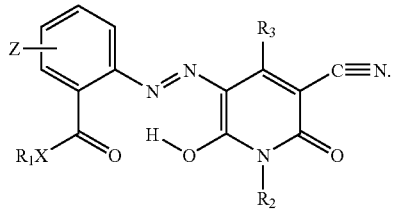

3. A phase change ink according to claim 1 wherein the moieties are linked to the central atom or group of atoms or bonded to the polymer through the R₁ group and wherein the moieties are of the formula

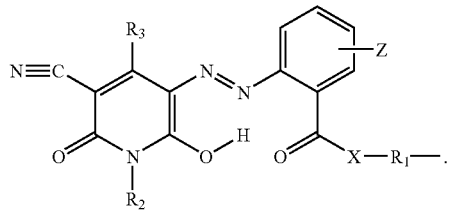

4. A phase change ink according to claim 1 wherein the moieties are linked to the central atom or group of atoms or bonded to the polymer through the R₂ group and wherein the moieties are of the formula

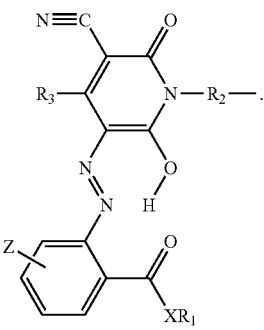

5. A phase change ink according to claim 1 wherein the moieties are bonded to a single central atom.

6. A phase change ink according to claim 5 wherein the colorant is of the formula

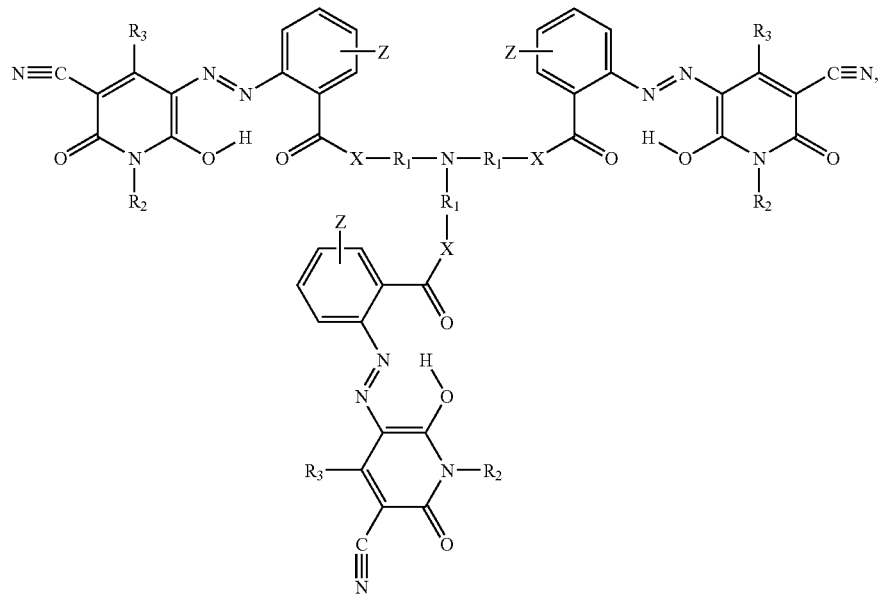

-continued
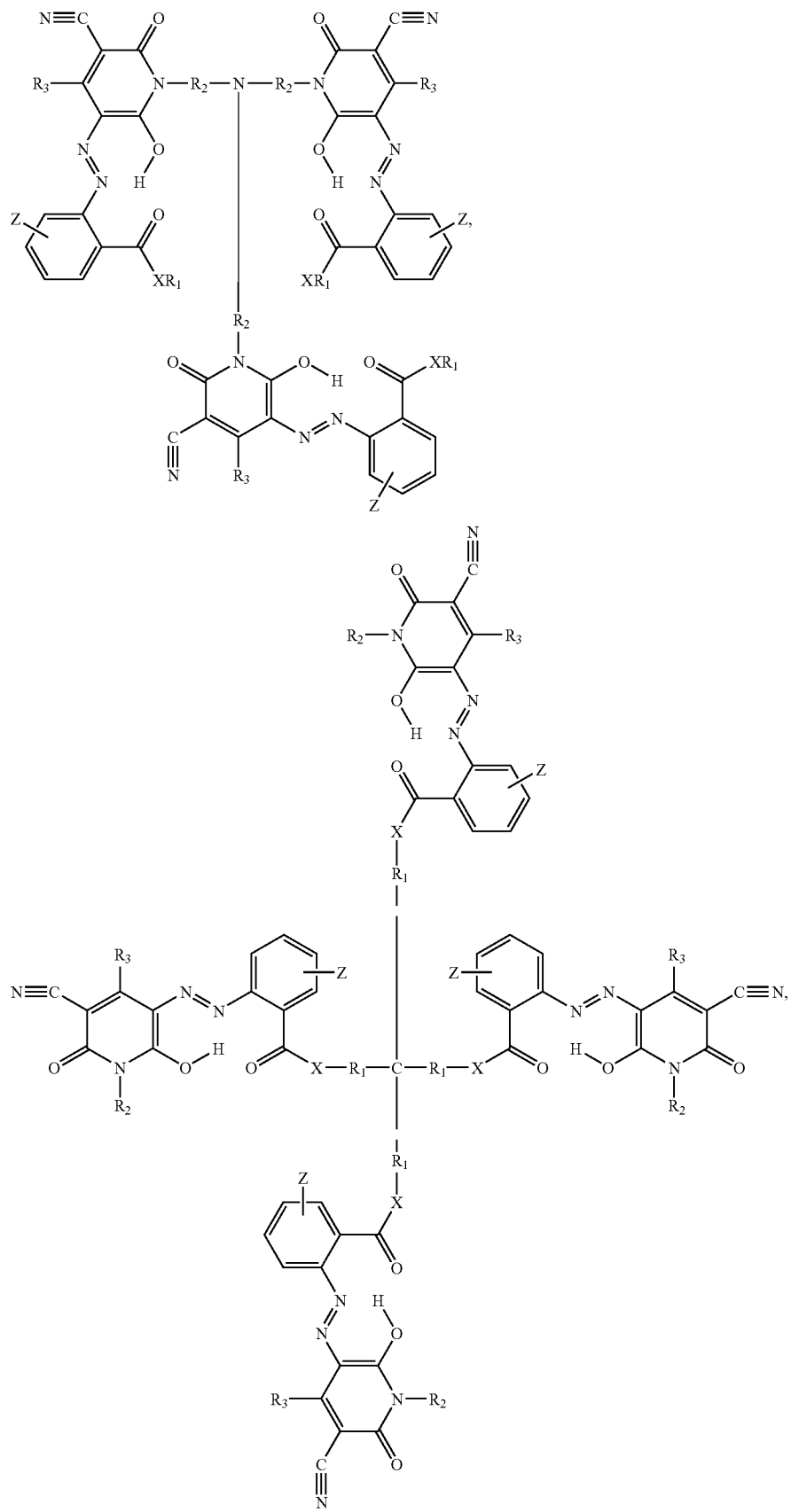

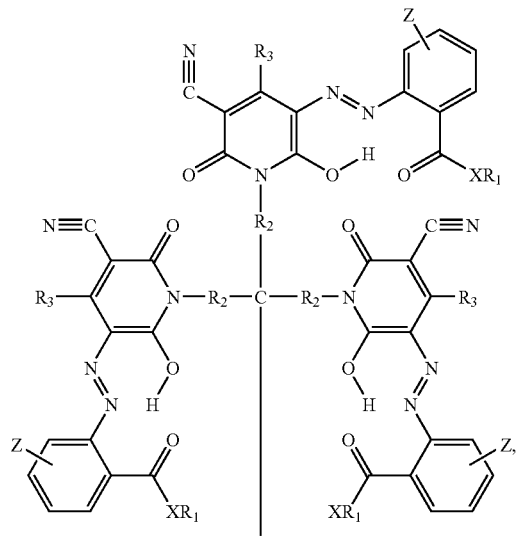
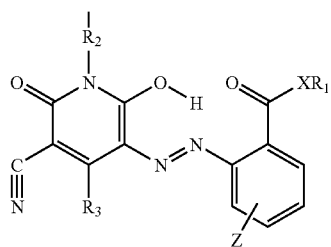
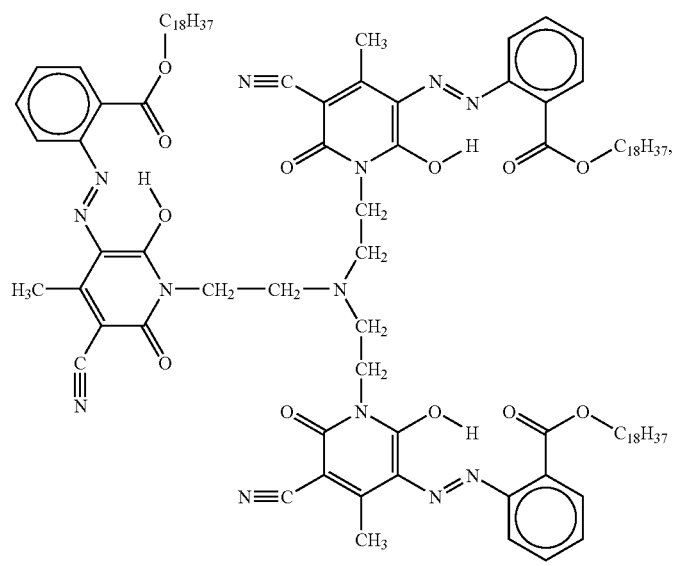

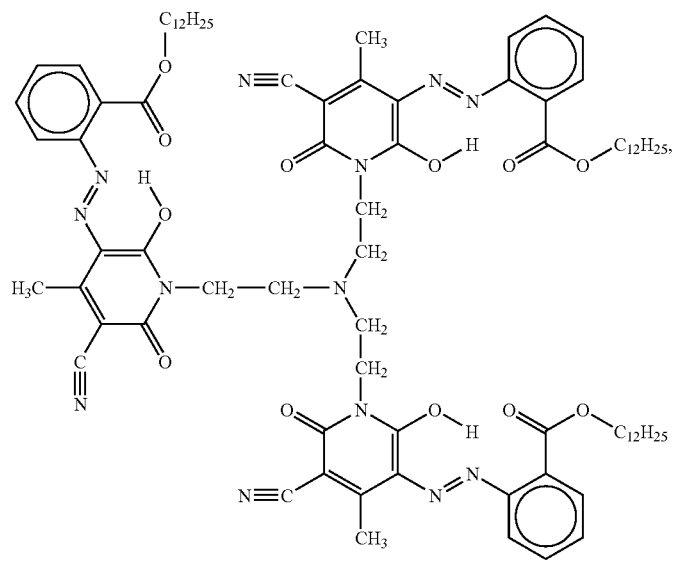
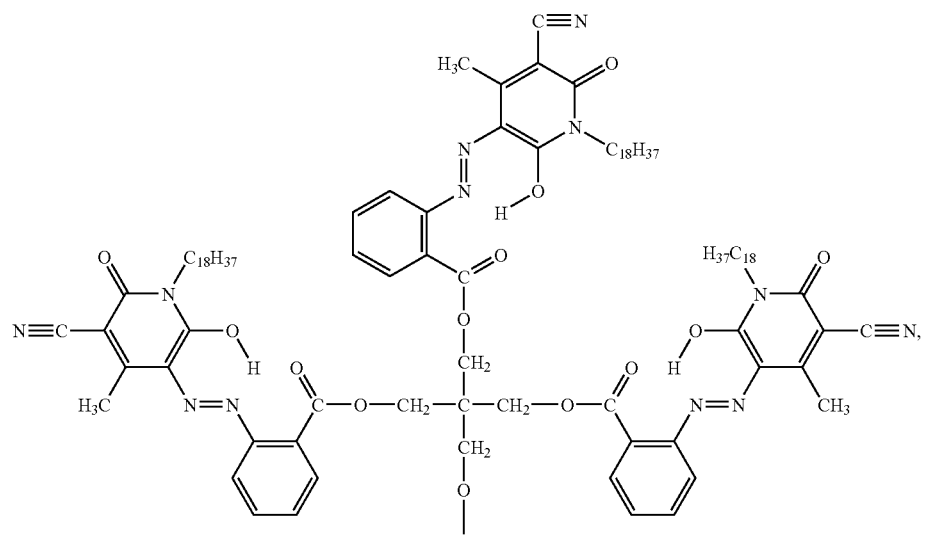
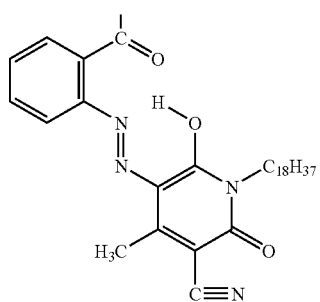

-continued
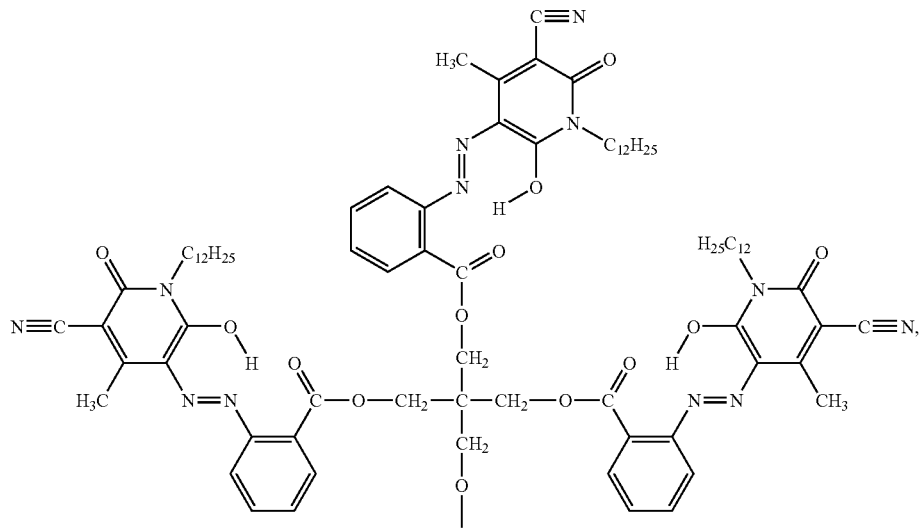
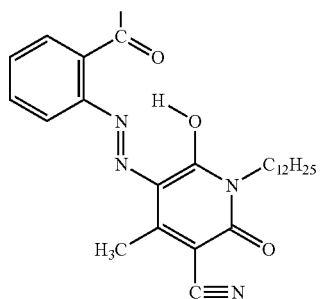
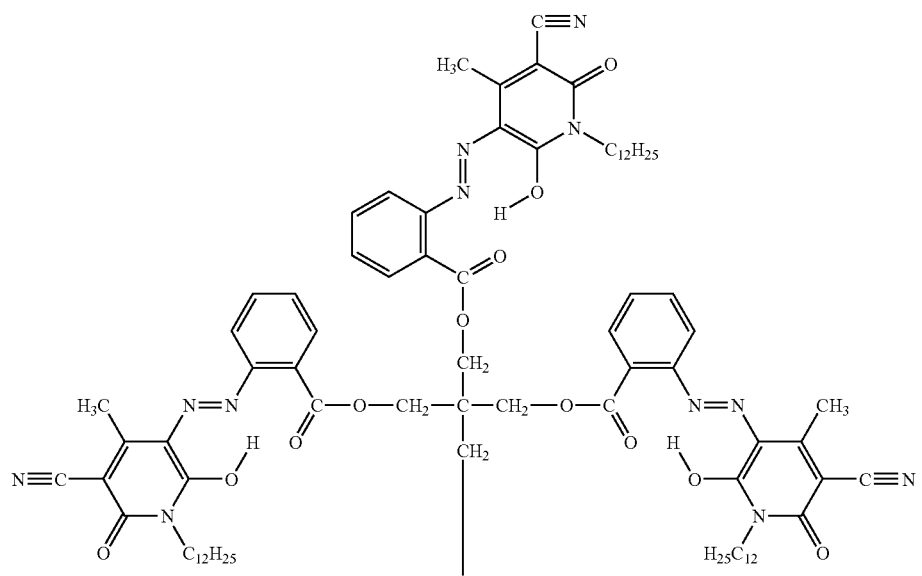

-continued
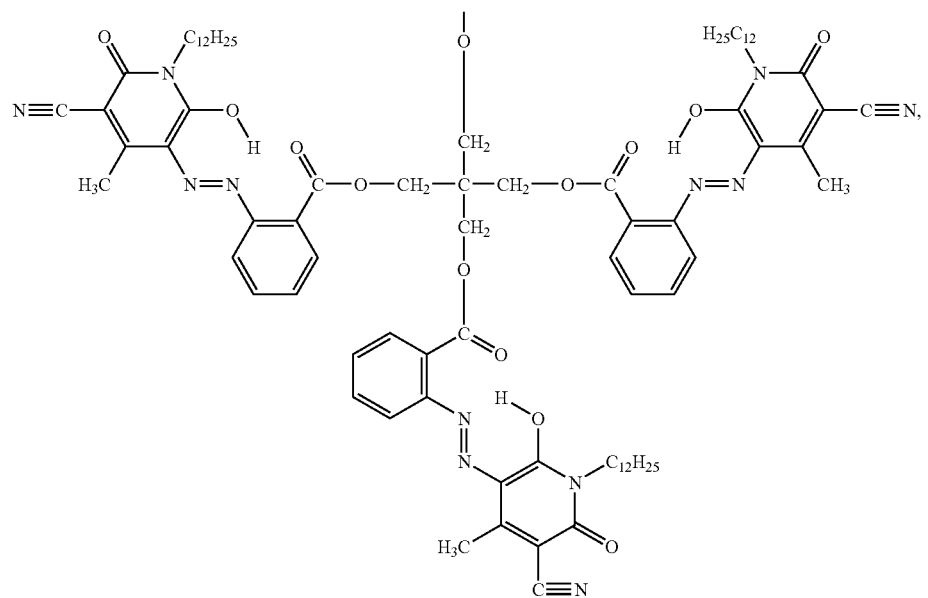
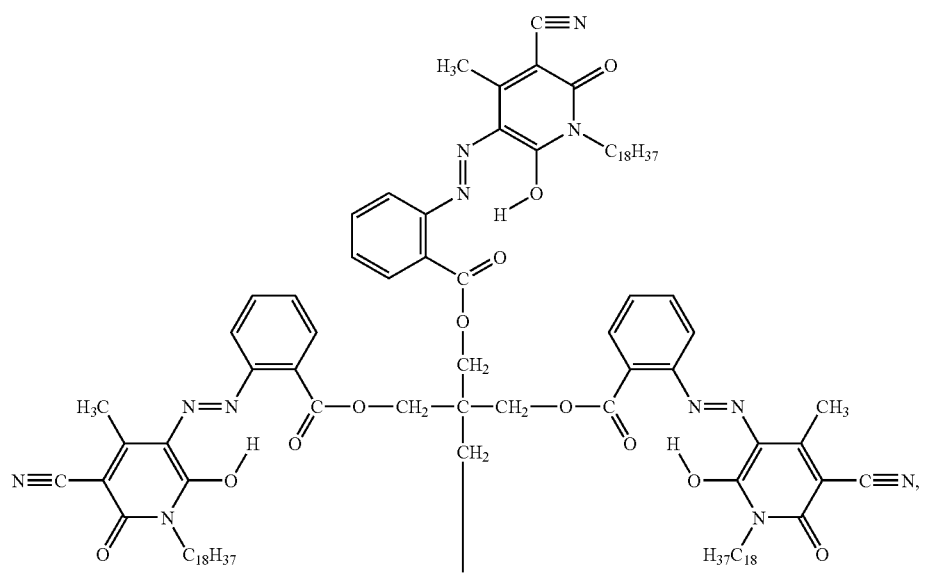

-continued
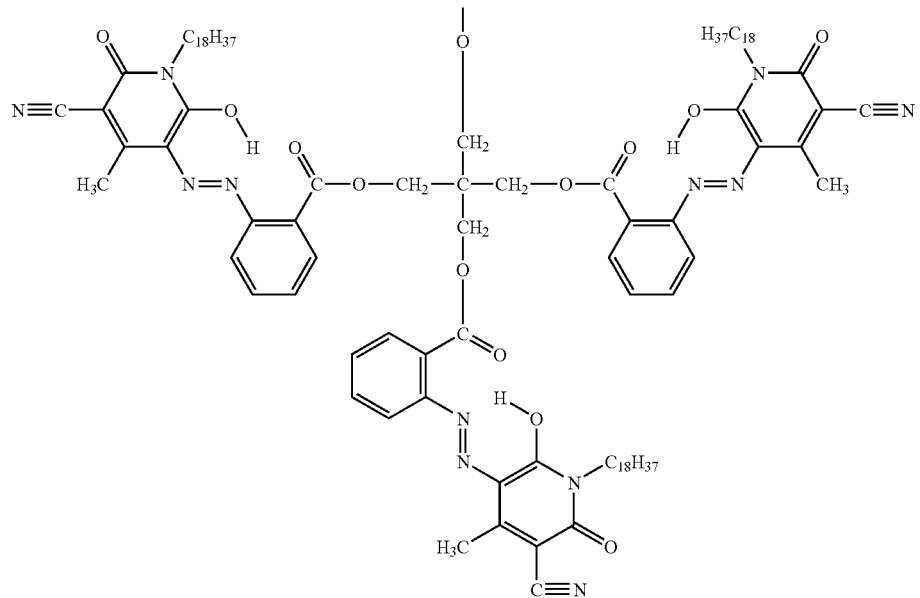
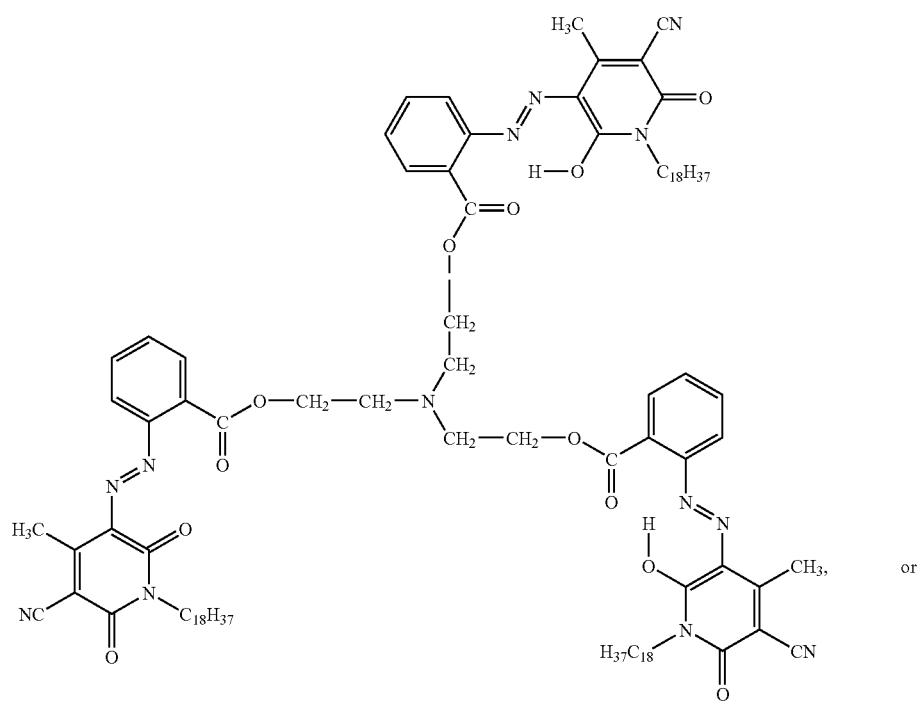
or

-continued

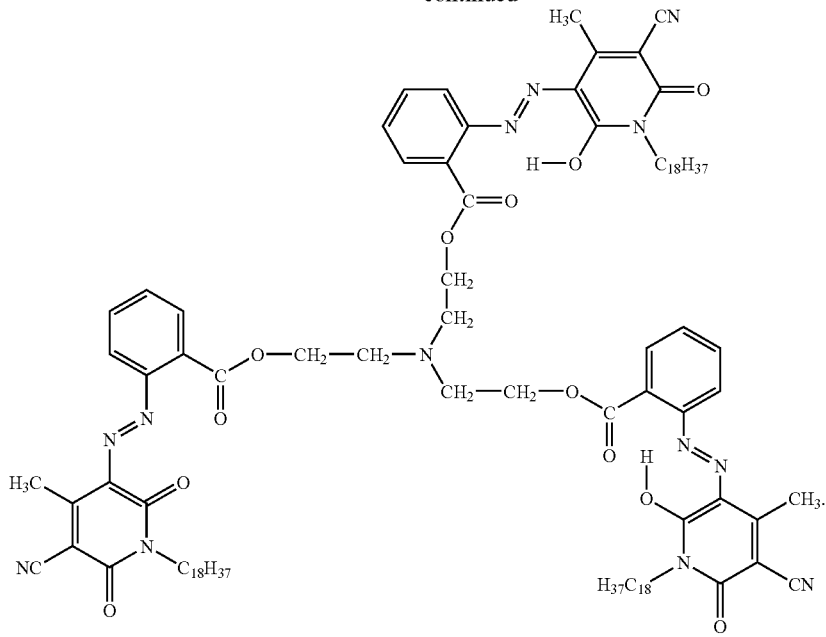

7. A phase change ink according to claim 1 wherein the moieties are bonded to a monomeric group of atoms.

8. A phase change ink according to claim 1 wherein the moieties are bonded to an oligomer or polymer.

9. A phase change ink according to claim 8 wherein the oligomer or polymer has no more than about 20 repeat monomer units.

10. A phase change ink according to claim 8 wherein the oligomer or polymer has at least about 10 repeat monomer units.

11. A phase change ink according to claim 8 wherein the oligomer or polymer has at least about 6 of the moieties pendant therefrom and wherein the oligomer or polymer has no more than about 30 of the moieties pendant therefrom.

12. A phase change ink according to claim 8 wherein the oligomer or polymer has at least about 10 of the moieties pendant therefrom and wherein the oligomer or polymer has no more than about 20 of the moieties pendant therefrom.

13. A phase change ink according to claim 1 wherein $R_3$ is methyl.

14. A phase change ink according to claim 1 wherein $R_1$ is an alkyl or alkylene group and $R_2$ is an alkyl or alkylene group.

15. A phase change ink according to claim 14 wherein at least one of $R_1$ and $R_2$ is an alkyl or alkylene group having at least 8 carbon atoms.

16. A phase change ink according to claim 1 wherein the phase change ink carrier comprises a monoamide, a tetra-amide, or a mixture thereof.

17. A phase change ink according to claim 1 wherein the phase change ink carrier comprises (a) stearyl stearamide, (b) a dimer acid based tetra-amide that is the reaction product of dimer acid, ethylene diamine, and a carboxylic acid having at least about 36 carbon atoms, or (c) mixtures thereof.

18. A phase change ink according to claim 1 wherein the phase change ink carrier comprises an isocyanate-derived material.

19. A phase change ink according to claim 1 wherein the phase change ink carrier comprises a mixture of one or more amides and one or more isocyanate-derived materials.

20. A phase change ink according to claim 1 wherein the phase change ink carrier comprises one or more materials selected from paraffins, microcrystalline waxes, polyethylene waxes, ester waxes, amide waxes, fatty acids, fatty alcohols, fatty amides, sulfonamide materials, tall oil rosins, rosin esters, ethylene/vinyl acetate copolymers, ethylene/acrylic acid copolymers, ethylene/vinyl acetate/acrylic acid copolymers, copolymers of acrylic acid with polyamides, ionomers, and mixtures thereof.

21. A phase change ink according to claim 1 wherein the colorant is present in the ink in an amount of at least about 0.1 percent by weight of the ink and in an amount of no more than about 20 percent by weight of the ink.

22. A phase change ink according to claim 1 wherein the ink has a melting point of no lower than about 70° C. and wherein the ink has a melting point of no higher than about 140° C.

23. A process which comprises (1) incorporating into an ink jet printing apparatus a phase change ink composition comprising a phase change ink carrier and a colorant compound comprising three or more moieties of the formula

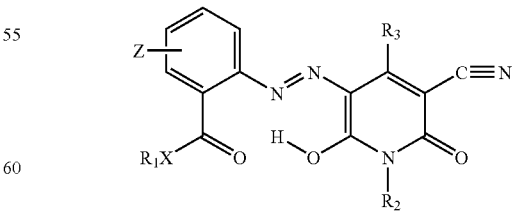

wherein (A) each $R_1$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, or (vi) a siloxy group, (B) each $R_2$, independently of the others, is (i) an alkyl or alkylene group, (ii) an aryl or arylene group, (iii) an arylalkyl or arylalkylene group, (iv) an alkylaryl or alkylarylene group, (v) a silyl or silylene group, (vi) a siloxy group, or (vii) a group of the formula

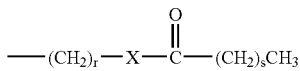

wherein r and s are each, independently of the other, integers representing a number of repeat —CH$_2$— groups, (C) each R$_3$, independently of the others, is (i) an alkyl group, (ii) an aryl group, (iii) an arylalkyl group, or (iv) an alkylaryl group, (D) each X, independently of the others, is (i) a direct bond, (ii) an oxygen atom, (iii) a sulfur atom, (iv) a group of the formula —NR$_{40}$— wherein R$_{40}$ is a hydrogen atom, an alkyl group, an aryl group, an arylalkyl group, or an alkylaryl group, or (v) a group of the formula —CR$_{50}$R$_{60}$— wherein R$_{50}$ and R$_{60}$ each, independently of the other, is a hydrogen atom, an alkyl group, an aryl group, an arylalkyl group, or an alkylaryl group, and (E) each Z, independently of the others, is (i) a hydrogen atom, (ii) a halogen atom, (iii) a nitro group, (iv) an alkyl group, (v) an aryl group, (vi) an arylalkyl group, (vii) an alkylaryl group, (viii) a group of the formula

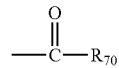

wherein R$_{70}$ is an alkyl group, an aryl group, an arylalkyl group, an alkylaryl group, a silyl group, or a siloxy group, (ix) a sulfonyl group of the formula —SO$_2$R$_{80}$ wherein R$_{80}$ is a hydrogen atom, an alkyl group, an aryl group, an arylalkyl group, an alkylaryl group, a silyl group, or a siloxy group, or (x) a phosphoryl group of the formula —PO$_3$R$_{90}$ wherein R$_{90}$ is a hydrogen atom, an alkyl group, an aryl group, an arylalkyl group, an alkylaryl group, a silyl group, or a siloxy group; said moieties being bonded to a central atom, monomeric group of atoms, oligomer, or polymer; (2) melting the ink; and (3) causing droplets of the melted ink to be ejected in an imagewise pattern onto a substrate.

24. A process according to claim 23 wherein the substrate is an intermediate transfer member and droplets of the melted ink are ejected in an imagewise pattern onto the intermediate transfer member followed by transfer of the imagewise pattern from the intermediate transfer member to a final recording sheet.

25. A process according to claim 24 wherein the intermediate transfer member is heated to a temperature above that of the final recording sheet and below that of the melted ink in the printing apparatus.

* * * * *